United States Patent [19]

Carmosin et al.

[11] Patent Number: 5,508,424

[45] Date of Patent: Apr. 16, 1996

[54] 4-ARYLISOINDOLE ANALGESICS

[75] Inventors: Richard J. Carmosin, Quakertown; John R. Carson, Norristown, both of Pa.; Dennis C. Liotta, McDonough, Ga.; Philip Pitis, North Wales; Robert B. Raffa, Norristown, both of Pa.

[73] Assignee: Ortho Pharmaceutical Corporation, Del.

[21] Appl. No.: 173,586

[22] Filed: Dec. 23, 1993

Related U.S. Application Data

[63] Continuation-in-part of Ser. No. 99,965, Jul. 29, 1993, abandoned, which is a continuation-in-part of Ser. No. 38,571, Mar. 26, 1993, abandoned.

[51] Int. Cl.⁶ .................. C07D 403/10; C07D 31/40; C07D 409/10; A61K 31/41; A61K 31/44
[52] U.S. Cl. ............... 546/281; 548/452; 548/466
[58] Field of Search ...................... 548/466, 452; 546/281; 514/339

[56] References Cited

U.S. PATENT DOCUMENTS

| | | | |
|---|---|---|---|
| 4,042,707 | 8/1977 | Ripka | 424/274 |
| 4,689,329 | 8/1987 | Carmosin et al. | 514/299 |
| 5,216,018 | 6/1993 | Ciganek | 514/416 |

FOREIGN PATENT DOCUMENTS

0514273A1  5/1992  European Pat. Off. .

*Primary Examiner*—David B. Springer
*Attorney, Agent, or Firm*—John Harbour

[57] ABSTRACT

The 4-arylisoindoles of the following formula are effective analgesics:

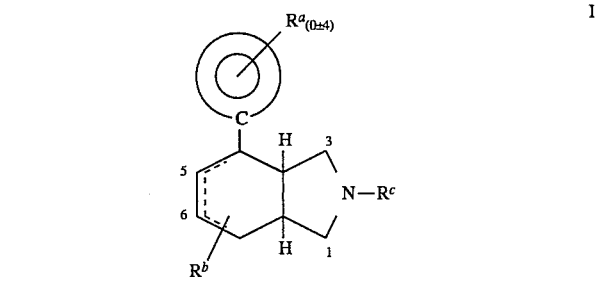

including stereoisomers and pharmaceutically acceptable salts thereof, wherein

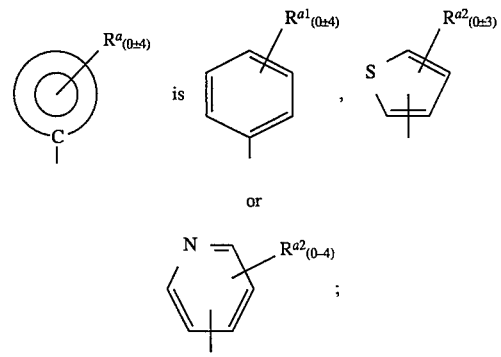

with the proviso that there is 0 or 1 unsaturated bond in the isoindole ring and with the proviso that where the stereoisomer is:

a) the 3aβ, 4β, 7aα diastereomer, then a double bond joins the 5- and 6-position carbons or the 6- and 7-position carbons;

b) the 3aβ, 4α, 7aα or the 3aβ, 4α, 7aβ diastereomers, then the double bond joins the 5- and 6-position carbons; and c) the 3aβ, 4β, 7aβ diastereomer, then the double bond joins the 6- and 7-position carbons.

18 Claims, No Drawings

4-ARYLISOINDOLE ANALGESICS

RELATED APPLICATIONS

This is a Continuation-In-Part of Ser. No. 99,965, filed Jul. 29, 1993 which is a Continuation-In-Part of Ser. No. 38,571, filed Mar. 26, 1993 both are now abandoned.

The present invention relates to analgesics. More particularly, the present invention relates to 4-aryl(octahydro or hexahydro)-1H-isoindoles having analgesic activity.

BACKGROUND OF THE INVENTION

Analgesics used today in clinical practice suffer either from limited efficacy, limiting side effects or both. The non-steriodal antiinflammatory agents such as aspirin and ibuprofen fail to treat severe pain and cause gastrointestinal side effects. The opiates (morphine, codeine or meperidine) can treat more severe pain, but are subject to addiction liability and cause constipation and respiratory depression.

French Patent 8915407, to Rorer-Rhone Polenc, discloses the compound:

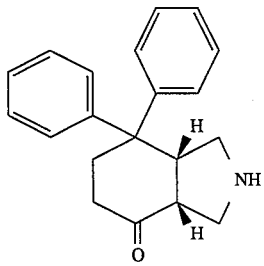

No biological utility is taught.

Eur. Pat. No. 430 771, to Rhone Polenc, discloses the compound:

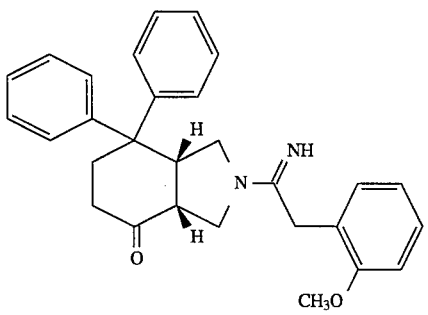

The biological utility is disclosed as a Substance P antagonist.

Ciba-Giegy has publicly disclosed the compound:

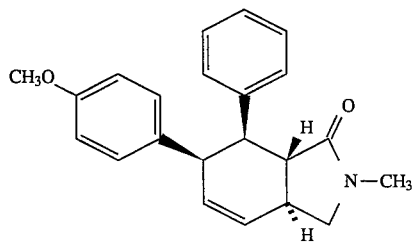

However, no biological activity was taught for this compound and its suitability for use as an analgesic is unknown.

U.S. Pat. No. 5,216,018, to Ciganek discloses isoindoles of the formula:

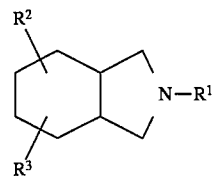

wherein $R^2$ and $R^3$ are disclosed among many other substituents to be independently phenyl. These compounds are disclosed as useful to treat physiological or drug induced psychosis and as antidyskinetic agents.

SUMMARY Of THE INVENTION

The present invention provides novel octahydro or hexahydro-1H-isoindoles having analgesic activity of the formula:

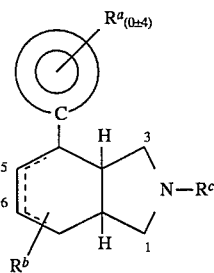

including the purified stereoisomers and pharmaceutically acceptable salts thereof, wherein

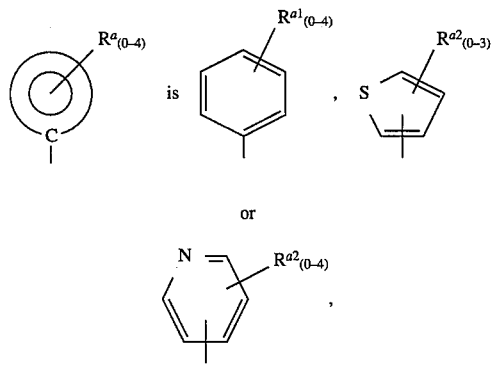

$R^{a1}$ is selected from the group consisting of hydroxy, halogen, $C_{1-4}$alkyl, substituted $C_{1-4}$alkyl (wherein the substituent is $C_{1-4}$alkoxy, hydroxy or perhalo), $C_{1-4}$alkoxy, substituted $C_{1-4}$alkoxy (wherein the substituent is perfluoro), $C_{1-4}$alkylthio, cyano, nitro, amino, $C_{1-4}$alkylamino, di$C_{1-4}$alkylamino, $C_{1-4}$alkylsulfonyl, $C_{1-4}$alkylsulfinyl, phenyl, phenylthio, $C_{1-4}$acylamino, carboxy, $C_{1-4}$acyl and benzoyl;

$R^{a2}$ is selected from the group consisting of halogen or $C_{1-4}$alkyl; $R^b$ is 5-, 6-, or 7-position substituted and selected from the group consisting of hydrogen and $C_{1-4}$ alkyl; and $R^c$ is selected from the group consisting of hydrogen, $C_{1-4}$ alkyl, substituted $C_{1-4}$alkyl (wherein the substituent is one or two phenyl groups or di$C_{1-4}$alkylamino), $C_{1-4}$alkenyl, benzyl, $C_{1-6}$cycloalkylmethyl and $C_{1-6}$cycloalkyl;

with the proviso that there is 0 or 1 unsaturated bond in the isoindole ring and with the proviso that where the stereoisomer is:

a) the 3aβ, 4β, 7aα diastereomer, then a double bond joins the 5- and 6-position carbons or the 6- and 7-position carbons;

b) the 3aβ, 4α, 7aα or the 3aβ, 4α, 7aβ diastereomers, then the double bond joins the 5- and 6-position carbons; and c) the 3aβ, 4β, 7aβ diastereomer, then the double bond joins the 6- and 7-position carbons.

DETAILED DESCRIPTION OF THE INVENTION

The compounds of Formula (I) can be divided into six diastereomers:

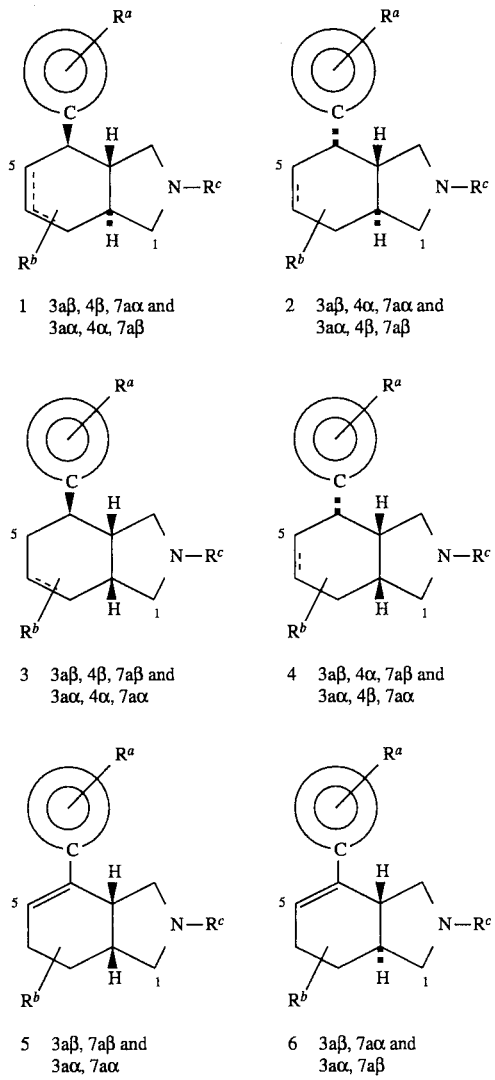

1  3aβ, 4β, 7aα and
   3aα, 4α, 7aβ

2  3aβ, 4α, 7aα and
   3aα, 4β, 7aβ

3  3aβ, 4β, 7aβ and
   3aα, 4α, 7aα

4  3aβ, 4α, 7aβ and
   3aα, 4β, 7aα

5  3aβ, 7aβ and
   3aα, 7aα

6  3aβ, 7aα and
   3aα, 7aβ where $R^a$, $R^b$ and $R^c$ are as defined above. Unless specifically indicated otherwise, the structures herein represent the depicted stereoisomer as a racemic mixture.

The manufacture of compounds of Formula (I) may be carried out in a two-stage synthesis scheme followed by a final step in which any protecting groups are removed. The objective of the first synthetic stage is to produce the desired stereoisomer of a core 4-aryl(octahydro or hexahydro)-1H-isoindole. The objective of the second synthetic stage is to substitute the core 4-aryl(octahydro or hexahydro)-1H-isoindole with desired $R^a$, $R^b$ and $R^c$ substituents (where $R^a$ is used generically to refer to both $R^{a1}$ and $R^{a2}$). Of course, persons skilled in the art will immediately realize the two objectives are not always separable. In a first scenario, the second synthetic stage is performed initially where desired $R^a$, $R^b$ and $R^c$ are substituted on the starting materials for the core 4-aryl(octahydro or hexahydro)-1H-isoindole synthesis and carried through the synthesis unchanged. A second scenario is identical to the first except that protecting groups may be employed through the synthesis and removed thereafter. In a third scenario, precursor substituents may be added to the starting materials or any of the intermediates to the core 4-phenyl(octahydro or hexahydro)-1H-isoindole and elaborated to desired $R^a$, $R^b$ and $R^c$ substituents following formation of the core compound. In a fourth scenario, suitable $R^a$, $R^b$ and $R^c$ substituents on the core 4-aryl(octahydro or hexahydro)-1H-isoindole may themselves be further elaborated to other such substituents. Thus, the two synthetic stages may be sequentially or simultaneously performed with the separable objectives of producing the core 4-aryl(octahydro or hexahydro)- 1H-isoindole and appropriate substituents thereon.

Flow Sheets AA through AE illustrate the first synthetic stage for the production of core 4-aryl(octahydro or hexahydro)-1H-isoindole. In each of the Flow Sheets, the case in which the aryl is phenyl is exemplified. The core compound of Formula I has three stereocenters and, in consequence, $2^3$ or 8 stereoisomers which include 4 diastereomers. The instant invention anticipates biological activity in each of the 4 diastereomers. Thus, Flow Sheets AA through AE, illustrate syntheses by which each of the 4 diastereomers may be produced. The following is a description of the chemistry employed in each suggested procedure.

AA: Synthesis of diastereomers 1 and 3

Diastereomers 1 and 3 of Flow Scheme AA are obtained from commonly available starting materials which include pyridine or substituted pyridines and trans-cinnamoyl chloride or substituted trans-cinnamoyl chloride. Of course, the equivalent acid chloride or substituted acid chloride with pyridine or thiophene rather than phenyl would be employed in Flow Sheet AA as starting material AA3 to obtain these alternate aryl moieties at the 4-position of the desired octahydro or hexahydro-1H-isoindole. The description herein using the phenyl bearing trans-cinnamic acid is for exemplification only. In a first step, pyridine is converted to an N-substituted pyridinium salt AA1 by reaction with $R^c I$, i.e. benzyl iodide, methyl iodide, ethyl iodide, etc., forming the iodide salt. Subsequently, pyridinium salt AA1 is ring opened by refluxing in a suspension of sodium aluminum hydride or lithium aluminum hydride in a suitable solvent, such as, THF, to form cis-dienylamine AA2. The resulting cis-dienylamine AA2 might be substituted on any of carbons 1 to 5 depending upon the position of $R^a$ on the pyridine starting material. Those compounds AA2 that are 1- or 2-$R^a$ substituted might be conveniently separated at this point by standard techniques as they will not result in compounds of formula I. Cis-amine AA2 is subsequently acylated with trans-cinnamoyl chloride or substituted trans-cinnamoyl chloride AA3 to form diene/dienophile AA4. This acylation might be carried out in a suitable solvent, such as, THF, with a base, for instance, NaOH, optionally applying heat. Diene/dienophile AA4 may be ring closed in an intramolecular Diels-Alder reaction to give a mixture of bicyclic compounds AA5 and AA6. By Flow Sheet AA, isomer AA6 predominates. The intramolecular Diels-Alder reaction is preferably carried out by simply heating diene/dienophile AA4 in a high boiling organic solvent. Suitable high boiling organic solvents boil in a temperature range between 80° and 250° C. and include, for example, toluene, xylene and dichlorobenzene. The reaction might also be carried out with a lower boiling solvent in a pressure apparatus. Preferably the reaction is carried out in a temperature range between 100° and 180° C. under normal pressure. Bicyclic compounds AA5 and AA6 are consecutively hydrogenated and subjected to hydride reduction to produce 4-phenyl(octahydro or hexahydro)-1H-isoindoles 1 and 3, respectively. The hydrogenation may be carried out over Raney nickel or over a noble metal, such as, palladium, platinum, rhodium or nickel, with or without heat and at pressures from atmospheric to 1000 psi. In the case where $R^a$ is nitro, it is preferred that the hydrogenation be carried out over ruthenium. The hydride reduction is carried out with a reducing agent in a suitable organic solvent, such as, THF. Suitable reducing agents include lithium aluminum hydride, sodium diethyl aluminum hydride, borane-methylsulfide and borane-THF. Bicyclic compounds AA5 and AA6 are subjected to hydride reduction to produce the delta-6,7 isoindoles 1 and 3, respectively. In this hydride reduction, suitable reducing agents include lithium aluminum hydride and sodium diethyl aluminum hydride.

FLOW SHEET AA

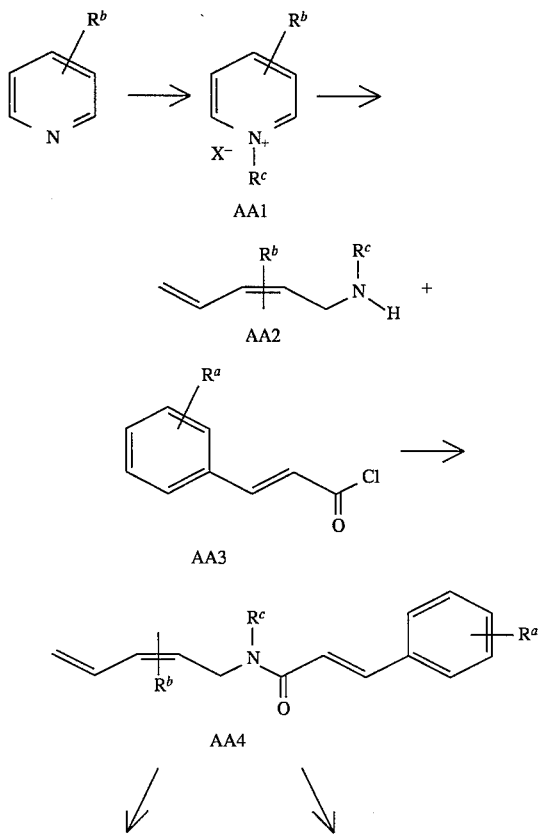

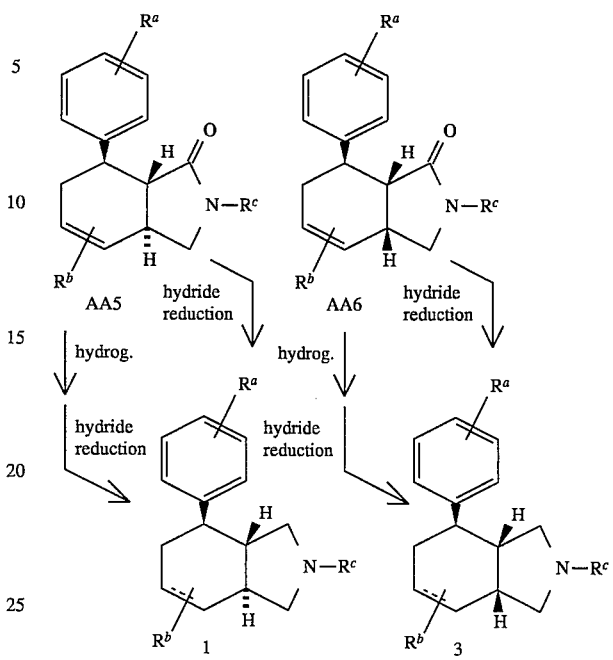

AB: Synthesis of diastereomers 1 and 3

Diastereomers 1 and 3 of Flow Scheme AB are obtained from commonly available starting materials which include $R^c$-aminoethanol, trans-cinnamoyl chloride or substituted trans-cinnamoyl chloride and allylidenetriphenylphosphorane. Of course, the equivalent acid chloride or substituted acid chloride with pyridine or thiophene rather than phenyl would be employed in Flow Sheet AB as starting material AB2 to obtain these alternate aryl moieties at the 4-position of the desired octahydro or hexahydro-1H-isoindole. The description herein using the phenyl bearing trans-cinnamic acid is for exemplification only. In a first step, aminoalcohol AB1 is acylated with trans-cinnamoyl chloride or substituted trans-cinnamoyl chloride AB2 to form hydroxyamide AB3. This acylation might be carried out in a suitable solvent, such as, THF, with a base, for instance, NaOH, optionally applying heat. Hydroxyamide AB3 is converted to the corresponding aldehyde AB4 by a Swern oxidation. This oxidation may be carried out in methylene chloride at from −70° C. to room temperature employing oxalyl chloride-dimethyl sulfoxide-diethylamine. In the next step of Flow Sheet AB, reaction of aldehyde AB4 with allylidenetriphenylphosphorane AB5 affords the diene AB6. The allylidenetriphenylphosphorane is generated in solution from an allyl triphenylphosphonium halide and base. The halogen salt, allyl triphenylphosphonium bromide, is formed from a mixture of triphenylphosphine and allyl bromide upon standing for a few days. The chlorine salt would also be useful and both the chlorine and bromine halogen salts are available on the market. The Wittig reaction is carried out in a suitable organic solvent, such as, an ethereal solvent, and the salt is dehydrohalogenated by the addition of a sufficiently strong base to produce the reactive allylidenetriphenylphosphorane, AB5. Suitable bases include phenyllithium or NaN[Si(CH$_3$)$_3$]$_2$. The objective diene/dienophile AB6, both cis and trans at the diene, is produced upon the mixture standing at room temperature for from a few minutes to overnight with the adducts triphenylphosphine oxide and metal salt separating. Diene/dienophile AB6 may be ring closed in an intramolecular Diels-Alder reaction to give a mixture of bicyclic compounds AB7 and AB8. The intramolecular Diels-Alder reaction is preferably carried out by simply heating diene/dienophile AB6 in a high boiling organic solvent. Suitable high boiling organic solvents boil in a temperature range between 80° and 250° C. and include, for example, toluene, xylene and dichlorobenzene. The reaction might also be carried out with a lower boiling solvent in a pressure apparatus. Preferably the reaction is carried out in a temperature range between 100° and 180° C. under normal pressure. Bicyclic compounds AB7 and AB8 are consecutively hydrogenated and subjected to hydride reduction to produce 4-phenyl-1H-isoindoles 3 and 1, respectively. The hydrogenation may be carried out over Raney nickel or over a noble metal, such as, palladium, platinum, rhodium or nickel, with or without heat and at pressures from atmospheric to 1000 psi. In the case where $R^a$ is nitro, it is preferred that the hydrogenation be carried out over ruthenium. The hydride reduction is carried out with a reducing agent in a suitable organic solvent, such as, THF. Suitable reducing agents include lithium aluminum hydride, sodium diethyl aluminum hydride, borane methylsulfide and borane-THF. Bicyclic compounds AB7 and AB8 are subjected to hydride reduction to produce the delta-6,7 isoindoles 3 and 1, respectively. In this hydride reduction, suitable reducing agents include lithium aluminum hydride and sodium diethyl aluminum hydride.

FLOW SHEET AB

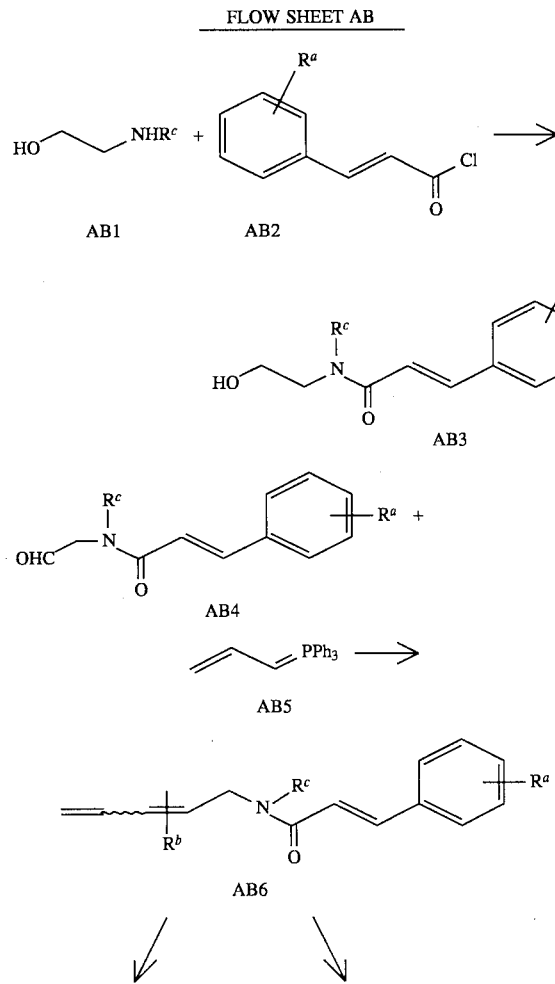

-continued
FLOW SHEET AB

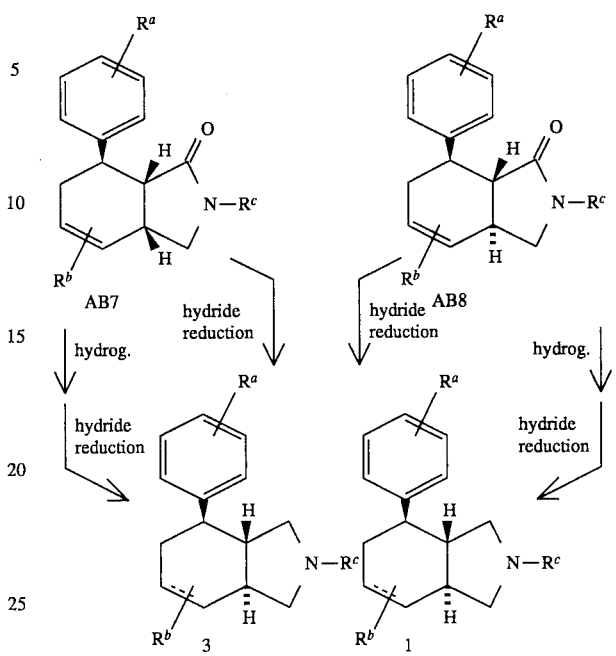

AC: Synthesis of diastereomers 1 and 3

Diastereomers 1 and 3 of Flow Scheme AC are obtained from commonly available starting materials which include trans-cinnamoyl chloride or substituted trans-cinnamoyl chloride and trans-2,4-pentadienoic acid or substituted trans-2,4-pentadienoic acid. Of course, the equivalent acid chloride or substituted acid chloride with pyridine or thiophene rather than phenyl would be employed in Flow Sheet AC as starting material AC5 to obtain these alternate aryl moieties at the 4-position of the desired octahydro or hexahydro-1H-isoindole. The description herein using the phenyl bearing trans-cinnamic acid is for exemplification only. In a first step, trans-dienoic acid AC1 is reduced to the corresponding alcohol AC2 in a solvent with a hydride reducing agent. Compound AC1 is available on the market or is easily prepared by persons skilled in the art. To produce desirable compounds herein, $R^b$ of compound AC1 is a 3-, 4- or 5-position substituent. Suitable reducing agents include lithium aluminum hydride (LAH) and sodium diethylaluminum hydride. Preferred solvents for use with the named reducing agents are the ethereal solvents. Subsequently, trans-dienylcarbinol AC2 is oxidized or halogenated to trans-diene AC3 wherein $Z^a$ is formyl or halomethyl, i.e., chloromethyl, bromomethyl or iodomethyl. The oxidation of an alcohol to an aldehyde is well known. In this instance, care must be taken in choosing an oxidation process that the oxidation is severe enough to act on the alcohol, but not so severe that the diene is also oxidized. Two alternative processes are suggested herein. In one alternative, trans-dienylcarbinol AC2 is reacted with the complex formed by chromium trioxide and pyridine in a halocarbon solvent to give $Z^a$ as formyl in good yield. With excess reagent, i.e., complex, this oxidation proceeds to completion at room temperature in from minutes to hours. Suitable reagents include pyridinium chromate and pyridinium chlorochromate. In the second alternative, manganese dioxide is well known to oxidize an allylic hydroxyl, such as found in trans-dienylcarbinol AC2, to an aldehyde. This oxidation will proceed at room temperature in an inert organic solvent, such as, toluene, in good yield. Halogenations of the type converting trans-dienylcarbinol AC2 to trans-diene AC3 wherein $Z^a$ is halomethyl are also well known. Hydroxyalkanes or hydroxyalkenes are well known to react with phosphorus based halogenating agents to produce the corresponding alkyl or alkenylhalide. This reaction will proceed in good yield at room temperature in an inert solvent, such as, a halocarbon, where the phosphorus based halogenating agent is $PCl_3$, $PBr_3$ or methyl triphenoxyphosphonium iodide. Trans-diene AC3 wherein $Z^a$ is formyl or halomethyl is conveniently aminated to amine/trans-diene AC4. In the case where $Z^a$ is formyl, trans-diene AC3 is reacted with $R^cNH_2$ in the presence of sodium cyanoborohydride and in a solvent, such as, methanol or acetonitrile, to produce trans-dienylamine AC4. In the case where $Z^a$ is halomethyl, trans-diene AC3 is reacted with excess $R^cNH_2$ at room temperature in an inert solvent or an alcohol to produce amine/trans-diene AC4. Amine/trans-diene AC4 is subsequently acylated with trans-cinnamoyl chloride or substituted trans-cinnamoyl chloride AC5 to form diene/dienophile AC6. This acylation might be carried out in a suitable solvent, such as, THF, with a base, for instance, NaOH, optionally applying heat. Diene/dienophile AC6 may be ring closed in an intramolecular Diels-Alder reaction to give a mixture of bicyclic compounds AC7 and AC8. The intramolecular Diels-Alder reaction is preferably carried out by simply heating diene/dienophile AC6 in a high boiling organic solvent. Suitable high boiling organic solvents boil in a temperature range between 80° and 250° C. and include, for example, toluene, xylene and dichlorobenzene. The reaction might also be carried out with a lower boiling solvent in a pressure apparatus. Preferably the reaction is carried out in a temperature range between 100° and 180° C. under normal pressure. Bicyclic compounds AC7 and AC8 are consecutively hydrogenated and subjected to hydride reduction to produce 4-phenyl(octahydro or hexahydro)-1H-isoindoles 1 and 3, respectively. The hydrogenation may be carried out over Raney nickel or over a noble metal, such as, palladium, platinum, rhodium or nickel, with or without heat and at pressures from atmospheric to 1000 psi. In the case where $R^a$ is nitro, it is preferred that the hydrogenation be carried out over ruthenium. The hydride reduction is carried out with a reducing agent in a suitable organic solvent, such as, THF. Suitable reducing agents include lithium aluminum hydride, sodium diethyl aluminum hydride, borane-methylsulfide and borane-THF. Bicyclic compounds AC7 and AC8 are subjected to hydride reduction to produce the delta-6,7 isoindoles 3 and 1, respectively. In this hydride reduction, suitable reducing agents include lithium aluminum hydride and sodium diethyl aluminum hydride.

FLOW SHEET AC

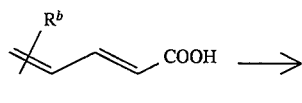

AC1

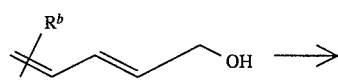

AC2

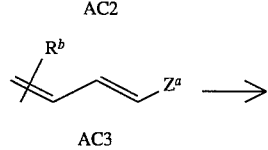

AC3

-continued
FLOW SHEET AC

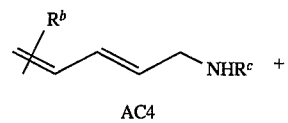

AC4 +

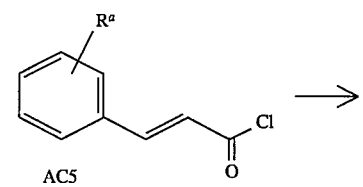

AC5

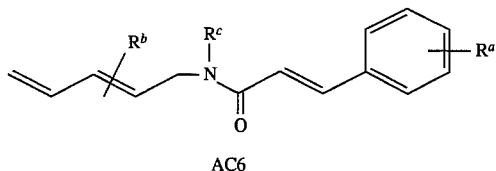

AC6

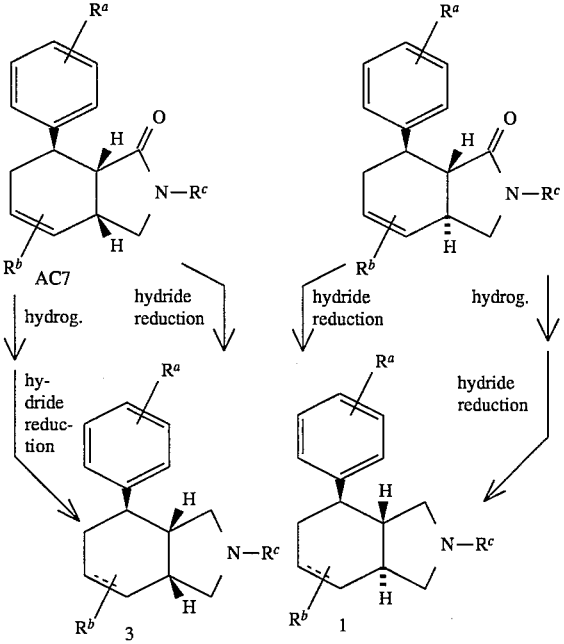

AD: Synthesis of diastereomers 1 and 2

Diastereomers 1 and 2 of Flow Scheme AD may be obtained from commonly available starting materials which include trans-1-phenyl-1,3-butadienes which are 2,3 or 4 $R^b$ substituted, fumaric acid esters and primary amines. Of course, the equivalent trans-buta-1,3-dienes with 1-pyridine or 1-thiophene rather than 1-phenyl would be employed in Flow Sheet AD as starting material AD1 to obtain these alternate aryl moieties at the 4-position of the desired octahydro or hexahydro-1H-isoindoles. The description herein using the phenyl bearing trans-buta-1,3-diene is for exemplification only. Referring to Flow Sheet AD, in a first reaction step, trans-1-phenyl-1,3-butadiene AD1 and fumaric acid ester AD2, a dienophile, are reacted in an intermolecular Diels-Alder reaction to produce diastereomeric diesters AD3 and AD4. The Diels-Alder reaction may be carried out adding the diene AD 1 and the dienophile AD2 to an organic solvent and optionally heating or adding a Lewis acid catalyst or pressurizing the reactor. Suitable solvents generally include toluene, xylene, dichlorobenzene, ether, chloromethane, dichloromethane, tetrachloromethane, n-hexane, benzene, ethylene glycol or water. Of course, where heat is to be applied, then a high boiling solvent is desireable. Suitable high boiling organic solvents boil in a temperature range between 80° and 250° C. The reaction might also be carried out with a lower boiling solvent in a pressure apparatus if desired. Suitable Lewis acid catalysts include, aluminum chloride, stannic chloride or boron trifluoride. Preferably the reaction is carried out in a temperature range between room temperature and 180° C. under normal pressure. Subsequently, diesters AD3 and AD4 are consecutively hydrogenated and subjected to hydride reduction to produce diastereomeric diols AD5 and AD6. The hydrogenation may be carried out over Raney nickel or over a noble metal, such as, palladium, platinum, rhodium or nickel, with or without heat and at pressures from atmospheric to 1000 psi. In the case where $R^a$ is nitro, it is preferred that the hydrogenation be carried out over ruthenium. The hydride reduction may be carried out with a reducing agent in a suitable solvent. Suitable reducing agents include lithium aluminum hydride (LAH) and sodium diethylaluminum hydride. Preferred solvents for use with the named reducing agents are the ethereal solvents. Diols AD5 and AD6 are subsequently activated by replacing the hydroxy groups with a leaving group, $Z^b$, such as, iodide, mesylate (methanesulfonate), tosylate (p-toluenesulfonate) or trifluoromethanesulfonate, to produce activated diols AD7 and AD8. In a first activating procedure, the hydroxyl moieties may be converted to a methanesulfonate group by treating with methanesulfonyl chloride in the presence of triethylamine. A suitable solvent, e.g., dichloromethane, is employed and the reaction is carried out at reduced temperatures. In instances where iodide is the desired leaving group, it may be obtained by two procedures, i.e., a second and third activating procedure. In the second procedure, the iodide is obtained from activating methanesulfonyl group, just described, by treatment of the activated compound with sodium iodide in a suitable solvent, e.g., at reduced or ambient temperatures. In the third procedure, the iodide is obtained directly from diols AD5 and AD6 by common methods known to the art. For example, treatment of the hydroxyl group with methyl triphenoxyphosphonium iodide in a suitable solvent, such as dimethylformamide, at reduced or ambient temperatures, directly produces the desired iodide. In a fourth activating procedure, the hydroxyl group may be converted into the reactive trifluoromethanesulfonate (triflate) group. In this procedure, the hydroxyl group is treated with trifluoromethanesulfonic (triflic) anhydride in the presence of a hindered, non-nucleophilic base, such as, 2,6-lutidine, 2,4,6-collidine, or 2,6-di-t-butyl-4-methylpyridine, in a suitable solvent, such as, dichloromethane, at reduced temperatures to generate the triflate activating group.

In the final reaction of Flow Sheet AD, activated diols AD7 and AD8 are converted to diastereomers 1 and 2 by reaction with primary amine compound AD9. In general, the conversion is carried out by simply adding the primary amine AD9 to the activated diol AD7 or AD8 in a suitable solvent at reduced temperature or ambient temperature. Suitable solvents include acetonitrile, alcohols, DMF or dichloromethane.

In order to obtain the delta-5,6 isoindoles 1 and 2, the diesters AD3 and AD4 are subjected to hydride reduction to produce the unsaturated diols AD5 and AD6. AD5 and AD6 are converted via unsaturated intermediates AD7 and AD8 to the delta-5,6 isoindoles 1 and 2. In this hydride reduction, suitable reducing agents include lithium aluminum hydride and sodium diethyl aluminum hydride. Methodology for conversion of the unsaturated intermediates AD5, AD6, AD7 and AD8 to the final products 1 and 2 is identical to the methodology for preparation of the saturated compounds. The delta-4,5 isoindoles 1 and 2 are obtained by isomerizing the delta-5,6 isoindoles 1 and 2 with a strongly basic reagent, such as, potassium t-butoxide.

FLOW SHEET AD

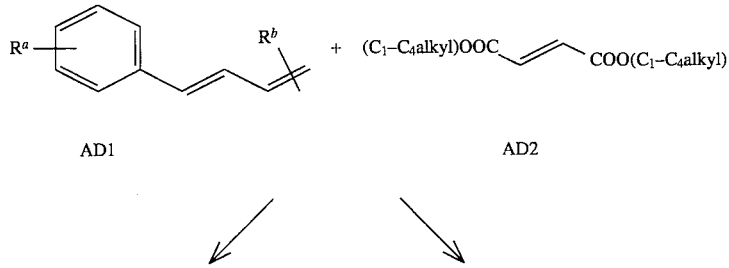

-continued
FLOW SHEET AD

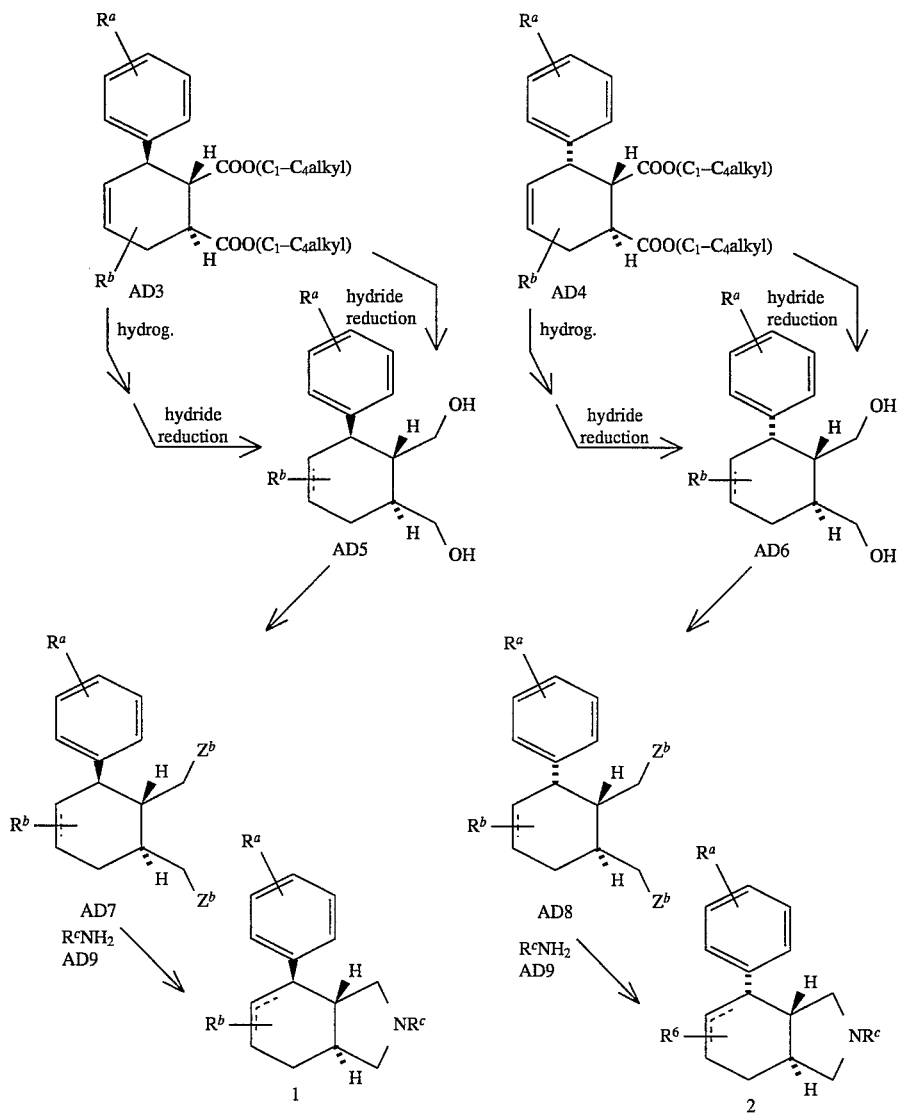

AE: Synthesis of diastereomer 4

Diastereomer 4 of Flow Scheme AE may be obtained from commonly available starting materials which include trans-1-phenyl-1,3-butadienes which are 2,3 or 4 $R^b$ substituted and maleimide. Of course, the equivalent trans-buta-1,3-dienes with 1-pyridine or 1-thiophene rather than 1-phenyl would be employed in Flow Sheet AE as starting material AE1 to obtain these alternate aryl moieties at the 4-position of the desired octahydro or hexahydro-1H-isoindole. The description herein using the phenyl bearing trans-buta-1,3-diene is for exemplification only. Referring to Flow Sheet AE, in a first reaction step, trans-1-phenyl-1,3-butadiene AE1 and maleimide AE2, a dienophile, are reacted in an intermolecular Diels-Alder reaction to produce imide AE3. The Diels-Alder reaction may be carried out adding the diene AE1 and the dienophile AE2 to an organic solvent and optionally heating or adding a Lewis acid catalyst or pressurizing the reactor. Suitable solvents generally include toluene, xylene, dichlorobenzene, ether, chloromethane, dichloromethane, tetrachloromethane, n-hexane or benzene. Of course, where heat is to be applied, then a high boiling solvent is desireable. Suitable high boiling organic solvents boil in a temperature range between 80° and 250° C. The reaction might also be carried out with a lower boiling solvent in a pressure apparatus if desired. Suitable Lewis acid catalysts include, aluminum chloride, stannic chloride or boron fluoride. Preferably the reaction is carried out in a temperature range between room temperature and 180° C. under normal pressure. Subsequently, imide AE3 is consecutively hydrogenated and subjected to hydride reduction to produce diastereomeric product 4. The hydrogenation may be carried out over Raney nickel or over a noble metal, such as, palladium, platinum, rhodium or nickel, with or without heat and at pressures from atmospheric to 1000 psi. In the case where $R^a$ is nitro, it is preferred that the hydrogenation be carried out over ruthenium. The hydride reduction may be carried out with a reducing agent in a suitable solvent, such as THF. Suitable reducing agents include lithium aluminum hydride, sodium diethyl aluminum hydride, borane methylsulfide and borane-THF. Bicyclic compound AE3 is subjected to hydride reduction to produce the delta-5,6 isoindoles 4 or mixtures of the delta-5,6 isoindoles and the delta-4,5 isoindoles. In this hydride reduction, suitable reducing agents include lithium aluminum hydride and sodium diethyl aluminum hydride. The delta-5,6 isoindoles may be isomerized with a strongly basic reagent, such as, potassium t-butoxide to the delta-4,5 isoindole.

FLOW SHEET AE

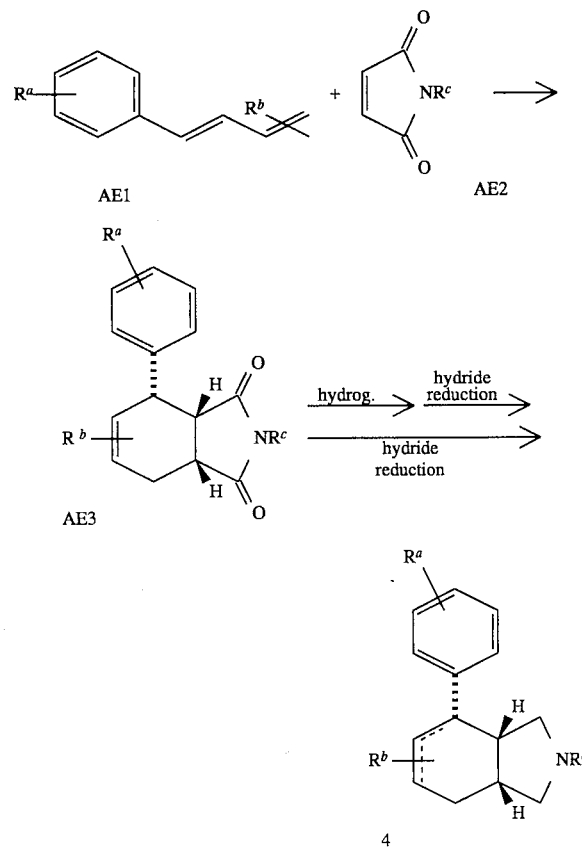

As seen, Flow Sheets AA–AD show the production of mixtures of diastereomers. It is assumed herein that persons skilled in the art will be able to separate diastereomers by chromatographic techniques, crystallization techniques or otherwise. Of course, it is clear that the separation may be performed at a point in the reaction scheme following the production of the diastereomeric mixture. Thus, for example, separation of the diastereomers may be performed in Flow Sheet AD at intermediates AD3 and AD4.

Each of the diastereomers, 1–4, has two enantiomers and the synthetic routes shown above produce racemic mixtures of these enantiomers. The individual enantiomers may be separated by use of a chiral auxilliary on nitrogen. This procedure is illustrated in flow sheet AF. The intermediate from flow sheet AD, AD7, is caused to alkylate a chiral α-phenethylamine AF1, such as, (+) or (–)-α-methylphenethylamine, (+) or (–)-α-methyl-p-chlorophenethylamine or (+) or (–)-α-1-naphthylethylamine. This alkylation is carried out in a suitable solvent at elevated temperature or ambient temperature with a suitable base, such as, potassium carbonate, sodium bicarbonate or diisopropylethylamine. Suitable solvents include acetonitrile, alcohols, DMF or dichloromethane. The alkylation produces two diastereomers, AF2 and AF3. These can be separated chromatographically. The α-phenethyl chiral auxilliary on nitrogen is removed by catalytic debenzylation over a palladium catalyst to give the NH compounds, AF4 and AF5. Alternatively, the chiral auxiliary can be removed by treatment of AF2 and AF3 with a chloroformate reagent, for example, ACE chloride or VOC. The $R^c$ group is then attached to nitrogen either by alkylation or reductive alkylation. In the case of alkylation, an $R^cZ$ reagent is employed where Z is a leaving group as discussed in connection with Flow Sheet AD above. The alkylation is carried out in a suitable solvent at elevated temperature or ambient temperature with a suitable base, such as, potassium carbonate, sodium bicarbonate or diisopropylethylamine. Suitable solvents include acetonitrile, alcohols, DMF or dichloromethane. In the case of reductive alkylation, AF4 and AF5 are reacted with a carbonyl compound and a hydrogen source. The hydrogen source may include hydrogen over a palladium or platinum catalyst or $NaBH_3CN$ or formic acid at elevated temperatures. Where the carbonyl compound is formaldehyde, then $R^c$ is methyl; acetaldehyde, then $R^c$ is ethyl; benzaldehyde, then $R^c$ is benzyl; and acetone, then $R^c$ is isopropyl.

FLOW SHEET AF

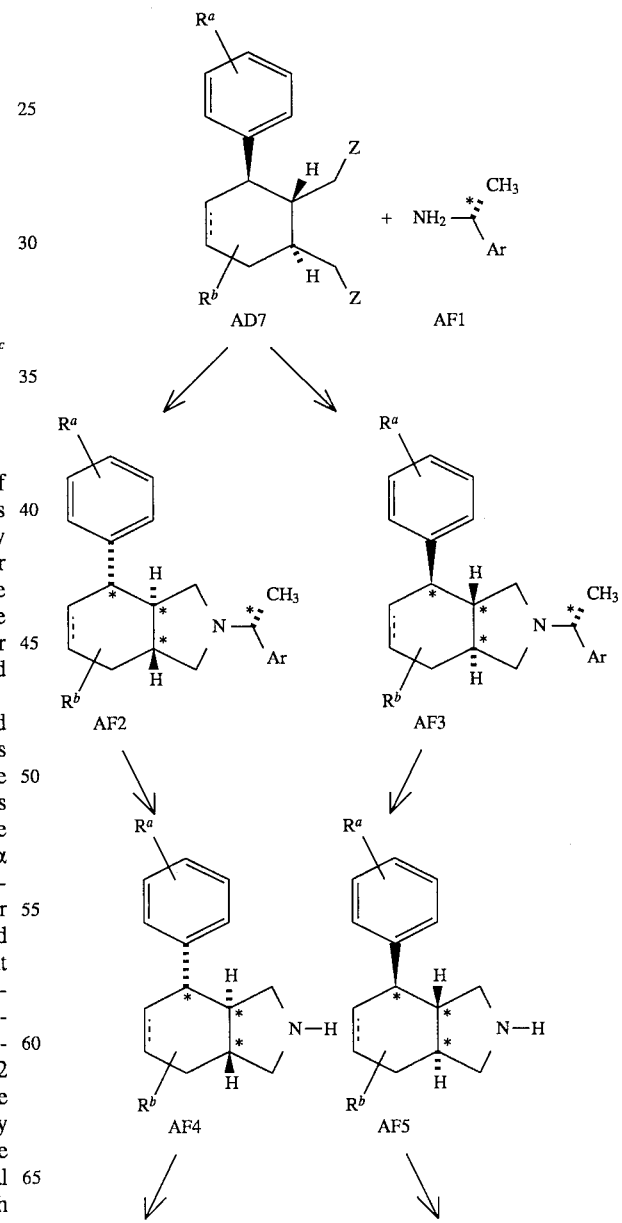

-continued
FLOW SHEET AF

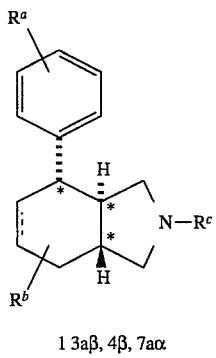

1 3aβ, 4β, 7aα

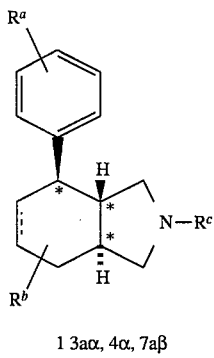

1 3aα, 4α, 7aβ

If in the operation of Flow Sheets AA through AE, at the stage of introduction of $R^c$, a chiral auxiliary is similarly employed, diastereomers will be produced which can be, in like manner, converted to the desired enantiomers. Alternatively, by classical resolution techniques diastereomers 1 through 4 can be reacted with chiral acids, such as, (+) or (−) ditoluoyltartaric acid, (+) or (−) camphorsulfonic acid or (+) or (−) ditolyltartaric acid. Separation of the resultant diastereomeric mixture and subsequent reconversion to the base will produce the desired enantiomers.

As stated, the manufacture of starting materials described above is well known. Trans-cinnamoyl chloride starting materials AA3, AB2 and AC5, as well as the thienyl and pyridyl equivalents, may be produced by either of two condensation reactions. In a Knoevenagel Condensation reaction, an optionally substituted arylaldehyde is reacted with malonic acid, $CH_2(COOH)_2$, in the presence of pyridine to produce a trans-β-arylacrylic acid. In a Perkin Condensation reaction, an optionally substituted arylaldehyde is reacted with acetate, $CH_3COO^-$, in the presence of acetic anhydride to produce the trans-β-arylacrylic acid. The trans-cinnamoyl chloride may be prepared from the trans-cinnamic acid by heating with a halogenating reagent, such as: thionyl chloride, oxalyl chloride or phosphoryl chloride. The starting materials AD1 and AE1, 1-aryl-trans-buta-1,3-dienes, which are 2,3 or 4 $R^b$ substituted or optionally $R^a$ substituted, may be produced in a Wittig reaction. In the Wittig reaction, optionally substituted allyltriphenylphosphonium halide is reacted with optionally substituted arylaldehyde in the presence of a base and in a suitable solvent at from −50° C. to room temperature. Effective bases include potassium t-butoxide, n-butyl lithium and sodium hexamethyldisilazide and useful solvents are inert solvents such as THF. The starting material AE2 may be obtained by adding the primary amine, $R^cNH_2$, to maleic anhydride at room to elevated temperature and condensing the resultant product in situ either by simply heating to about 150° C. or by the addition of a condensing agent such as acetic anhydride or thionyl chloride.

As stated, the objective of the second synthetic stage is to substitute the core 4-phenyl(octahydro or hexahydro)-1H-isoindole with desired $R^a$, $R^b$, and $R^c$. In the case of $R^c$, the desired substituents may be obtained from appropriately substituted starting materials. Specifically, in Flow Sheet AA, starting compound AA1 is appropriately substituted with desired $R^c$. Likewise, in Flow Sheets AB, AC, AD and AE, starting compounds AB1, AC4, AD9 and AE2, consecutively, are appropriately substituted. Alternatively, diverse $R^c$ may be obtained from a benzyl precursor substituent. The benzyl group on nitrogen is removed by catalytic debenzylation over a palladium catalyst to give the NH compound. Alternatively, the benzyl group can be removed by treatment with a chloroformate reagent, for example, ACE chloride or VOC. The $R^c$ group is then attached to nitrogen either by alkylation or reductive alkylation. In the case of alkylation, an $R^cZ$ reagent is employed where Z is a leaving group as discussed in connection with Flow Sheet AD above. The alkylation is carried out in a suitable solvent at elevated temperature or ambient temperature with a suitable base, such as: potassium carbonate, sodium bicarbonate or diisopropylethylamine. Suitable solvents include acetonitrile, alcohols, DMF or dichloromethane. In the case of reductive alkylation the NH compound is reacted with a carbonyl compound and a hydrogen source. The hydrogen source may include hydrogen over a palladium or platinum catalyst or $NaBH_3CN$ or formic acid at elevated temperatures. Where the carbonyl compound is formaldehyde, then $R^c$ is methyl; acetaldehyde, then $R^c$ is ethyl; benzaldehyde, then $R^c$ is benzyl; and acetone, then $R^c$ is isopropyl.

In the case of $R^b$, the desired substituents may be obtained from the appropriately substituted starting materials. Again, specifically, in Flow Sheet AA, starting compound AA1 is appropriately substituted with desired $R^b$. In Flow Sheets AB, AC, AD and AE, starting compounds AB5, AC1, AD1 and AE1 are appropriately substituted. Of course, it is clear in the case of both $R^c$ and $R^b$ that obtaining these desired substituents involves the use of conventional chemistry with relatively well known reactants.

In the case of $R^a$, there is greater variation in both the substituent itself and the substrate to which it is attached and, thus, further description is necessary. The pyridine and thiophene equivalents to trans-cinnamoyl chloride, compounds AA3, AB2 and AC5, or 1-pyridyl-trans-buta-1,3-diene, equivalent to compounds AD1 or AE1, or 1-thienyl-trans-buta-1,3-diene equivalent to compounds AD1 or AE1, are $R^{a2}$ substituted where $R^{a2}$ is halogen or $C_{1-4}$alkyl. Each of the $R^{a2}$ substituents may be synthesized on the thienyl or pyridyl starting material and carried through the synthesis of Flow Sheets AA, AB, AC, AD and AE. As described above, the synthesis of this starting material would require only the synthesis of $R^{a2}$ substituted pyridyl or thienyl aldehyde and the use of this aldehyde in a Knoevenagel Condensation, a Perkin Condensation or a Wittig Reaction. The trans-cinnamoyl chloride, compounds AA3, AB2 and AC5, or trans-1-phenyl-1,3 -butadiene, compounds AD1 or AE1, are $R^{a1}$ substituted where $R^{a1}$ is hydroxy, halogen, $C_{1-4}$alkyl, substituted $C_{1-4}$alkyl (wherein the substituent is $C_{1-4}$alkoxy, hydroxy or perhalo), $C_{1-4}$alkoxy, substituted $C_{1-4}$alkoxy (wherein the substituent is perfluoro), $C_{1-4}$alkylthio, cyano, nitro, amino, $C_{1-4}$alkylamino, $diC_{1-4}$alkylamino, $C_{1-4}$alkylsulfonyl, $C_{1-4}$alkylsulfinyl, phenyl, phenylthio, $C_{1-4}$acylamino, carboxy, $C_{1-4}$acyl and benzoyl.

The majority of the $R^{a1}$ substituents may simply be synthesized on the trans-cinnamoyl chloride or the trans-1-phenyl-1,3-butadiene and carried through the synthesis of Flow Sheets AA, AB, AC, AD or AE. As described above, the synthesis of these starting materials would require only the synthesis of $R^{a1}$ substituted benzaldehyde and the use of this aldehyde in a Knoevenagel Condensation, a Perkin Condensation or a Wittig Reaction. $R^{a1}$ substituents which may be obtained in this manner are halogen, $C_{1-4}$alkyl, substituted $C_{1-4}$alkyl (wherein the substituent is $C_{1-4}$alkoxy or perhalo), $C_{1-4}$alkoxy, substituted $C_{1-4}$alkoxy (wherein the substituent is perfluoro), $C_{1-4}$alkylthio, nitro, $diC_{1-4}$alkylamino, phenyl, phenylthio, $C_{1-4}$acyl and benzoyl. In the case of hydroxy or $C_{1-4}$alkyl substituted with hydroxy, these $R^{a1}$ substituents may be obtained by protecting the hydroxy with methyl or benzyl and, on the octahydro or hexahydro-1H-isoindole, cleaving the protecting group with $BBr_3$ in a halocarbon solvent at reduced temperature or with HBr or Hl in water at elevated temperatures. In the case of cyano, this $R^{a1}$ substituent may be obtained by employing Br as a precursor substituent on the octahydro or hexahydro-1H-isoindole. The bromine precursor substituent is replaced with cyano by treatment with sodium cyanide or cuprous cyanide in an inert solvent at elevated temperatures over a Pd(0) catalyst. In the case of the $C_{1-4}$alkylsulfonyl, these substituents may be obtained by oxidizing a $C_{1-4}$alkylthio precursor substituent on octahydro or hexahydro-1H-isoindole using hydrogen peroxide in acetic acid, potassium permanganate in water, nitric acid, sodium perborate or meta-chloroperbenzoic acid in halocarbon. In the case of the $C_{1-4}$alkylsulfinyl, these substituents may be obtained by oxidizing a $C_{1-4}$alkylthio precursor substituent on octahydro or hexahydro-1H-isoindole using sodium periodate in water or meta-chloroperbenzoic acid in a halocarbon solvent. In the case of amino, this substituent may be obtained by catalytic reduction of $NO_2$ and the alkylamino obtained from the amino by acylation, followed by hydride reduction. In the case of $C_{1-4}$acylamino, these substituents may be obtained by treating an amino precursor substituent on octahydro or hexahydro-1H-isoindole with a $C_{1-4}$carboxylic acid or anhydride. In the case of carboxy, this substituent may be obtained by hydrolyzing a cyano precursor substituent on octahydro or hexahydro-1H-isoindole to carboxamido using polyphosphoric acid at elevated temperatures or by partial saponification with sodium hydroxide, followed by hydrolyzing further with sodium hydroxide.

Preferred $R^{a1}$ are selected from the group consisting of hydroxy, bromine, chlorine, fluorine, methyl, ethyl, n-propyl, i-propyl, t-butyl, methoxymethyl, ethoxyethyl, hydroxymethyl, hydroxyethyl, hydroxypropyl, trifluoromethyl, trichloromethyl, methoxy, ethoxy, t-butoxy, trifluoromethoxy, methylthio, ethylthio, n-propylthio, cyano, nitro, amino, methylamino, ethylamino, n-propylamino, dimethylamino, diethylamino, methylethylamino, methylsulfonyl, ethylsulfonyl, n-propylsulfonyl, methylsulfinyl, ethylsulfinyl, n-propylsulfinyl, phenyl, phenylthio, formylamido, acetamido, propionylamido, carboxy, formyl, acetyl, propionyl and benzoyl;

Preferred $R^{a2}$ are selected from the group consisting of bromine, chlorine, fluorine, methyl, ethyl, n-propyl, i-propyl or t-butyl.

Preferred $R^b$ are selected from the group consisting of hydrogen, methyl, ethyl, n-propyl, i-propyl and t-butyl.

Preferred $R^c$ are selected from the group consisting of hydrogen, methyl, ethyl, n-propyl, i-propyl, t-butyl, benzyl, diphenylmethyl, dimethylaminomethyl, dimethylaminoethyl, dimethylaminopropyl, diethylaminomethyl, diethylaminoethyl, allyl, benzyl, cyclopropylmethyl, cyclopropyl and cyclohexyl.

Preferred compounds of Formula (I) above, include:

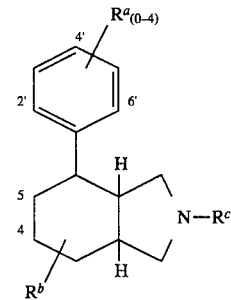

wherein $R^a$, $R^b$ and $R^c$ are simultaneously selected from the group consisting of the groups:

| $R^a$ | $R^b$ | $R^c$ |
|---|---|---|
| 4'-F | 5-Me | Me, |
| 3'-methoxy | H | Me, |
| 3'-methoxy | H | H, |
| 3'-$CF_3$ | H | Me, |
| 3'-methoxy | H | benzyl, |
| 2',3'-dimethoxy | H | Me, |
| 3',4'-dichloro | H | Me, |
| 3'-OH | H | Me, |
| — | H | Me, |
| 4'-$CF_3$ | H | Me, |
| 3'-$CF_3$ | H | n-butyl, |
| 4'-$NO_2$ | H | Me, |
| 4'-$NH_2$ | H | Me, |
| 4'-$NHCOCH_3$ | H | Me, |
| 4'-Cl | H | Me, |
| 2'-Cl | H | Me, |
| 2',5'-dichloro | H | Me, |
| 4'-F | H | Me, |
| 4'-methoxy | H | Me, |
| 3',4'-dimethoxy | H | Me, |
| 4'-i-propyl | H | Me, |
| 4'-CN | H | Me, |
| 4'-Br | H | Me, |
| 4'-SMe | H | Me, |
| 4'-$SO_2Me$ | H | Me, and |
| 3'-methoxy | H | benzyl, | including the stereoisomers thereof.

The most preferred compounds of Formula I are:

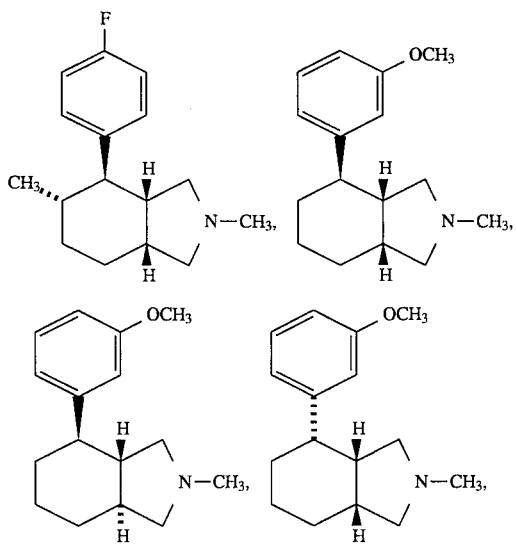

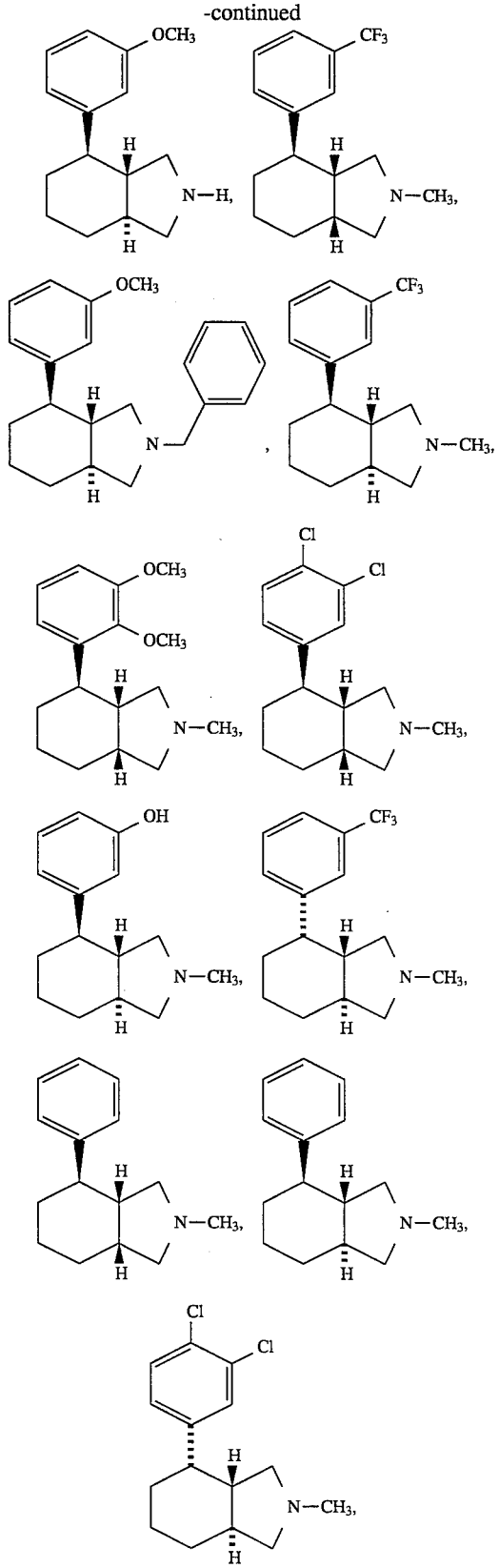
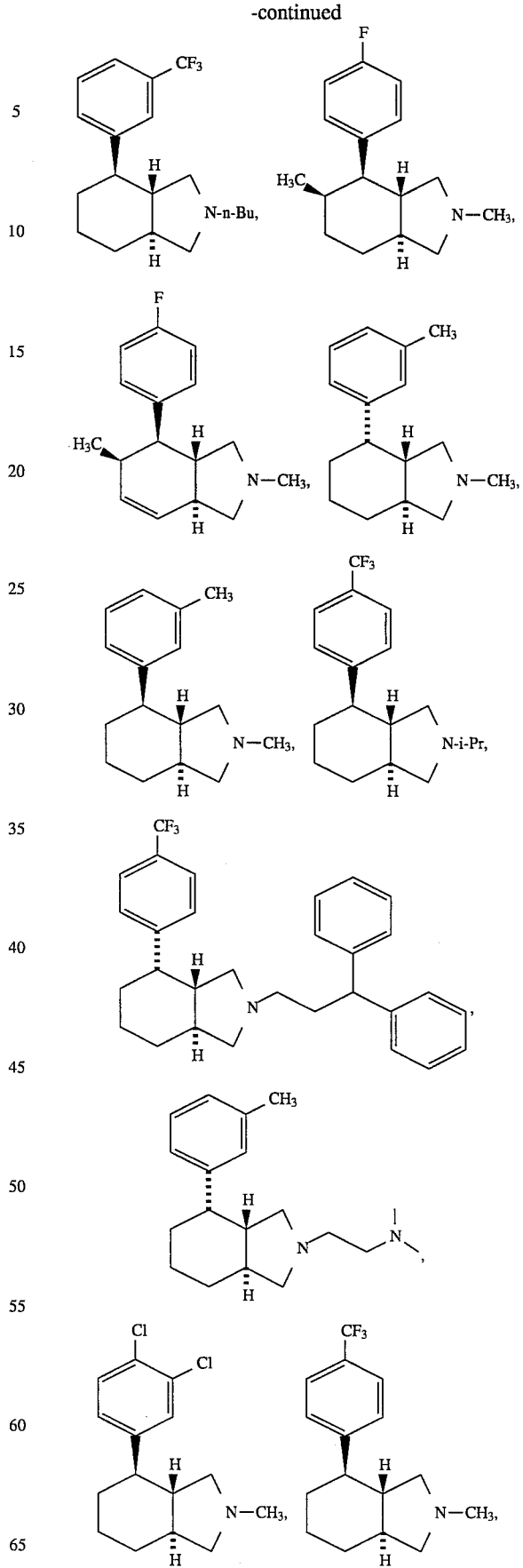

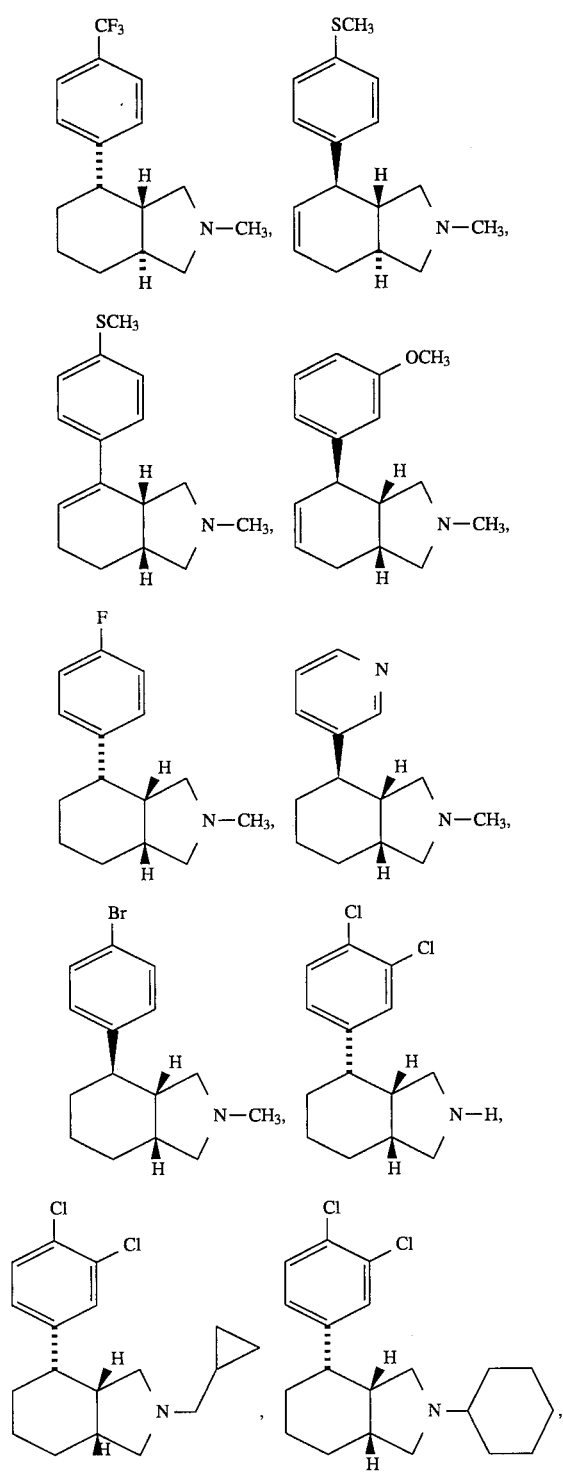
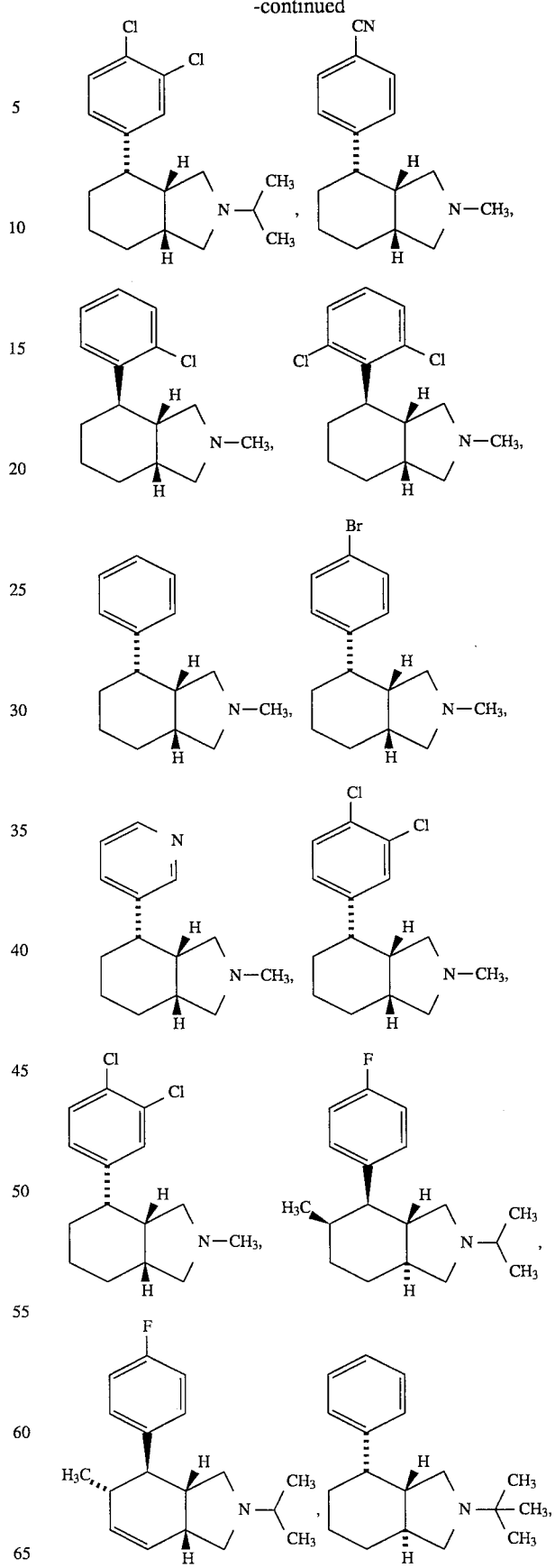

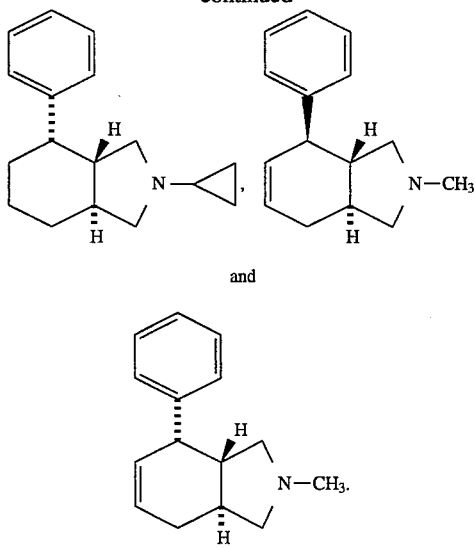

The activity of compounds of the invention as analgesics may be demonstrated by the mouse acetylcholine-bromide induced constriction assay as described below:

Mouse Acetylcholine Bromide-Induced Abdominal Constriction Assay

The mouse acetylcholine-induced abdominal constiction assay, as described by Collier et al. in Brit. J. Pharmacol. Chem. Ther., 32: 295–310, 1968, with minor modifications was used to assess analgesic potency of the compounds of formula (I). The test drugs or appropriate vehicle were administered orally (p.o.) and 30 minutes later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to a nociceptive stimulus (equated to % analgesia) was calculated as follows: The % Inhibition of response, i.e., % analgesia is equal to the difference between the No. of control animals response and the No. of drug-treated animals response times 100 divided by the No. of control animals responding.

At least 15 animals were used for control and in each of the drug treated groups. At least three doses were used to determine each dose response curve and $ED_{50}$ (that dose which would produce 50% analgesia). The $ED_{50}$ values and their 95% fiducial limits were determined by a computer assisted probit analysis.

TABLE I

| Mouse Acetylcholine-Bromide Induced Abdominal Constriction Assay | | |
|---|---|---|
| Compound Number | % Inhibition | $ED_{50}$ |
| Cp-1 | 30–40% @ 30 mpk/po | |
| Cp-2 | | 47.6 mpk/po |
| Cp-3 | | 22.1 mpk/po |
| Cp-4 | 60% @ 30 mpk/po | |
| Cp-5 | | 5.5 mpk/po |
| Cp-6 | 13.3% @ 30 mpk/po | |

TABLE I-continued

| Mouse Acetylcholine-Bromide Induced Abdominal Constriction Assay | | |
|---|---|---|
| Compound Number | % Inhibition | $ED_{50}$ |
| Cp-7 | | 7.46 mpk/po |
| Cp-8 | 78.8% @ 30 mpk/po | |
| CP-9 | | 3.8 mpk/po |
| Cp-10 | | 30 mpk/sc |
| Cp-11 | | 3 mpk/po |
| Cp-12 | | 6.26 mpk/po |
| Cp-13 | | 8.35 mpk/po |
| Cp-14 | | 2.8 mpk/po |
| Cp-15 | | 7.0 mpk/po |
| Cp-16 | | 4.6 mpk/po |
| Cp-17 | 33% @ 3 mpk/po | |
| Cp-18 | 66.7% @ 30 mpk/po | |
| Cp-19 | | 5.3 mpk/po |
| Cp-20 | | 5.4 mpk/po |
| Cp-21 | 100% @ 30 mpk/po | |
| Cp-22 | 13.3% @ 30 mpk/po | |
| Cp-24 | | 23.6 mpk/po |
| Cp-24+ | | 21.6 mpk/po |
| Cp-24- | | 24.9 mpk/po |
| Cp-25 | 67% @ 30 mpk/po | |
| Cp-28 | 0% @ 30 mpk/po | |
| Cp-31 | 20% @ 30 mpk/po | |
| Cp-32 | | 1.36 mpk/po |
| Cp-33 | | 10.5 mpk/po |
| Cp-34 | 100% @ 30 mpk/po | |
| Cp-35 | | 9.63 mpk/po |
| Cp-37 | | 2.0 mpk/po |
| Cp-38 | | 9.88 mpk/po |
| Cp-39 | | 1.79 mpk/po |
| Cp-40 | 1 00%@ 30 mpk/po | |
| Cp-41 | | 2.5 mpk/po |
| Cp-42 | 1 00%@ 30 mpk/po | |
| Cp-43 | | 4.9 mpk/po |
| Cp-44 | | 9.15 mpk/po |
| Cp-45 | 33%@ 30 mpk/po | |
| Cp-46 | 100%@ 30 mpk/po | |
| Cp-47 | | 4.0 mpk/po |
| Cp-48 | | 3.8 mpk/po |
| Cp-49 | | 4.3 mpk/po |
| Cp-50 | | 4.07 mpk/po |
| Cp-51 | | 15.6 mpk/po |
| Cp-52 | | 12.1 mpk/po |
| Cp-53 | | 10.1 mpk/po |

Based on the above results, invention compounds of formula (I) may be used to treat mild to moderately severe pain in warm-blooded animals such as humans in a manner similar to the use of meperidine hydrochloride by administration of an analgesically effective dose. The dosage range would be from about 10 to 3000 mg, in particular about 25 to 1000 mg or about 100 or 500 mg, of active ingredient 1 to 4 times per day for an average (70 kg) human although it is apparent that activity of individual compounds of the invention will vary as will the pain being treated. Pharmaceutical compositions of the invention comprise the formula (I) compounds as defined above, particularly in admixture with a pharmaceutically-acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intra muscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutically acceptable salts referred to above generally take a form in which the nitrogen of the core ring and/or possibly a nitrogen of a substituent is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

The following Examples illustrate the invention:

PROCEDURE A

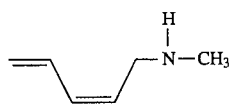
A

Pyridinium methiodide (22 g, 0.1 mol) was added to a suspension of lithium aluminum hydride (5.6 g, 0.15 mol) and tetrahydrofuran (400 mL). This mixture was heated at reflux for 16 h and cooled to room temperature. Successive portions of water (5.6 mL), 3N NaOH (16.8 mL) and water (5.6 mL) were added to the cooled mixture. The precipitate was filtered and washed with THF. The filtrate containing compound A, was dissolved in THF (1 L) and used without further purification (M. Fereles, et al. Coll. Czech Chem Comm, 1973, 38, 615–619).

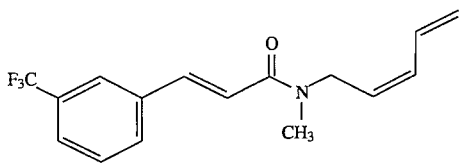
B m-Trifluoromethylcinnamoyl chloride (16.4 g, 69 mmol) was added to a stirred solution of 3N NaOH (50 mL, 150 mmol), ice/water (10 mL) and N-methyl-N-(2,4-pentadien-1-yl)amine/THF (ca. 50 mmol) and this mixture was stirred for 15 min. Ether was added to the resulting mixture and the aqueous layer was removed. The organic layer was washed with successive portions of aqueous dimethylaminopropylamine solution, dilute HCl, and brine; dried (MgSO$_4$), filtered, and concentrated in vacuo. The residue was purified by column chromatography on silica gel using acetone/hexane (15/85) as an eluent to give compound B, as an oil which crystallized upon standing.

$^1$H NMR (CDCl$_3$, 300 MHz): δ7.9-7.4 (m, 4H), 6.9-6.7 (m, 2H), 6.3 (t, 1H), 5.5-5.2 (m, 3H), 4.4-4.3 (doubled dd, 2H), 3.2-3.1 (doubled s, 3H).

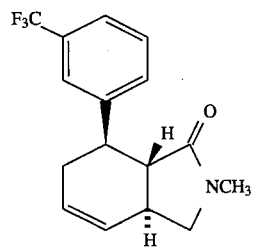
C

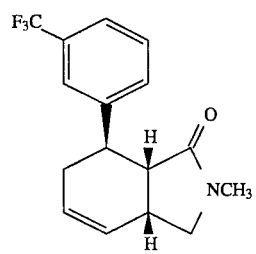
D

A solution of the amide B (4.6 g, 15.57 mmol) in toluene was heated at reflux for 16 h and concentrated in vacuo. The resulting mixture was separated by column chromatography (Waters Prep 500: acetone/hexane, 20/80 as eluent) and the isolated components were recrystallized from hexane to give diastereomers C and D.

Compound C $^1$H NMR (CDCl$_3$, 300 MHz): δ7.5-7.4 (m, 4H), 5.9 (d, 1H), 5.65 (m, 1H), 3.3 (m, 1H), 3.2 (m, 1H), 2.8 (s, 3H), 2.9-2.75 (m,1H), 2.6 (m, 2H), 2.2 (m, 1H). Anal. Calc'd for C$_{16}$H$_{16}$F$_3$NO: C, 65.07; H, 5.46; N, 4.74 Found: C, 65.23; H, 5.32; N, 4.67

Compound D $^1$H NMR (CDCl$_3$, 300 MHz): δ7.55 (s, 1H), 7.5-7.3 (m, 3H), 6.0 (m, 1H), 5.65 (d, 1H), 3.6 (m, 1H), 3.5 (m, 1H), 3.07 (d, 1H), 2.87 (s, 3H), 2.77 (s, 2H), 2.5 (m, 1H), 2.2 (m, 1H). Anal. Calc'd for C$_{16}$H$_{16}$F$_3$NO: C, 65.07; H, 5.46; N, 4.74 Found: C, 65.05; H, 5.31; N, 4.65.

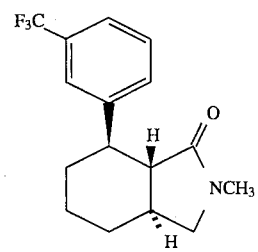
E

10 % Pd/C (45 mg) was added to a solution of compound C (0.45 g, 1.5 mmol) in EtOH (20 mL) and the resulting mixture was pressurized with H$_2$ (35 psi) for 16 h. The mixture was filtered and concentrated in vacuo to give compound E, as an oil which was used without further purification.

$^1$H NMR (CDCl$_3$, 300 MHz): δ7.5-7.4 (m, 4H), 6.0 (m, 1H), 3.25 (m, 1H), 3.1 (t, 1H), 2.75 (s, 3H), 2.8-2.7 (m, 1H), 2.2 (m, 1H), 2.0 (m, 4H), 1.5-1.3 (m, 4H). Anal. Calc'd for C$_{16}$H$_{18}$F$_3$NO: C, 64.63; H, 6.10; N, 4.71 Found: C, 64.26; H, 6.02; N, 4.67

EXAMPLE 1

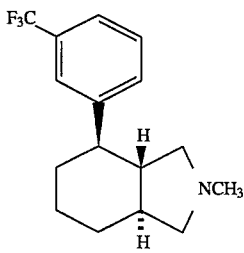

Cp-7

3aα,4α,7aβ-Octahydro-2-methyl-4-(3-trifluoromethylphenyl)-1H-isoindole Monofumarate 1M Borane/THF complex (4 mL, 4 mmol) was added to a solution of compound E (0.4 g, 1.3 mmol) in THF (5 mL). This mixture was heated at reflux for 16 h under Ar and cooled to room temperature. A portion of water (25 mL) was added and the organic solvent was removed in vacuo. Propionic acid (3 mL) was added and the resulting mixture was heated on a steam bath for 4 h, poured into aqueous NaOH and extracted with methylene chloride. The combined organic extracts were dried ($K_2CO_3$), concentrated in vacuo and combined with fumaric acid (0.15 g). This mixture was dissolved in hot isopropanol and a portion of ether was added. The resulting precipitate was isolated from the solution to give the title compound as a solid: mp 152°–154° C.

$^1$H NMR (DMSO $d_6$, 300 MHz): δ7.6 (m, 4H), 6.47 (s, 2H), 3.34 (m, 1H), 2.9-2.65 (m, 4H), 2.64 (s, 3H), 2.1 (m, 1H), 1.95-1.75 (m, 4H), 1.5 (m,0.2H), 1.2 (m, 1H) Anal. Calc'd for $C_{16}H_{20}F_3N \cdot C_4H_4O_4$: C, 60.14; H, 6.06; N, 3.51 Found: C, 60.09; H, 6.04; N, 3.43

PROCEDURE B

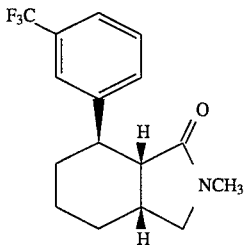

F

10% Pd/C (0.24 g) was added to a solution of compound D (2.40 g, 8.07 mmol) in EtOH (50 mL) and the resulting mixture was pressurized with $H_2$ (50 psi) for 1 h. The mixture was filtered and concentrated in vacuo to give compound F as an oil which crystallized upon standing.

$^1$H NMR (CDCl$_3$, 300 MHz): δ7.5 (s, 1H), 7.45 (m, 3H), 3.45 (m, 1H), 3.3 (dd, 1H), 3.05 (dd, 1H), 2.9 (bs, 3H), 1.9-1.63 (m, 3H), 1.4 (m, 3H). Anal. Calc'd for $C_{16}H_{18}F_3NO$: C, 64.63; H, 6.10; N, 4.71 Found: C, 64.91; H, 6.02; N, 4.66

EXAMPLE 2

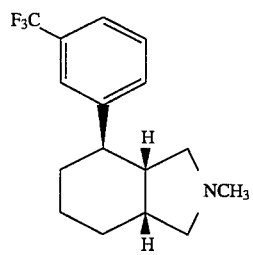

Cp-5

3aα,4α,7aα-Octahydro-2-methyl-4-(3-trifluoromethylphenyl)-1H-isoindole Monofumarate 1M Borane/THF complex (21 mL, 21 mmol) was added to a solution of compound F (2.1 g, 7.1 mmol) in THF (20 mL) and this mixture was heated to reflux for 16 hr under Ar and cooled to room temperature. A portion of water (1.4 mL) was added and the organic solvent was removed in vacuo. Propionic acid (5.6 mL) was added and the resulting mixture was heated on a steam bath for 3 h, poured into dilute aqueous NaOH and extracted with ether. The organic layer was washed with dilute HCl and the resulting aqueous layer was made basic with NaOH and extracted with methylene chloride. The combined organic extracts were dried ($K_2CO_3$), concentrated in vacuo and combined with fumaric acid (0.51 g). This mixture was dissolved in isopropanol and the resulting precipitate was isolated from the solution to give the title compound as a solid: mp 152°–154° C.

$^1$NMR (DMSO $d_6$, 300 MHz): δ7.65-7.5 (m, 4H), 6.5 (s, 2H), 3.37 (t, 1H), 3.05 (t, 1H), 2.9-2.7 (m, 3H), 2.63 (s, 3H), 2.4 (m, 4H), 1.5 (m,0.1H), 1.72-1.43 (m, 6H). Anal. Calc'd for $C_{16}H_{20}F_3N \cdot C_4H_4O_4$: C, 60.14; H, 6.06; N, 3.51 Found: C, 60.25; H, 5.98; N, 3.42

PROCEDURE C

The following general procedure was used to synthesize the compounds listed in Table 1.

An appropriately substituted cinnamoyl chloride derivative (10.0 mmol) was added to a stirred solution of 3N NaOH (21.74 mmol), ice/water (1.4 mL) and N-methyl-N-(2,4-pentadien-1-yl) amine/THF (ca. 7.25 mmol) and this mixture was stirred for 15°30 min. A suitable organic solvent such as ether was added to the resulting mixture and the aqueous layer was removed. The organic layer was washed with successive portions of an N,N-dialkylaminoalkylamine solution such as dimethylaminopropylamine solution, an acidic solution such as HCl and brine; dried (MgSO$_4$), filtered, and concentrated in vacuo. The residue was purified using any of the standard techniques which include column chromatography and recrystallization to give the coupled amide derivative AA4. A solution of the amide derivative AA4 (10.0 mmol) in a suitable organic solvent such as toluene was heated at reflux for 16–36 h and concentrated in vacuo. The resulting residue was purified by any of the standard methods which include column chromatography and recrystallization to give the cyclized derivatives AA5 and AA6. A catalytic portion of 10% Pd/C was added to a solution of an appropriately substituted derivative AA6 (10.0 mmol) in a suitable solvent such as EtOH (132 mL) and the resulting mixture was pressurized with $H_2$ (at approximately 35 psi) for 16 h. The mixture was filtered and concentrated in vacuo to give the saturated derivative, which was used without further purification.

1M Borane/THF complex (29.0 mmol) was added to a solution of the saturated derivative (10.0 mmol) in THF (28 mL). This mixture was heated to reflux for 16 h under Ar and cooled. A portion of water (1.97 mL) was added and the organic solvent was removed in vacuo. Propionic acid (7.88 mL) was added and the resulting mixture was heated on a steam bath for 3 h, poured into NaOH aq. and extracted with a suitable organic solvent such as ether. The organic layer was washed with HCl aq. and the resulting aqueous layer was made basic with NaOH and extracted with a suitable organic solvent. The combined organic extracts were dried and concentrated in vacuo. The residue was dissolved a suitable solvent, treated with an appropriate organic or mineral acid and crystallized from this mixture to give the desired derivative 3.

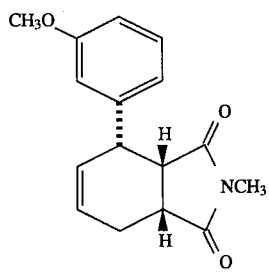

H

A suspension of diene G (50 g, 0.31 mol), N-methylmaleimide (35 g, 0,31 mol) and water (500 mL) was stirred in a Morton flask for 16 h under Ar and extracted with methylene chloride. The combined organic extracts were washed with brine, dried ($MgSO_4$) and concentrated in vacuo. The residue was purified by column chromatography using hexane/acetone (5/1) as an eluent to give the coupled product H as an oil: MS 271.

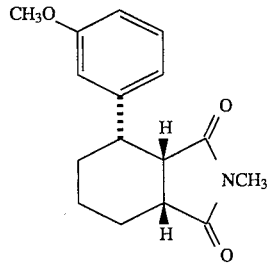

I

A suspension of the coupled product H (17.0 g, 62.7 mmol), 10% Pd/C (1.7 g) and ethyl acetate (200 mL) was placed in a Parr bottle and pressurized with $H_2$ for 3 h. The catalyst was filtered and the filtrate was concentrated in vacuo to give the saturated product I as an oil.

$^1$H NMR (CDCl$_3$, 300 MHz): δ7.5 (t, 1H), 6.9-6.8 (m, 3H), 3.8 (s, 3H), 3.3 (m, 1H), 3.1-3.0 (m, 2H), 2.9 (s, 3H), 2.15 (m, 1H), 1.95 (m, 1H), 1.8-1.5 (m, 4H).

TABLE 1

| Cp-n | $(R^a)_n$ | $R^c$ | mp °C. | C | H | N | Empirical Formula | MS (MH$^+$) |
|---|---|---|---|---|---|---|---|---|
| Cp-1 | 3-OMe | Me | 111–3 | 66.30 | 7.43 | 3.81 | $C_{16}H_{23}NO \cdot C_4H_4O_4$ | 246 |
| Cp-8 | 2,3-di-OMe | Me | 154–6 | 62.24 | 7.55 | 3.78 | $C_{17}H_{25}NO_2 \cdot C_2H_2O_4$ | 276 |
| Cp-9 | 3,4-di-Cl | Me | 176–8 | 57.46 | 5.95 | 3.45 | $C_{16}H_{23}NO \cdot C_4H_4O_4 \cdot \frac{1}{8} C_2H_8O$ | 285 |

PROCEDURE D

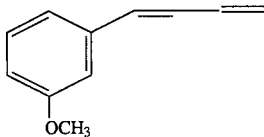

G

Allyltriphenylphosphonium bromide (300 g, 0.78 mol) was added portionwise under Ar to a cooled solution of sodium bis(trimethylsilyl)amide (1.0 mol/THF: 776 mL, 0.78 mol) and THF (1 L). The resulting mixture was stirred for another 30 min and a solution of 3-methoxybenzaldehyde (97 g, 0.71 mol) in THF was added to the mixture over 1.5 h. The reaction mixture was stirred for 2 h and poured into ice/water. The organic layer was removed and the resulting aqueous layer was washed with several portions of ether. The combined organic layers were washed with brine, dried ($MgSO_4$) and concentrated in vacuo. The residue was dissolved in t-butylmethylether and the resulting precipitate (triphenylphosphine oxide) was removed by filtration. The filtrate was treated in the same manner several times until most of the triphenylphosphine oxide was removed. The resulting residue was purified by column chromatography on silica gel using hexane/acetone, (10/1) as an eluent to give the diene G, as an oil.

EXAMPLE 3

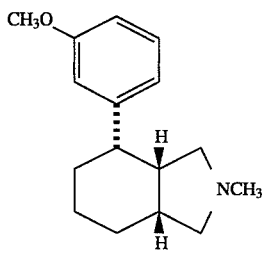

Cp-3

3aα,4β,7aα-Octahydro-1-methyl-4-(3-methoxyphenyl)-
1H-isoindole Monooxalate 0.2 Hydrate 1M Borane/THF (180 mL, 0.18 mol) was added dropwise to a solution of the saturated product I (8 g, 29 mmol) in THF (85 mL) and the reaction mixture was heated to reflux for 16 h. Propionic acid (561 mL, 7.52 mol) was added and the resulting mixture was heated at reflux for another 3 h. The resulting mixture was cooled to room temperature, basified with NaOH and extracted with several portions of ether. The combined organic extracts were washed with water followed by brine, dried ($K_2CO_3$) and concentrated in vacuo. The residue was treated with another portion of propionic acid (300 ML, 4 mol) at reflux for 8 h followed by the standard work-up described above. The resulting residue was purified by column chromatography on silica gel using methylene chloride/methanol/ammonium hydroxide (90/10/1) as an eluent to give the free base of the title compound as an oil. Treatment of this base with oxalic acid followed by recrystallization with isopropanol gives the title compound as a solid: mp 121°–124° C.

Anal. Calc'd for $C_{16}H_{23}NO \cdot C_2H_2O_4 \cdot 0.2\ H_2O$: C, 63.77; H, 7.55; N, 4.31 Found: C, 63.84; H, 7.57; N, 4.12

EXAMPLE 4

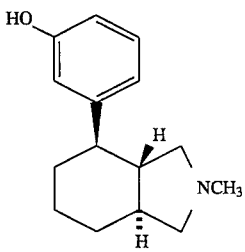

Cp-10

3aα,4α,7aβ-Octahydro-2-methyl-4-(3-hydroxyphenyl)-
1H-isoindole Hemifumarate

A mixture of 3aα, 4α, 7aβ-octahydro-2-methyl-4-(3-methoxyphenyl)-1H-isoindole (2.0 g, 8.1 mmol) and 48% HBr (40 mL) was heated at reflux for 4 h and concentrated in vacuo. The residue was washed with ether, dissolved in isopropanol, treated with enough ether to cloud the clear solution and placed in the freezer for 16 h. The resulting suspension was concentrated in vacuo and partitioned between $NaHCO_3$ aq. and methylene chloride. The organic layer was concentrated in vacuo and the resulting residue was treated with fumaric acid, isopropanol and ether. The title compound was isolated from this mixture as a tan solid: mp 224° C. dec, Exact Mass: Calc'd 231.16231 Found 231.1664.

PROCEDURE E

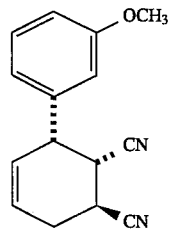

J

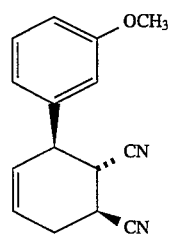

K

A mixture of cis-diene G (17.4 g, 0.11 mol), fumaronitrile (8.3 g, 0.11 mol), hydroquinone (0.1 g) and toluene was heated in a closed system at 125° C. for 16 h and concentrated in vacuo. The residue was recrystallized from hexane/ethyl acetate and the first crop of crystals was recrystallized from the same solvent mixture to give compound K as a solid: mp 133°–135° C. The first mother liquor was concentrated in vacuo and purified by a combination of bulb to bulb distillation (at 100° C. and 0.001 mm Hg) and successive recrystallizations from ethyl acetate/hexane to give compound J as a solid: mp 96°–99° C.

Compound J:

$^1$H NMR ($CDCl_3$, 300 MHz): δ7.37-7.27 (m, 1H), 6.95-6.85 (m, 3H), 6.0 (m, 1H), 6.1 (m, 1H), 3.85 (s, 3H), 3.4 (t, 1H), 3.3 (q, 1H), 2.9-2.8 (m, 1H), 2.65 (m, 1H).

Compound K:

$^1$H NMR ($CDCl_3$, 300 MHz): δ7.3 (m, 1H), 6.85 (m, 3H), 5.9 (m, 1H), 5.7 (m, 1H), 3.8 (m, 1H), 3.6 (m, 1H), 3.2 (m, 1H), 2.9 (t, 1H), 2.7-2.65 (t, 1H), 2.65 (m, 1H).

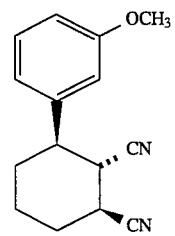

L

A mixture of compound K (20.0 g, 0.08 mol), 10% Pd/C (2.0 g) and ethyl acetate (200 mL) was placed in a Parr bottle and pressurized for 4 h under $H_2$. The catalyst was filtered and the mother liquor was concentrated in vacuo. The residue was purified by a combination of techniques which include recrystallization from methylcyclohexane/ethyl acetate and column chromatography on silica gel using hexane/acetone (5/1) to give the saturated compound L as a solid: mp 80°–82° C.

Anal. Calc'd for $C_{15}H_{16}N_2O$: C, 74.97; H, 6.71; N, 11.66 Found: C, 75.16; H, 6.60; N, 11.42

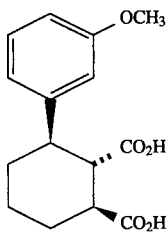

M

A mixture of the saturated compound L (5.0 g, 20.8 mmol), water (20 mL), 85% $H_3PO_4$ and glyme (5 mL) was heated at reflux for 50 h and stirred at room temperature for 72 h. The resulting mixture was poured into ice/water and extracted with ether/THF. The combined organic layers were washed with water, and brine, dried ($MgSO_4$) and concentrated in vacuo. The residue was purified by recrystallization from methylcyclohexane/ethyl acetate (96/2) to give the saturated diacid M as a solid: mp 194°–196° C.

Anal. Calc'd for $C_{15}H_{18}O_5$: C, 64.74; H, 6.52 Found: C, 64.61; H, 6.58

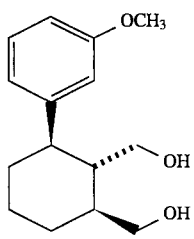

N 1.0M Borane/THF (231 mL, 0.231 mol) was added dropwise to a solution of the diacid M (12.4 g, 44.6 mmol) in THF (80 mL) and the resulting mixture was stirred for 16 h at room temperature under Ar. Water (170 mL) was added to the reaction mixture followed by several washes with ether. The combined organic extracts were washed with water and brine, dried ($MgSO_4$) and concentrated in vacuo. The residue was dissolved in THF (120 mL), another portion of 1.0M Borane/THF (115 mL, 0.115 mol) was added and the reaction was stirred at room temperature for another 16 h. The resulting mixture was worked-up as previously mentioned, and recrystallized from methylcyclohexane/ethyl acetate to give the diol intermediate N as a solid: mp 97°–98° C.

Anal. Calc'd for $C_{16}H_{23}NO \cdot C_2H_2O_4 \cdot 0.2\ H_2O$: C, 71.97; H, 8.86 Found: C, 71.94; H, 8.89

EXAMPLE 5

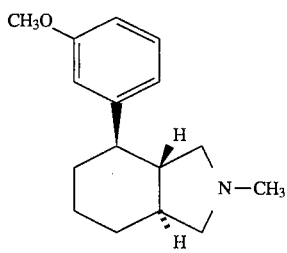

Cp-2

3aα,4α,7aβ-Octahydro-2-methyl-4-(3-methoxyphenyl)-1H-isoindole Monofumarate 0.1 Hydrate A solution of methanesulfonyl chloride (6.1 mL, 0.08 mol) in methylene chloride (6 mL) was added dropwise to a solution of the diol intermediate N (5 g, 0.02 mol) and triethylamine (13 mL, 0.1 mol) in methylene chloride at 0° C. and stirred for 2.5 h. The reaction mixture was poured into aqueous $NaHCO_3$ and the organic layer was extracted with brine, dried ($MgSO_4$) and concentrated in vacuo. The resulting residue and KI (7.3 g, 0.44 mol) were dissolved in DMF (60 mL), heated to 60° C. for 2 h, cooled to room temperature and transferred to a pressure bottle. Monomethylamine (g) was bubbled into the vessel over 5 min and the resulting mixture was heated at 60° C. for 16 h. This mixture was poured into water and extracted with ethyl acetate. The combined organic extracts were washed with water and brine, dried ($K_2CO_3$) and concentrated in vacuo. The residue was dissolved in ether/isopropanol and the precipitate was removed by filtration. The filtrate was concentrated in vacuo, and purified by chromatography (Waters Prep 500:silica gel, methylene chloride/methanol (90/10) to methylene chloride/methanol:ammonium hydroxide (90/9.5/0.5)) and crystallization from fumaric acid and isopropanol/EtOH to give the title compound as a solid: mp 182°–189° C.

Anal. Calc'd for $C_{16}H_{23}NO \cdot C_4H_4O_4 \cdot 0.1\ H_2O$: C, 66.13; H, 7.55; N, 3.86 Found: C, 65.98; H, 7.66; N, 3.81

PROCEDURE F

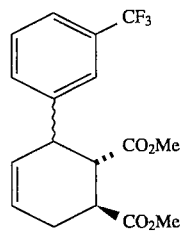

O

A mixture of 1-(3-trifluoromethylphenyl)-1,3-butadiene (10 g, 0.05 mol), dimethyl fumarate (7.2 g, 0.05 mol) and ethylene glycol was heated at 60° C. for 16 h. The reaction mixture was poured into water and extracted with ether. The combined organic extracts were washed with water and brine, dried ($MgSO_4$) and concentrated in vacuo. The residue was purified by crystallization from methylcyclohexane/ethyl acetate (which removed the unreacted dimethyl fumarate), bulb to bulb distillation of the mother liquor (at 0.001 mm Hg and 150°–160° C.) and column chromatography on silica gel using hexane as an eluent to give the desired diester diastereomer intermediates O as an oil.

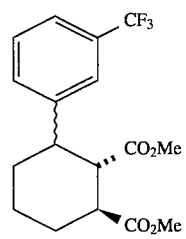

P

A mixture of the diester diastereomers O (41.05 g, 0.12 mol), ethyl acetate (400 mL) and 10% Pd/C (4.2 g) was placed on a Parr shaker and pressurized with $H_2$ for 2 h. The catalyst was removed by filtration and the filtrate was concentrated in vacuo to give the saturated diester diastereomer intermediates P as an oil.

Anal. Calc'd for $C_{17}H_{19}F_3O_4$: C, 59.30; H, 5.56 Found: C, 50.06; H, 5.60

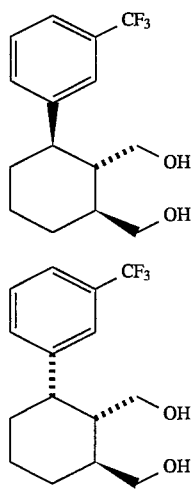

Q

R

A solution of the diester diastereomer derivatives P (40.1 g, 0.116 mol) in ether (300 mL) was added dropwise to a cooled suspension of LAH (22.15 g, 0.58 mol) and ether (300 mL) under Ar. This mixture was stirred overnight at room temperature. Water (22 mL), followed by 3N NaOH (66 mL) further followed by water (22 mL) were added dropwise and the reaction mixture was stirred for 20 min. The resulting solid precipitate was filtered and the filtrate was washed with successive portions of ether and methylene chloride. The combined organic extracts were concentrated in vacuo, dissolved in methylene chloride, dried ($MgSO_4$) and concentrated in vacuo. The residue was recrystallized from methylcyclohexane/ethyl acetate to give compound R as a solid. The mother liquor was purified by column chromatography (Water's Prep 500: methylene chloride/ MeOH (20/1)) to give the separated diastereomers Q, as an oil, and R.

Compound Q:

$^1$H NMR ($CDCl_3$, 300 MHz): δ7.5-7.3 (m, 4H), 3.8-3.45 (m, 4H), 3.4-3.0 (m, 2H), 2.6-2.45 (m, 1H), 1.95-1.7 (m, 3H), 1.65-1.35 (m, 2H), 1.3-1.15 (m, 1H). Anal. Calc'd for $C_{15}H_{19}F_3O_2$: C, 62.49; H, 6.64 Found: C, 62.25; H, 6.70;

Compound R:

$^1$H NMR ($CDCl_3$, 300 MHz): δ7.45-7.3 (m, 4H), 3.65 (d, 2H), 3.45 (t, 1H), 3.05 (m, 1H), 2.95-1.7 (dd, 1H), 2.1 (m, 1H), 1.9 (m, 1H), 1.85-1.65 (m, 3H), 1.62-1.4 (m, 3H).

EXAMPLE 6

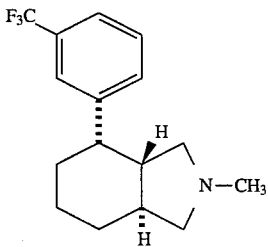

Cp-11

3aα, 4β,
7aβ-Octahydro-2-methyl-4-(3-trifluoromethylphenyl)-
1H-isoindole Monofumarate A solution of methanesulfonyl chloride (3.24 mL, 0.04 mol) in methylene chloride (10 mL) was added dropwise to a solution of the diol intermediate R (3 g, 0.01 mol) and triethylamine (7.2 mL, 0.05 mol) in methylene chloride at 0° C. and the reaction mixture was stirred for 1.5 h at 0° C. The reaction mixture was poured into $NaHCO_3$ aq. and the resulting organic layer was extracted with brine, dried ($Na_2SO_4$) and concentrated in vacuo. The residue and KI (3.84 g, 0.022 mol) were dissolved in DMF (45 mL), heated to 55° C. for 2 h, cooled to room temperature and transferred to a pressure bottle. Monomethyl amine (g) was bubbled into the vessel and the resulting mixture was heated at 60° C. for 16 h. This mixture was poured into water and extracted with ether. The combined organic extracts were washed with water and brine, dried ($K_2CO_3$) and concentrated in vacuo. The residue was concentrated in vacuo, treated with fumaric acid and crystallized from isopropanol to give the title compound as a solid: mp 178°– 180° C.

Anal. Calc'd for $C_{16}H_{20}NF_3 \cdot C_4H_4O_4$: C, 60.14; H, 6.06; N, 3.51 Found: C, 60.35; H, 6.18; N, 3.41

The following general procedure was used to synthesize the compounds listed in Table 2.

PROCEDURE G

A solution of methanesulfonyl chloride (0.04 mol) in methylene chloride (10 mL) was added dropwise to a solution of the appropriately substituted diol diastereomer AD5 or AD6 (0.01 mol) and triethylamine (0.05 mol) in methylene chloride at 0° C. and the reaction mixture was stirred for 1–3 h at 0° C. The reaction mixture was poured into aqueous $NaHCO_3$ and the resulting organic layer was extracted with brine, dried ($Na_2SO_4$ or $MgSO_4$) and concentrated in vacuo. The residue and KI (0.022 mol) were dissolved in DMF (45–65 mL), heated to 55° C. for 2 h, cooled to room temperature and transferred to a reaction vessel. An appropriately substituted primary amine (0.010–0.10 mol) was added and the resulting mixture was heated at 50°–70° C. for 2–16 h. This mixture was poured into water and extracted with a suitable organic solvent such as ether. The combined organic extracts were washed with water and brine, dried ($Na_2SO_4$ or $MgSO_4$) and concentrated in vacuo. The residue was concentrated in vacuo, treated with any suitable mineral or organic acid and recrystallized from any appropriate solvent to give the desired compounds.

TABLE 2

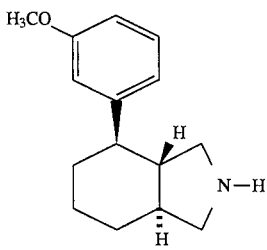

| Cp-n | (R$^a$)$_n$ | R$^c$ | mp °C. | C | H | N | Empirical Formula | MS (MH$^+$) |
|---|---|---|---|---|---|---|---|---|
| Cp-7 | 3-CF$_3$ | CH$_3$ | 152–54 | 60.09 | 6.04 | 3.43 | C$_{16}$H$_{20}$F$_3$N.C$_4$H$_4$O$_4$ | 284 |
| Cp-6 | 3-OMe | Bzl | 180–81 | 70.96 | 7.17 | 3.19 | C$_{22}$H$_{27}$NO.C$_4$H$_4$O$_4$ | 321 |

The compound of Table 3 is made by procedure G

TABLE 3

| Cp-n | (R$^a$)$_n$ | R$^c$ | mp °C. | C | H | N | Empirical Formula | MS (MH$^+$) |
|---|---|---|---|---|---|---|---|---|
| Cp-29 | 3-OMe | Bzl | 180 est. | — | — | — | C$_{22}$H$_{27}$NO.C$_4$H$_4$O$_4$ | — |

EXAMPLE 7

Cp-4

3aα,4α,7aβ-Octahydro-4-(3-methoxyphenyl)-1H-isoindole Monooxalate

ACE-Cl (0.85 mL, 0.018 mmol) was added dropwise to a cooled solution of 3aα, 4α, 7aβ-octahydro-4-(3-methoxyphenyl)-2-phenylmethyl-1H-isoindole (1.9 g, 0.006 mol) in 1,2-dichloroethane (25 mL). The resulting reaction mixture was heated at reflux for 2 h and left at RT for 16 h. ACE-Cl (0.8 mL) and triethylamine (0.8 mL, 0.006 mmol) were added and the resulting reaction mixture was heated at reflux for another 2 h and concentrated in vacuo. The residue was dissolved in MeOH, heated to reflux for 3 h and concentrated in vacuo. This substance was purified by column chromatography using silica gel and methylene chloride/MeOH/NH$_4$OH (80/20/1) as an eluent. The resulting product was dissolved in 2-PrOH and ethereal HCl added. The solid which resulted (Et$_3$N-HCl) was filtered off. The filtrate was concentrated and converted to the free base by partitioning between Et$_2$O and 3N NaOH. The free base was treated with oxalic acid in EtOH. The desired salt crystallized from this mixture as an off white solid: mp 143°–145° C.

Anal. Calc'd for C$_{15}$H$_{21}$NO.C$_2$H$_2$O$_4$: C, 63.54; H, 7.21; N, 4.36 Found: C, 63.21; H, 7.12; N, 4.30

PROCEDURE H

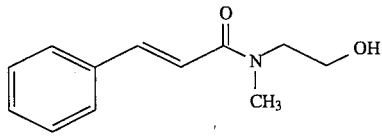

S

A solution of cinnamoyl chloride (47 g, 0.28 mol) in methylene chloride (100 mL) was rapidly added to a stirred mixture of methylaminoethanol (24.7 mL, 30 mol), methylene chloride (320 mL), 3N NaOH (180 mL, 0.54 mol) and ice/water 70 mL). The resulting mixture was stirred for 1 h and the aqueous layer was removed. The organic layer was washed with successive portions of dilute HCl and brine, dried (MgSO$_4$) and concentrated in vacuo. The residue was recrystallized from t-butyl methyl ether to give compound S as a solid.

Anal. Calc'd for $C_{12}H_{15}NO_2$: C, 70.22; H, 7.37; N, 6.82 Found: C, 70.21; H, 7.42; N, 6.88

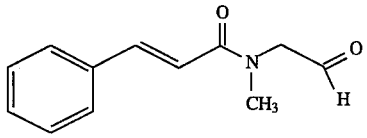
T

A solution of DMSO (18 mL, 0.26 mol) in methylene chloride (80 mL) was added to a stirred solution of oxalyl chloride (12.6 mL, 0.13 mol) in methylene chloride (150 mL) at −50° to −60° C. under Ar over 5 min. The reaction temperature was maintained at a −50° to −60° C. during the addition of a solution of compound S (27.02 g, 0.13 mol) in methylene chloride (150 mL) and 25 min of stirring followed by an addition of triethylamine (91 mL, 0.66 mol). The reaction mixture was allowed to warm to room temperature and water (150 mL) was added. The resulting organic layer was separated, washed with successive portions of dilute HCl, aqueous $NaHCO_3$, and brine; dried ($MgSO_4$), and concentrated in vacuo to give compound T as an oil.

$^1$H NMR (CDCl$_3$, 300 MHz): δ9.7 (s, 1H), 7.8-7.2 (d, 1H), 7.6-7.45 (m, 2H), 7.45-7.3 (m, 3H), 6.97-6.92 (d, 1H), 4.3 (s, 2H), 3.25 (s, 3H).

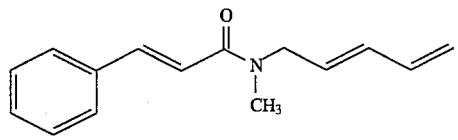
U

Allyltriphenylphosphonium bromide (88.1 g, 0.23 mol) was added portionwise to a cooled solution of sodium bis(trimethylsilyl)amide (1M/THF: 230 mL, 0.23 mol) and THF (290 mL) under Ar over 45 m. The mixture was stirred for 30 min and a solution of compound T (42.8 g, 0.21 mol) in THF (120 mL) was added dropwise over 1 h. The resulting mixture was poured into ice and extracted with several portions of ether. The combined organic extracts were washed with successive portions of water and brine, dried (MgSO$_4$) and concentrated in vacuo. The residue was purified by crystallization from t-butyl methyl ether and column chromatography on silica gel using hexane/acetone (3/1) as an eluent to give compound U.

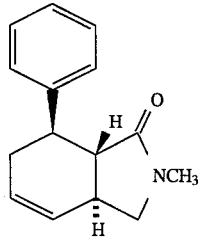
V

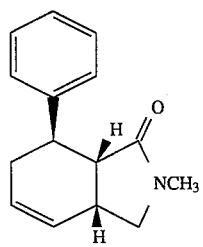
W

A solution of the amide U (6.85 g, 30.12 mmol) in toluene (250 mL) was heated at reflux for 16 h and concentrated in vacuo. The resulting mixture was purified by column chromatography (Waters Prep 500: acetone/hexane (1/3) eluent) followed by recrystallization of the isolated components from hexane to give diastereomers V and W.

Compound V:
$^1$H NMR (CDCl$_3$, 300 MHz): δ7.3-7.2 (m, 5H), 7.45-7.3 (m, 3H), 5.9 (m, 1H), 5.85 (m, 1H), 3.5 (m, 1H), 3.1 (m, 2H), 2.9-2.7 (m, 1H), 2.8 (s, 3H), 2.65-2.45 (m, 2H), 2.3-2.15 (m, 1H).

Compound W:
$^1$H NMR (CDCl$_3$, 300 MHz): δ7.4-7.15 (m, 5H), 5.95 (m, 1H), 5.65 (m, 1H), 3.55 (m, 2H), 3.05 (d, 1H), 2.9 (s, 3H), 2.75 (bs, 1H), 2.5-2.4 (m, 1H), 2.3-2.15 (m, 2H).

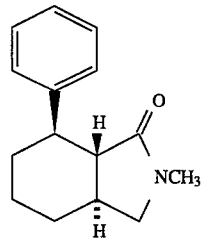
X

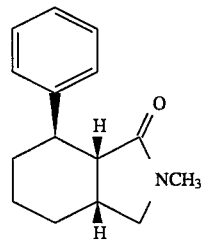
Y

Compounds X and Y were prepared substantially as described in Procedure B, using V or W in place of compound F to give the corresponding saturated product.

Compound X:
$^1$H NMR (CDCl$_3$, 300 MHz): δ7.35.7.25 (m, 3H), 7.22-7.1 (m, 2H), 3.45-3.35 (m, 1H), 3.32-3.20 (m, 1H), 3.10-3.0 (m, 1H), 2.9 (s, 3H), 2.7 (m, 2H), 1.85-1.6 (m, 3H), 1.45-1.3 (m, 3H).

Compound Y:
$^1$H NMR (CDCl$_3$, 300 MHz): δ7.35.7.1 (m, 5H), 3.3-3.2 (m, 1H), 3.1-3.02 (t, 1H), 2.9-2.85 (d, 1H), 2.75 (s, 3H), 2.7-2.55 (m, 1H), 2.05-1.9 (m, 3H), 1.5-1.1 (m, 4H).

EXAMPLE 8

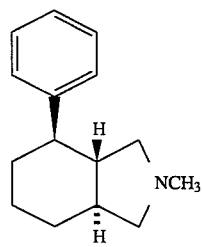
Cp-13

3aα,4α,7aβ-Octahydro-2-methyl-4-phenyl-1H-isoindole Monofumarate

The title compound was prepared substantially as described in Example 1 using compound X in place of compound E: mp 144°–146° C.

Anal. Calc'd for $C_{15}H_{21}N.C_4H_4O_4$: C, 68.86; H, 7.60; N, 4.23 Found: C, 68.59; H, 7.56; N, 4.22

EXAMPLE 9

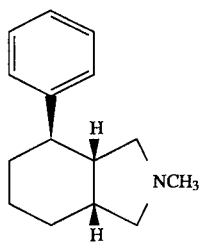
Cp-12

3aα,4α,7aβ-Octahydro-2-methyl-4-phenyl-1H-isoindole Monofumarate

The title compound was prepared substantially as described in Example 1 using compound Y in place of compound E: mp 166°–167° C.

Anal. Calc'd for $C_{15}H_{21}N \cdot C_4H_4O_4$: C, 68.86; H, 7.60; N, 4.23 Found: C, 68.62; H, 7.59; N, 4.19

PROCEDURE I

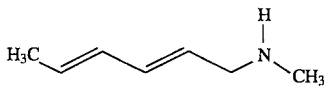
Z

Hexadienal (2.6 g, 27 mmol) was added to a stirred solution of methyl amine (4.23 g, 0.136 mol) and methylamine hydrochloride (9.18 g, 0.136 mol) in methanol (75 mL). The reaction was stirred for 15 min followed by an addition of sodium cyanoborohydride (2.06 g, 32.6 mmol) and another hour of stirring. The pH of the reaction mixture was adjusted to pH 7 by the addition of acetic acid and this mixture was stirred for another 4 h. The resulting mixture was acidified with HCl, stirred for 30 min, basified with NaOH and extracted with methylene chloride. The combined organic extracts were dried ($K_2CO_3$) and concentrated in vacuo to give compound Z as an oil.

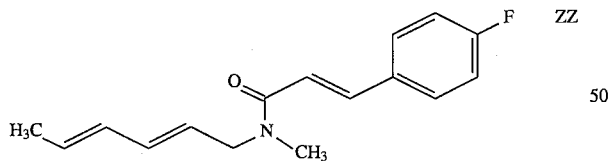
ZZ

4-Fluorocinnamoyl chloride (3.7 g, 15.0 mmol) was added to a mixture of compound Z (1.7 g, 15.0 mmol), methylene chloride (50 mL) and 3N NaOH (20 mL) and the reaction mixture was stirred for 1 h. The organic layer was separated, washed with HCl, filtered, washed with brine, dried ($MgSO_4$) and concentrated in vacuo. The residue was purified by column chromatography on silica gel using acetone/hexane (15/85) as an eluent to give compound ZZ as an oil $^1$H NMR (CDCl$_3$, 300 MHz): δ7.7 (dd, 1H), 7.5 (dd, 2H), 7.05 (dd, 2H), 6.85–6.7 (dd, 2H), 6.1 (m, 2H), 5.7 (m, 1H), 5.5 (m, 1H), 4.1(dd, 2H), 3.0 (doubled s, 3H), 1.73 (d, 3H).

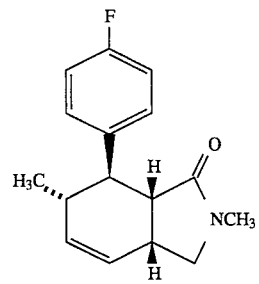
YY

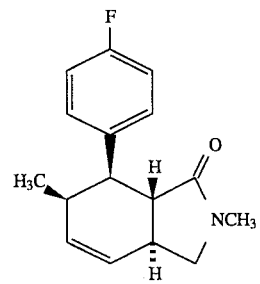
XX

Compounds YY and XX were prepared substantially as described in Procedure H using compound ZZ as the amide derivative instead of compound U.

Compound XX:

$^1$H NMR (CDCl$_3$, 300 MHz): δ7.15 (m, 2H), 7.0 (m, 2H), 5.85 (m, 1H), 5.7 (m, 1H), 3.3 (m, 2H), 3.17 (t, 1H), 2.85 (s, 3H), 2.75 (m, 1H), 2.5 (m, 2H), 0.61 (d, 3H).

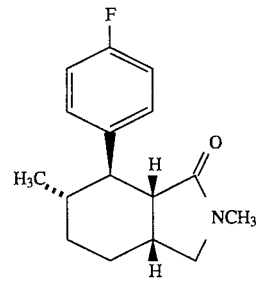
VV

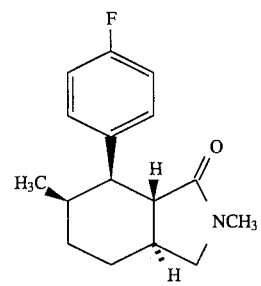
WW

Compounds VV and WW were prepared substantially as described in Procedure H substituting XX or YY for compound V or W.

Compound VV:

$^1$H NMR (CDCl$_3$, 300 MHz): δ7.1 (m, 2H), 6.95 (m, 2H), 3.35 (t, 1H), 2.85 (s, 3H), 2.65 (m, 1H), 2.5 (m, 1H), 2.1 (t, 1H), 1.8 (m, 3H), 1.6 (m, 3H), 0.61 (d, 3H).

Compound WW:

Anal. Calc'd for $C_{16}H_{16}NFO$: C, 73.53; H, 7.71; N, 5.36 Found: C, 73.55; H, 7.66; N, 5.36

EXAMPLE 10

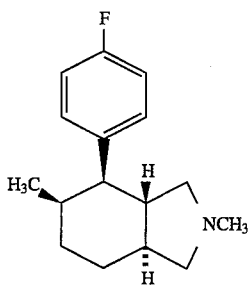
Cp-19

2,5α-Dimethyl-4α-(4-fluorophenyl)-3aα,7aβ
-octahydro-1H-isoindole Monofumarate

The title compound was prepared substantially as described in Example 2 using compound WW in place of compound F: mp 193°–195° C.

Anal. Calc'd for $C_{16}H_{22}FN.C_4H_4O_4$: C, 66.10; H, 7.21; N, 3.85 Found: C, 65.75; H, 7.12; N, 3.95

EXAMPLE 11

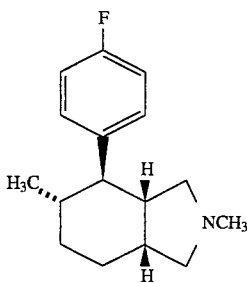
Cp-21

2,5β-Dimethyl-4α-(4-fluorophenyl)-3aα,7aα
-octahydro-1H-isoindole Monofumarate

A solution of compound VV (0.78 g, 3.0 mmol) in THF (10 mL) was added dropwise to a suspension of LAH (0.34 g, 9.0 mmol) and THF (5 mL) under Ar. The reaction mixture was heated to reflux for 4 h and cooled to room temperature. Water (0.34 mL), followed by 3N NaOH (1.0 mL) further followed by water (0.34 mL) were added dropwise to the stirred reaction mixture. The resulting solid precipitate was filtered and the mother liquor was concentrated in vacuo. The residue was treated with fumaric acid in isopropanol to give the title compound as a solid: mp 199°–203° C.

Anal. Calc'd for $C_{16}H_{22}FN.C_4H_4O_4$: C, 66.10; H, ;7.21 N, 3.85 Found: C, 66.29; H, 7.19; N, 3.72

EXAMPLE 12

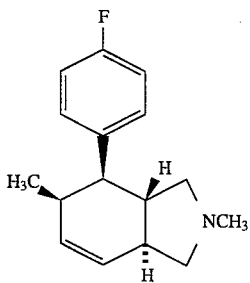
Cp-20

2,5α-Dimethyl-4α-(4-fluorophenyl)-2,3,3aα-4,5,7aβ
-hexahydro-1H-isoindole Monofumarate A solution of compound XX (2.8 g, 10.8 mmol) in THF (25 mL) was added dropwise to a suspension of LAH (1.23 g, 32 mol) and THF (25 mL) under Ar. The reaction was stirred at reflux for 4 h and cooled to room temperature. Water (1.23 mL), followed by 3N NaOH (3.75 mL) further followed by water (1.23 mL) were added dropwise to the stirred reaction mixture. The resulting solid precipitate was filtered and the mother liquor was concentrated in vacuo. The residue was treated with fumaric acid in isopropanol the give title compound as a solid: mp 187°–188° C.

Anal. Calc'd for $C_{16}H_{20}FN.C_4H_4O_4$: C, 66.47; H, 6.69; N, 3.88 Found: C, 66.56; H, 6.71; N, 3.75

PROCEDURE J

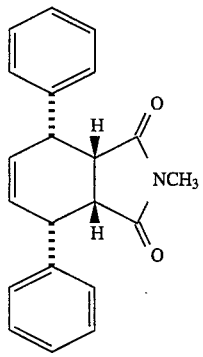
UU trans, trans-1,4-Diphenyl-1,3-butadiene (10.3 g, 50.0 mmol), N-methylmaleimide (6.6 g, 60 mmol) and xylenes (150 mL) were heated at 130° C. under $N_2$ for 15 h. The mixture was cooled and the resulting precipitate, compound UU was isolated and used without further purification.

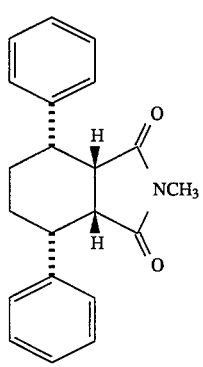
TT

10% Pd/C (1 g) was added to a solution of compound UU (9.94 g, 31.0 mmol) in ethyl acetate (125 mL) and the mixture was pressurized with $H_2$ (19.75 psi) for 40 min and left at room temperature for 16 h. An additional portion of 10% Pd/C (1 g) was added and the resulting mixture was pressurized (60 psi) for 16 h. The catalyst was filtered away and the filtrate was concentrated in vacuo to give compound TT as a solid, which was used without further purification.

EXAMPLE 13

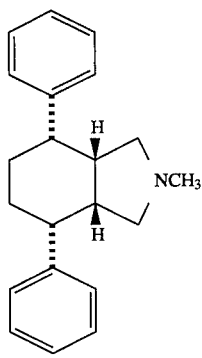

Cp-28

4β,7β-Diphenyl-2-methyl-3aα,7aα-octahydro-1H-isoindole 0.8 fumarate

A solution of compound TT (8 g, 25 mmol) in anhydrous THF (100 mL) was added dropwise to a suspension of LAH (4.98 g, 131 mmol) and THF (80 mL). This stirred mixture was heated at reflux for 4 h under $N_2$ and cooled to room temperature. Water (5.0 mL), followed by 3N NaOH (5.0 mL) further followed by water (15 mL) were added dropwise and the reaction mixture was stirred for 1.5 h. The resulting solid precipitate was filtered and the filtrate was washed with successive portions of THF, dried ($K_2CO_3$) and concentrated in vacuo. The residue was purified by column chromatography using silica gel and 5% MeOH/methylene chloride as an eluent to give the free base of the title compound as a solid. This solid was dissolved in isopropanol, treated with fumaric acid and MeOH to give the title compound as a solid: mp 208°–13° C.

Anal. Calc'd for $C_{21}H_{25}N.0.8\ C_4H_4O_4$: C, 75.52; H, 7.76; N, 3.64 Found: C, 75.64; H, 7.40; N, 3.64

PROCEDURE K

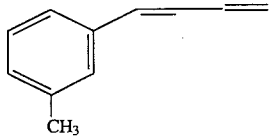

RR

Allyltriphenylphosphonium bromide (452 g, 1.3 mol) was added portionwise under Ar to a cooled solution of sodium bis(trimethylsilyl)amide (1.0 mol/THF 1.18 L, 1.18 mol) and THF (1.5 L). The resulting mixture was stirred for another 35 min at 0° C. and a solution of 3-methylbenzaldehyde (129 g, 1.75 mol) in THF (100 mL) was added (dropwise) to the mixture. The reaction mixture was stirred for 2.5 h at 0° C. and poured into ice/water. The organic layer was removed and washed with successive portions of water and brine, dried ($MgSO_4$) and concentrated in vacuo. The residue was dissolved at reflux in t-butylmethylether and cooled to 0° C. The resulting precipitate (triphenyl phosphine oxide) was removed by filtration and the filtrate was concentrated in vacuo. The residue was purified by column chromatography on silica gel using hexane/acetone (10/1) as an eluent to give the diene RR, as an oil.

Anal. Calc'd for $C_{11}H_{10}$: C, 91.61; H, 8.39 Found: C, 91.46; H, 8.40

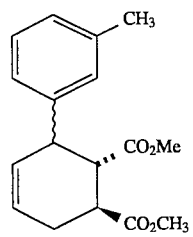

QQ

A mixture of 1-(3-methylphenyl)-1,3-butadiene (137 g, 0.96 mol), dimethyl fumarate (151.7 g, 1.06 mol) and ethylene glycol (685 mL) was heated at 60° C. for 16 h. The reaction mixture was poured into water and the organic extract was washed with water and brine, dried ($MgSO_4$) and concentrated in vacuo. The residue was purified by crystallization from methylcyclohexane/ethyl acetate (which removed the unreacted dimethyl fumarate), bulb to bulb distillation of the mother liquor (at 0.001 mm Hg and 90°–140° C.) and column chromatography on silica gel using hexane as an eluent to give the desired diester diastereomeric intermediates QQ as an oil.

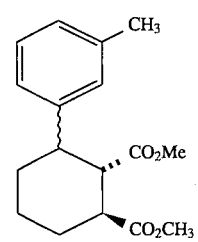

PP

A mixture of the diester diastereomers QQ (78.0 g, 0.27 mol), ethyl acetate (600 mL) and 10% Pd/C (7.8 g) was placed on a Parr shaker and pressurized with $H_2$ (60 psi) for 2 h. The catalyst was removed by filtration, the filtrate was concentrated in vacuo and the residue was purified by column chromatography (silica gel, hexane:acetone 1:1) to give the saturated diester diastereomeric intermediates PP as an oil.

Anal. Calc'd for $C_{17}H_{22}O_4$: C, 70.32; H, 7.64 Found: C, 70.55; H, 7.58

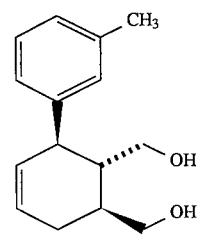

OO

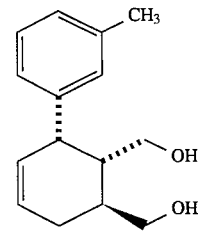

NN

A solution of the diester diastereomeric derivatives PP (70.12 g, 0.24 mol) in ether (600 mL) was added dropwise to a cooled suspension of LAH (45.2 g, 1.19 mol) in ether (600 mL) under Ar over 2.5 h. This mixture was stirred

49 overnight at room temperature. Water (45 mL), followed by 3N NaOH (135.0 mL) further followed by water (45 mL) were added dropwise and the reaction mixture was stirred for 1 h The resulting solid precipitate was filtered off and the filtrate was washed with successive portions of THF. The combined organic extracts were washed with water, dried (MgSO$_4$) and concentrated in vacuo. The residue was purified by chromatography on a Waters Prep 500 HPLC using a CH$_2$Cl$_2$/MeOH gradient followed by recrystallization from methylcyclohexane/ethyl acetate to give the separated diastereomers OO and NN as solids.

Compound OO:

$^1$H NMR (CDCl$_3$, 300 MHz): δ7.2-7.1 (m, 1H), 7.05-6.9 (m, 3H), 3.8-3.45 (m, 4H), 3.25 (m, 1H), 2.3 (s, 3H), 1.9-1.1 (m, 5H)

Compound NN:

$^1$H NMR (CDCl$_3$, 300 MHz): δ7.3-6.95 (m, 4H), 3.8 (m, 2H), 3.55 (m, 2H), 2.95 (m, 1H), 2.35 (s, 3H), 2.15 (m, 1H), 2.0 (m, 2H), 1.85-1.35 (m, 3H) Anal. Calc'd for C$_{15}$H$_{22}$O$_2$: C, 76.88; H, 9.46 Found: C, 77.21; H, 9.53

EXAMPLE 14

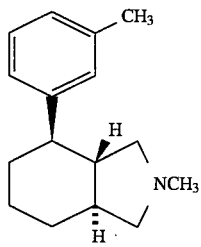

Cp-24

3aα,7aβ Octahydro-2-methyl-4α-(3-methylphenyl)-1H-isoindole Monofumarate

A solution of methanesulfonyl chloride (2.5 mL, 32.3 mmol) in methylene chloride (7 mL) was added to a solution of compound OO (3.45 g, 14.7 mmol) and triethylamine (4.5 mL, 32.3 mmol) in methylene chloride (40 mL) at 0° C. under Ar. The mixture was stirred at 0° C. for 2 h and poured into NaHCO$_3$/ice. The organic layer was separated, washed with successive portions of water and brine, dried (Na$_2$SO$_4$) and concentrated in vacuo. The residue was dissolved in EtOH (40 mL), placed in a Parr bottle and gaseous methylamine was bubbled into the solution for 2 min. This mixture was sealed and heated at 80° C. for 16 h and concentrated in vacuo. The resulting residue was partitioned between ether and 3N NaOH. The organic layer was washed with water and brine, dried (K$_2$CO$_3$) and concentrated in vacuo. The residue was treated with fumaric acid and recrystallized from isopropanol and ether to give the title compound as a solid: mp 145°-148° C.

Anal. Calc'd for C$_{16}$H$_{23}$N.C$_4$H$_4$O$_4$: C, 69.54; H, 7.88; N, 4.05 Found: C, 69.84; H, 7.89; N, 4.03

50

EXAMPLE 15

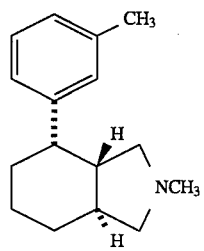

Cp-23

3aα,7aβ Octahydro-2-methyl-4β-(3-methylphenyl)-1H-isoindole Monofumarate

A solution of methanesulfonyl chloride (2.9 mL, 37.4 mmol) in methylene chloride (8 mL) was added to a solution of compound NN (4.0 g, 17 mmol) and triethylamine (5.2 mL, 37.4 mmol) in methylene chloride (40 mL) at 0° C. under Ar. The mixture was stirred at 0° C. for 2.5 h and poured into NaHCO$_3$/ice. The organic layer was separated, washed with successive portions of water and brine, dried (Na$_2$SO$_4$) and concentrated in vacuo. The residue was dissolved in EtOH (40 mL), placed in a Parr bottle and gaseous methylamine was bubbled into the solution. This mixture was sealed and heated at 80° C. for 16 h and concentrated in vacuo. The resulting residue was partitioned between ether and 3N NaOH. The organic layer was washed with water and brine, dried (K$_2$CO$_3$) and concentrated in vacuo. The residue purified by a combination of techniques which include column chromatography, treatment with fumaric acid and recrystallization from isopropanol to give the title compound as a solid: mp 158°-160° C.

Anal. Calc'd for C$_{16}$H$_{23}$N.C$_4$H$_4$O$_4$: C, 69.54; H, 7.88; N, 4.05 Found: C, 69.53; H, 7.89; N, 3.98

PROCEDURE L

The following general procedure was used to synthesize the compounds listed in Tables 4 and 5.

A mixture of an appropriately substituted butadiene derivative AD1 (1.0 mol: obtained commercially, prepared from a literature procedure or prepared substantially as described in procedure K), dimethyl fumarate (1.1 mol) and ethylene glycol (720 mL) was heated at 60° C. for 10–24 h. The reaction mixture was poured into water and the organic extract was washed with water and brine, dried with a suitable drying agent and concentrated in vacuo. The residue was purified by a combination of crystallization from a suitable solvent, vacuum distillation and column chromatography to give the desired diester diastereomeric intermediates AD3 and AD4. A mixture of the diester diastereomers AD3 and AD4 (1.0 mol), ethyl acetate (2.2 L) and 10% Pd/C (28.86 g) was placed on a Parr shaker and pressurized with H$_2$ (60 psi) for 2–24 h. The catalyst was removed by filtration, the filtrate was concentrated in vacuo and the residue was purified by column chromatography to give the saturated diester diastereomeric intermediates.

A solution of the saturated diester diastereomeric derivatives (1.0 mol) in a suitable solvent such as ether (2.4 L) was added dropwise to a cooled suspension of LAH (4.8 mol) and ether (2.4 L) under Ar over 2.5–4.5 h. This mixture was stirred overnight at room temperature. Water (180 mL), followed by 3N NaOH (540 mL) further followed by water (180 mL) were added dropwise and the reaction mixture was stirred for 1–3 h The resulting solid precipitate was filtered and the filtrate was washed with successive portions of THF. The combined organic extracts were washed with water, dried with a suitable drying agent and concentrated in vacuo. The residue was purified by a combination of column chromatography and recrystallization to give the separated diastereomers AD5 and AD6. A solution of methanesulfonyl chloride (22.0 mmol) in methylene chloride (4.76 mL) was added to a solution of the appropriately substituted separated diastereomer (10.0 mmol) and triethylamine (22.0 mmol) in methylene chloride (27.2 mL) at 0° C. under Ar. The mixture was stirred at 0° C. for 2 h and poured into NaHCO$_3$/ice. The organic layer was separated, washed with successive portions of water and brine, dried (Na$_2$SO$_4$)and concentrated in vacuo. The residue was dissolved in EtOH (40 mL), placed in a Parr bottle and gaseous methylamine was bubbled into the solution for 2 min. This mixture was sealed and heated at 80° C. for 16 h and concentrated in vacuo. The resulting residue was partitioned between a suitable organic solvent and 3N NaOH. The organic layer was washed with water and brine, dried with a suitable drying agent and concentrated in vacuo. The residue was treated with fumaric acid and recrystallized from an appropriate solvent to give the desired 4-arylisoindole.

PROCEDURE M

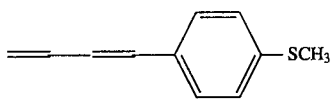

A solution of allyltriphenylphosphonium bromide (421.5 g, 1.1 mol) in dry THF (500 mL) was added portionwise under Ar to a cooled (5°–10° C.) solution of sodium bis(trimethylsilyl)amide (1.0 mol/THF: 1000 mL, 1.0 mol) and THF (1.2 L). The resulting mixture was stirred for another 1 h at 10° C. and a solution of 4-methylthiobenzaldehyde (152 g, 1.0 mol) in THF (500 mL) was added to the mixture over 1.5 h. The reaction mixture was stirred for 1.75 h at 10° C. and partitioned between water and ether. The organic layer was removed and the resulting aqueous layer was washed with several portions of ether. The combined organic layers were dried (MgSO$_4$) and concentrated in vacuo. The residue which partially crystallized upon standing was washed with several portions of hexane and filtered. The filtrate was concentrated in vacuo and purified by a combination of column chromatography on silica gel using hexane as an eluent and recrystallization from MeOH/acetonitrile to give diene MM, as a solid.

TABLE 4

| Cp-n | (R$^a$)$_n$ | R$^c$ | mp °C. | C | H | N | Empirical Formula | MS (MH$^+$) |
|---|---|---|---|---|---|---|---|---|
| Cp-16 | 4-CF$_3$ | CH$_3$ | 150–52 | 57.95 | 5.83 | 3.69 | C$_{16}$H$_{20}$F$_3$N.C$_2$H$_2$O$_4$ | 284 |
| Cp-18 | 3-CF$_3$ | n-Bu | 139–44 | 59.58 | 6.88 | 3.39 | C$_{19}$H$_{26}$F$_3$N.C$_2$H$_2$O$_4$ | 326 |
| Cp-15 | 3,4-di Cl | CH$_3$ | 184–85 | 57.01 | 5.79 | 3.50 | C$_{15}$H$_{19}$Cl$_2$N.C$_4$H$_4$O$_4$ | |
| Cp-25 | 3-CF$_3$ | iso-Bu | 139–41 | 61.82 | 6.65 | 3.23 | C$_{18}$H$_{24}$F$_3$N.C$_4$H$_4$O$_4$ | 312 |

TABLE 5

| Cp-n | (R$^a$)$_n$ | R$^c$ | mp °C. | C | H | N | Empirical Formula | MS (MH$^+$) |
|---|---|---|---|---|---|---|---|---|
| Cp-17 | 4-CF$_3$ | CH$_3$ | 150–52 | 57.90 | 5.94 | 3.75 | C$_{16}$H$_{20}$F$_3$N.C$_2$H$_2$O$_4$ | 284 |
| Cp-14 | 3,4-di Cl | CH$_3$ | 184–85 | 57.08 | 5.77 | 3.47 | C$_{15}$H$_{19}$Cl$_2$N.C$_4$H$_4$O$_4$ | — |
| Cp-22 | 4-CF$_3$ | (CH$_2$)$_2$CH(Ph)$_2$ | 164–66 | 70.77 | 6.26 | 2.57 | C$_{30}$H$_{32}$F$_3$N.C$_4$H$_4$O$_4$ | 284 |
| Cp-30 | 3-CH$_3$ | (CH$_2$)$_2$N(CH$_3$)$_2$ | 253–55 | 63.89 | 9.50 | 9.50 | C$_{20}$H$_{32}$N$_2$.2HCl.0.02H$_2$O | 301 |

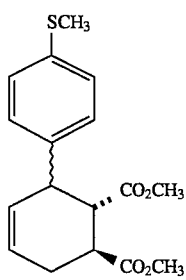

LL

A mixture of compound MM (17.5 g, 0.1 mol), dimethyl fumarate (14.9 g, 0.1 mol) and ethylene glycol (150 mL) was heated at 60° C. for 33 h. The reaction mixture was poured into water and extracted with ether. The combined organic extracts were dried (MgSO₄) and concentrated in vacuo. The residue was purified by column chromatography on silica gel using hexane/ethyl acetate as an eluent to give the desired diester intermediate LL as a mixture of diastereomers.

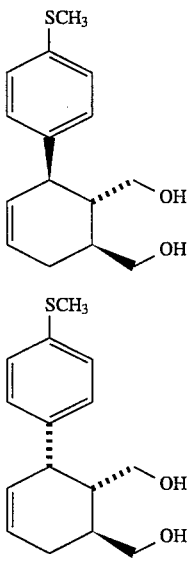

JJ

KK

A solution of the diester diastereomeric derivatives LL (34.0 g, 0.106 mol) in ether (340 mL) was added dropwise to a cooled suspension of LAH (21.2 g, 0.56 mol) and ether (210 mL) under Ar. This mixture was stirred overnight at room temperature. Water (21 mL), followed by 3N NaOH (21 mL) further followed by water (63 mL) were added dropwise to the stirred reaction mixture. The resulting solid precipitate was filtered and the filtrate was washed with successive portions of ether and methylene chloride. The combined organic extracts were concentrated in vacuo, dissolved in methylene chloride, dried (MgSO₄) and concentrated in vacuo. The residue was purified by column chromatography (Waters Prep 500: methylene chloride/acetone, 90:10), to give the separated diastereomers JJ and KK as oils.

EXAMPLE 16

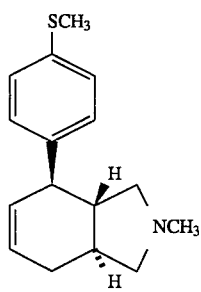

Cp-27

3aα,4α,7aβ
Octahydro-2-methyl-4-(4-methylthiophenyl)-
1H-isoindole Monofumarate

The title compound was prepared substantially as described in Example 14, where compound JJ is used in place of compound OO to give the title compound as a solid: mp 183°–185° C.

¹H NMR (DMSOd₆:300 MHz) 7.25 (d, 2H), 7.12 (d, 2H), 6.45 (s, 2H), 5.85 (m, 1H), 5.55 (d, 1H), 3.40 (m, 2H), 3.00 (m, 2H), 2.85 (t, 1H), 2.65 (s, 3H), 2.45 (s, 3H), 2.42 (m, 1H), 2.15 (m, 1H), 2.00 (m, 2H). Anal. Calc'd for C₁₆H₂₁NS.C₄H₄O₄: C, 63.98; H, ;6.71 N, 3.73 Found:.C, 63.89; H, 6.80; N, 3.57

PROCEDURE N

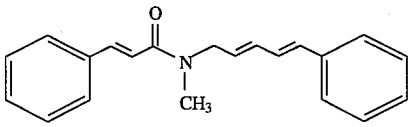

II

Compound II was prepared essentially as described in Procedure H using cinnamyltriphenylphosphonium chloride in place of allyltriphenylphosphonium bromide to give compound II as an oil.

¹H NMR (CDCl₃, 300 MHz): δ7.8-7.1 (m, 12H), 6.95-6.3 (m, 4H), 4.4, 4.3, 4.2, 4.15, (dd of d, 2H), 3.11 (s, 3H), 3.08 (s, 3H), 3.06 (s, 3H).

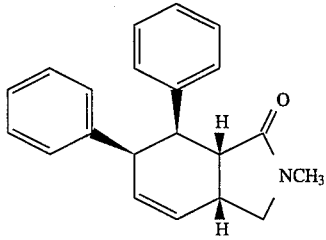

HH

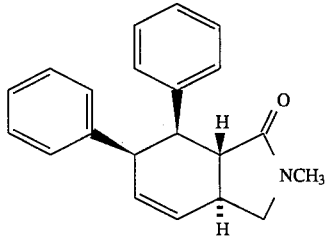

GG

Compounds HH and GG were prepared substantially as described in procedure H using compound II in place of compound U.

Compound GG:

$^1$H NMR (CDCl$_3$, 300 MHz): δ7.1 (m, 6H), 6.65 (m, 4H), 6.15 (m, 1H), 5.32 (m, 1H), 3.8 (m, 1H), 3.6 (m, 1H), 3.45 (m, 1H), 3.25 (m, 1H), 2.9 (m, 1H), 2.8 (s, 3H), 2.7 (t, 1H).

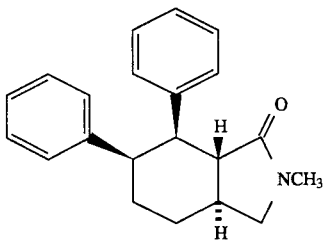

FF

Compound FF was prepared substantially as described in procedure B using compound GG in place of compound F.

Compound FF:

$^1$H NMR (CDCl$_3$, 300 MHz): δ7.0 (m, 6H), 6.85 (m, 2H), 6.7 (m, 2H), 3.35 (m, 1H), 3.25 (m, 3H), 2.8 (s, 3H), 2.7 (t, 1H), 2.2 (m, 2H), 2.1 (m, 3H).

EXAMPLE 17

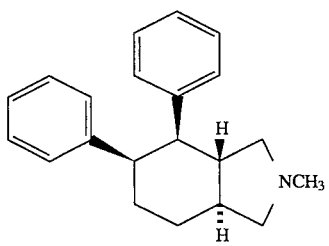

4α,5α-Diphenyl-2-methyl-3aα,7aβ
-octahydro-1H-isoindole Monofumarate

The title compound was prepared substantially as described in Example 11 using compound FF in place of compound VV: mp 78°–79° C.

Anal. Calc'd for C$_{21}$H$_{25}$N: C, 86.55; H, 8.64; N, 4.81
Found: C, 86.57; H, 8.45; N, 4.73

PROCEDURE O

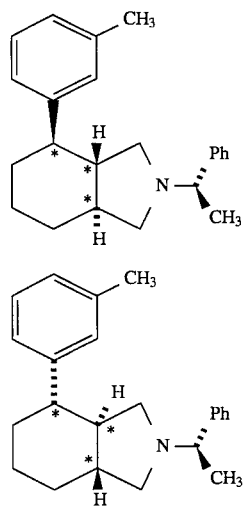

EE

DD

A solution of methanesulfonyl chloride (14.1 mL, 0.18 mol) in methylene chloride (35 mL) was added to a solution of compound OO (19.46 g, 0.083 mol) and triethylamine (24.2 mL, 0.18 mol) in methylene chloride (175 mL) at 0° C. under Ar. The mixture was stirred at 0° C. for 2 h and poured into NaHCO$_3$/ice. The organic layer was separated, washed with successive portions of water and brine, dried (Na$_2$SO$_4$) and concentrated in vacuo. The residue was dissolved in EtOH (190 mL) and R-(+)-α -methylbenzylamine (74 mL, 0.58 mol) was added. This mixture was heated at 60° C. under Ar for 16 h and concentrated in vacuo. The resulting residue was partitioned between ether and 3N NaOH. The organic layer was washed with water and brine, dried (K$_2$CO$_3$) and concentrated in vacuo. The residue was passed through a Water's Prep column (to remove some of the unreacted amine) and dissolved in ether. CO$_2$ was bubbled into the ethereal solution and the resulting solid was removed by filtration. The filtrate was concentrated in vacuo and purified by column chromatography on a Water's Prep 500 using 10% acetone/hexane as an eluent. There were obtained two spots corresponding to compounds EE and DD.

Compound EE

Anal. Calc'd for C$_{23}$H$_{29}$N: C, 86.47; H, 9.15; N, 4.38
Found: C, 86.22; H, 9.22; N, 4.39

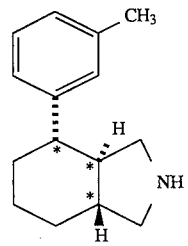

CC

Compound EE or DD (8.29 g, 0.026 mol) and ammonium formate (11.4 g, 0.182 mol) were added to a suspension of 10% Pd/C (8.3 g) and MeOH (250 mL) under Ar and the resulting mixture was heated to reflux for 1 h. The catalyst was removed by filtration and the filtrate was concentrated in vacuo. The residue was partitioned between methylene chloride and aqueous NaOH. The organic layer was washed with successive portions of water and brine, dried (Na$_2$SO$_4$) and concentrated in vacuo. 10 % Pd(OH)/C (0.3 g) was added to a solution of this residue in MeOH (50 mL) and the mixture was placed on a Parr shaker and pressurized with H$_2$ at 60 ° C. for 16 h. The catalyst was removed by filtration and the filtrate was concentrated in vacuo to give compound CC as an oil.

EXAMPLE 18

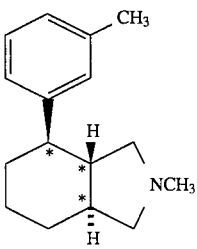

Cp-24$^+$ or Cp-24$^-$ (−)3aα,7aβ
Octahydro-2-methyl-4α-(3-methylphenyl)-
1H-isoindole Monofumarate A suspension of 10% Pd/C (2.6 g), compound CC or BB (2.62 g, 12.19 mmol), 37% aq. formaldehyde (1.44 mL, 36.57 mmol) was placed in a Parr shaker and agitated for 1 h. The catalyst was removed and another portion of 10% Pd/C (0.5 g) was added. This mixture was sealed, agitated for 1.5 h and filtered. The filtrate was concentrated in vacuo and the residue was passed through a silica gel column using methylene chloride/MeOH/NH4OH (80/20/1) as an eluent. The desired fractions were concentrated in vacuo and partitioned between ether and 3N NaOH. The organic layer was washed with successive portions of water and brine, dried ($K_2CO_3$) and concentrated in vacuo. The residue was treated with fumaric acid and crystallized from isopropanol/ether to give the title compound as a solid: mp 143°–145° C., $[\alpha]^{25}_D$= (–)54.3. Cp-24⁻

Anal. Calc'd for $C_{16}H_{23}N/C_4H_4O_4$: C, 69.54; H, 7.88; N, 5.05. Found: C, 69.47; H, 8.01; N, 3.89.

PROCEDURE P

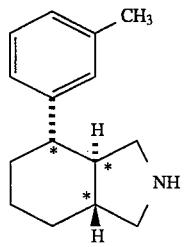

BB

Compound DD or EE (7.15 g, 0.022 mol) and ammonium formate (9.9 g, 0.154 mol) were added to a suspension of 10% Pd/C (7.15 g) and MeOH (250 mL) under Ar and the resulting mixture was heated to reflux for 1 h. The catalyst was removed by filtration and the filtrate was concentrated in vacuo. The residue was partitioned between methylene chloride and aqueous NaOH. The organic layer was washed with successive portions of water and brine, dried ($Na_2SO_4$) and concentrated in vacuo. 10% Pd/C (0.3 g) was added to a solution of the residue in MeOH (60 mL) and this mixture was placed on a Parr shaker and pressurized with $H_2$ (50 psi) at 60° C. for 16 h. The catalyst was removed by filtration and the filtrate was concentrated in vacuo to give compound BB as a green solid: mp 166°– 170° C.

EXAMPLE 19

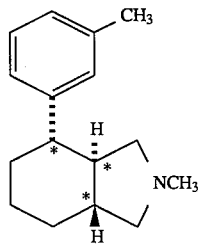

Cp-24⁺ or Cp-24⁻

(+)3aα,4α,7aβ
Octahydro-2-methyl-4-(3-methylphenyl)-
1H-isoindole Monofumarate

The title compound was prepared essentially as described in example 18 except that compound CC was replaced with compound BB, respectively. The product was isolated as a solid: mp 144°–146° C., $[\alpha]^{25}_D$=(+)54.05.

¹H NMR (DMSO d₆, 300 MHz): δ7.2 (t, 1H), 7.1-7.0 (m, 3H), 6.45 (s, 2H), 3.35 (dd, 1H), 2.9-2.7 (m, 3H), 2.65 (s 3H), 2.5-2.4 (m, 1H), 2.3 (s, 3H), 2.1 -1.95 (m, 1H), 1.9-1.75 (m, 4H), 1.45 (t, 2H), 1.2 (m, 1H). Cp-24⁺ Anal. Calc'd for $C_{16}H_{23}N/C_4H_4O_4$: C, 69.54; H, 7.88; N, 5.05. Found: C, 69.69; H, 8.08; N, 3.99.

EXAMPLE 20

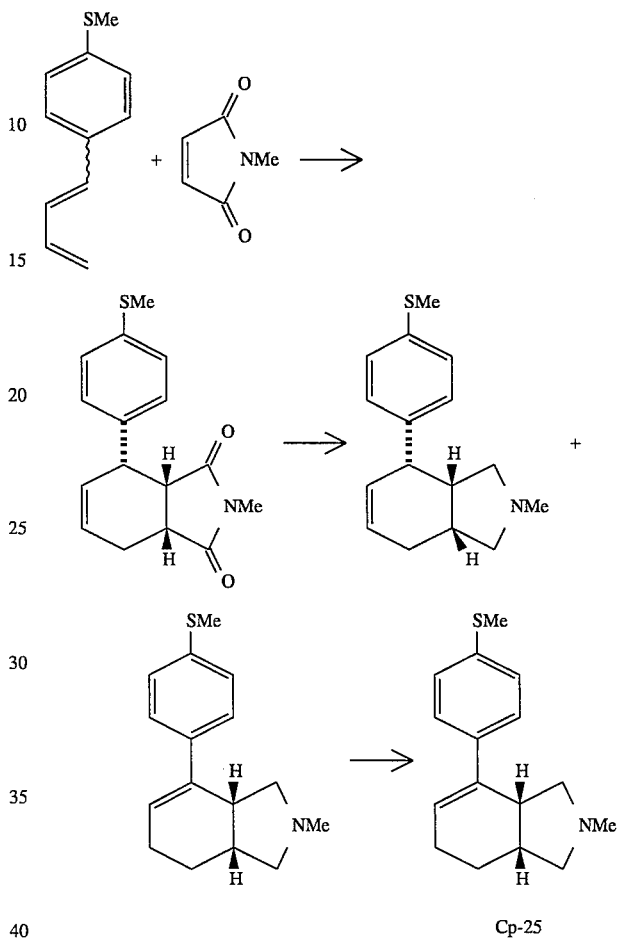

Cp-25

(1) 2-Methyl-4α-(4-methylsulfanylphenyl)-3aα,4,7,7aα-tetrahydroisoindole-1,3-dione. A 17.6 g (0.1 mole) sample of a mixture of cis and trans 1-(4-methylthiophenyl)-1,3-butadiene and 11.1 g (0.1 mole) of N-methylmaleimide were added to 100 mL of ethylene glycol and heated at 100° C. for 42 h. The mixture was partitioned between $CH_2Cl_2$ and water, and organic layer was separated, and dried ($MgSO_4$). The organic solution was evaporated in vacuo and the diastereoisomers separated on the Waters Prep 500 ($SiO_2$) eluting with 10% acetone: 90% $CH_2Cl_2$ to give 4 g (28% yield) of a yellow oil.

¹H NMR (CDCl₃): δ2.5 (m, 5H); 3.0 (s, 3H); 3.1 (m, 1H); 3.25 (dd, 1H); 4.0 (m, 1H); 6.05 (m, 2H); 7.2 (m, 4H). MS-EI, m 287.

(2) 2-Methyl-4α-(4-methylsulfanylphenyl)-2,3,3aα,4,7,7aα-hexahydro-1H-isoindole and 2-Methyl-4-(4-methylsulfanylphenyl)-2,3,3aα,6,7,7aα -hexahydro-1H-isoindole (88%: 12%). A solution of 3.65 g (0.0127 mole) of 2-methyl-4β-(4-methylsulfanylphenyl)-3aα,7aα-tetrahydroisoindole-1,3 -dione in 50 mL of THF was added portionwise to a suspension of 2.53 g (0.0667 mole) lithium aluminum hydride in 25 mL of THF. The mixture was refluxed for 4.5 h. To the mixture at room temperature was added dropwise 2.53 mL $H_2O$. 2.53 mL of 3N NaOH, then 7.5 mL of $H_2O$. The inorganic solid was filtered off, and the filter cake washed with CH₂Cl₂. The filtrates were combined, dried (K₂CO₃), and evaporated in vacuo to a yellow oil. Flash chromatography (SiO₂) eluting with 1—10—90:NH₄OH—MeOH—CH₂Cl₂ gave 1.56 g (48% yield) of an oil. A sample of 0.699 g of fumaric acid was added to the oil in methanol and ether added to precipitate the salt. Recrystallization from methanol gave 0.79 g (24% yield) of a tan solid, mp 120°–124° C.

¹H NMR (DMSO d₆): δ1.92–2.02 (d, 1H); 2.2–2.3 (m, 1H); 2.3–2.42 (m, 1H); 2.45 (s, 3H); 2.5–2.58 (m, 1H); 2.68 (s, 3H); 2.9–3.08 (m, 3H); 3.12–3.28 (m, 2H); 5.61–5.68 (d, 1H); 5.82-5.68 (d, 1H); 5.82–5.9 (m, 1H); 6.5 (s, 2.5H); 7.14–7.18 (d, 2H); 7.22–7.26 (d, 2H). Anal. Cal'd for C₁₆H₂₁NS/1.2 C₄H₄O₄: C,63.03; H,6.74; N, 3.55; Found: C,62.66; H,6.52; N, 3.53.

(3) 2-Methyl-4-(4-methylsulfanylphenyl)-2,3,3aα,6,7,7aα-hexahydro-1H-isoindole, Cp-25. A 110 mg (0.00424 mole) of 2-methyl-4α-(4-methylsulfanylphenyl)-2,3,3aα,4α,7,7aα-hexahydro-1H-isoindole was dissolved in 0.425 mL (0.00425 mole) of a solution of 1M potassium t-butoxide in THF and refluxed for 6 h, then allowed to stand at room temperature overnight. The solution was partitioned between water-methylene chloride, the methylene chloride layer separated, and dried (K₂CO₃). Evaporation of the CH₂Cl₂ under a stream of nitrogen gave 90 mg (82% yield) of an oil, which was dissolved in 2-propanol and treated with 40 mg of fumaric acid. The salt was dried and isolated as a solid: mp 164°– 165° C.

¹H NMR (DMSO d₆): δ1.4–1.6 (m, 1H); 1.62–1.72 (m, 1H); 2.1–2.2 (m, 2H); 2.4–2.6 (m, 2H); 2.48 (s, 3H); 2.52 (s, 3H); 2.8–2.9 (m, 1H); 3.15–3.25 (m, 2H); 3.4–3.5 (m, 1H); 6.2–6.25 (m, 1H); 6.55 (s, 2H); 7.15–7.22 (d, 2H); 7.3–7.35 (d, 2H). Anal. Cal'd for C₁₆H₂₁NS/C₄H₄O₄: C, 63.98; H, 6.71; N, 3.73 Found: C, 63.82; H, 6.61; N, 3.67

Example 21

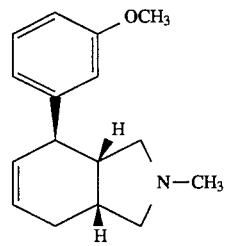

Cp-31

4α-(3-Methoxyphenyl)-2-methyl-3,3aα,4,7,7aα-hexahydro-1H-isoindole fumarate

A solution of 5 g (0.018 mole) 4α-(3-methoxyphenyl)-2-methyl-3aα,4,7,7aα-tetrahydro-1H-isoindole-1,3(2H)-dione, ZZZ, in 25 mL THF was added dropwise to a suspension of 7.1 g (0.018 mole) LAH in 70 mL THF. The reaction was stirred overnight under argon. The reaction was quenched with added 7.0 mL H₂O, 21 mL 3N NaOH and 7 mL H₂O. After stirring 45 minutes the solid was filtered off and the filter cake washed well with THF. The filtrate was washed with H₂O, brine, and dried (K₂CO₃). The solvent was removed in vacuo and the residue was flash chromatographed on silica gel (90:10:1, CH₂Cl₂:MeOH:NH₄OH). The free base was converted to the fumarate salt in 2-PrOH/Et₂O to give 3.28 g of product: mp. 91°–93° C.

Mass spectrum (Cl-CH₄) m/z 244 (M+ 1). ¹H NMR (Me₂SO d-6) δ7.25 (t, 1 H), 6.8 (m, 3 H), 6.5 (s, 2 H), 5.9 (m, 1 H), 5.7(bd, 1 H), 3.7(s, 3 H), 3.25-3.1 (m, 2 H), 3.0 (m, 3 H), 2.5 (m, 1 H), 2.65 (s, 3 H), 2.4-2.2 (m, 2 H), 2.0 (m, 1 H). Anal calcd for C₁₆H₂₁NO.C₄H₄O₄: C, 66.84; H, 7.01; N, 3.90. Found: C, 66.84; H, 6.93; N, 3.89.

PROCEDURE Q

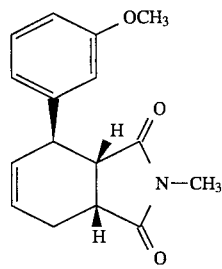

ZZZ

4α-(3-Methoxyphenyl)-2-methyl-3aα,4,7,7aα-tetrahydro-1H-isoindole-1,3(2H)-dione

The cis-1-(3-methoxyphenyl)-1,3-butadiene (10.0 g, 0.06 mole), diene G, from procedure D was heated to 100° C. in 60 mL ethylene glycol with 7 g (0.06 mole) N-methylmaleimide overnight. After cooling the reaction was partitioned between Et₂O and H₂O. The organics were separated off and washed with H₂O, brine and dried (MgSO₄). The solvent was evaporated in vacuo. The product was passed through two flash chromatography columns on silica gel (8:1 hexane:acetone then 1:1 hexane:acetone).

Mass spectrum (Cl-CH₄) m/z 272 (M+ 1). ¹H NMR (CDCl₃) δ7.25 (t, 1 H); 6.9–6.7 (m, 3 H); 6.05 (d, 2 H); 4.0 (m, 1 H); 3.8 (s, 3 H); 3.3 (dd, 1 H); 3.1 (td, 1 H); 3.0 (s, 3 H); 2.5 (m, 2 H).

PROCEDURE R

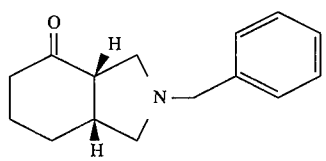

TTT 2-(Phenylmethyl)-3aα,7aα-octahydro-1H-isoindol-4-one

A solution of N-methoxybutyl-N-(trimethylsilyl)benzylamine (90.06 g; 0.32 mole) and 2-cyclohexene-1-one (25 mL; 0.25 mole) in 320 mL of CH₂Cl₂ and 16 mL of 1% TFA in CH₂Cl₂ was heated under reflux for 2 h. The reaction was cooled and approximately 20 g of K₂CO₃ was added and the reaction stirred for 45 m. The solid was filtered off and the solvent evaporated in vacuo. The residue was partitioned between Et₂O/3N NaOH, the organics were separated off and washed with H₂O and brine and dried (K₂CO₃). The solvent was removed in vacuo. The oil was treated with oxalic acid in 2-PrOH and EtOH. The solid was collected to give 35.01 g of a solid: mp. 129°–130° C.

Mass spectrum (Cl-CH₄) m/z 229 (M+ 1). ¹H NMR (CDCl₃) δ7.3 (m, 5 H); 3.6 (s, 2 H); 2.9-2.6 (m, 4 H); 2.4 (t, 2 H); 2.25 (m, 2 H); 1.9-1.8 (m, 3 H); 1.4 (m, 1 H). Anal calcd for C₁₅H₁₉NO.C₂H₂O₄: C, 63.94; H, 6.63; N, 4.39. Found: C, 63.7; H, 6.62; N, 4.24.

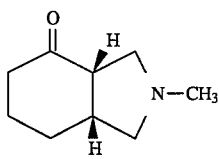 YYY

2-Methyl-3aα,7aα-octahydro-1H-isoindol-4-one

2-Benzyl-3aα,7aα-octahydro-1H-isoindol-4-one, TTT, (2.5 g, 0.011 mole) and 2.1 g (0.011 mole) methyl tosylate were combined in 30 mL EtOAc and stirred overnight. An additional 1.2 g (0.0064 mole) of methyl tosylate was added and the reaction stirred for 72 h. The solid was filtered off and washed well with $Et_2O$. The solid was taken up in 30 mL absolute EtOH and placed over 0.4 g 10% palladium on carbon. This was placed on a Parr shaker and shaken for 1.5 h under 50 psi of hydrogen. The catalyst was filtered off and the filtrate was evaporated in vacuo. The residue was partitioned between $Et_2O$ and 3N NaOH, the organics were separated off and washed with $H_2O$ and brine and dried ($K_2CO_3$). The solvent was evaporated in vacuo. The residue was distilled in a bulb to bulb distillation apparatus to give 1.31 g of a clear oil.

Mass spectrum (Cl-$CH_4$) m/z 154 (M+ 1). $^1$NMR ($CDCl_3$) δ2.9-2.7 (m, 5H); 2.5-2.4 (m, 3 H); 2.3 (s, 3 H); 2.3 (m, 1H); 2.0-1.8 (m, 2H); 1.5-1.4 (m, 1H).

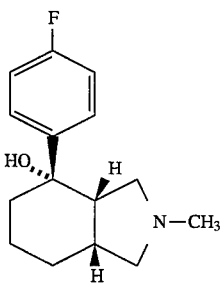 XXX

4α-(4-Fluorophenyl)-4β-hydroxy-2-methyl-3aα,7aα-octahydro-1H-isoindole fumarate

A solution of 3.3 mL (0.029 mole) of 4-bromofluorobenzene in 15 mL THF was added dropwise to a solution of 18.75 mL (0.029 mole) of 1.6M n-butyllithium at −78° C. After stirring for one hour, this solution was added via cannula to a solution of 1.5 g (0.0095 mole) of 2-methyl-3aα,7aα-octahydro- 1H-isoindol-4-one, YYY, in 30 mL THF also at −78° C. After stirring for 2 h the reaction was poured into $H_2O$, the organics were separated and washed with $H_2O$, brine and dried ($K_2CO_3$). The solvent was evaporated in vacuo. The residue was passed through a flash chromatography column on silica gel (80:20:2 $CH_2Cl_2$:MeOH:$NH_4OH$). The product was converted to the fumarate salt in 2-PrOH: mp. 192°–193° C.

Mass spectrum (Cl-$CH_4$) m/z 251 (M+ 1). $^1$H NMR ($Me_2SO$ d-6) δ7.55 (m, 2H); 7.15 (m, 2 H); 6.5 (s, 2 H); 3.3 (t, 1 H); 3.1-3.0 (m, 2 H); 2.9 (d, 1 H); 2.7 (s, 3 H); 2.6 (m, 1 H); 2.5 (m, 1 H); 1.85-1.6 (m, 5 H); 1.35 (m, H). Anal calcd for $C_{15}H_{20}FNO \cdot C_4H_4O_4$: C, 62.45; H, 6.62; N, 3.83. Found: C, 62.14; H, 6.61; N, 3.77.

Example 22

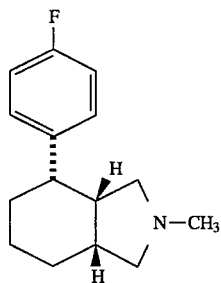 Cp-32

4β-(4-Fluorophenyl)-2-methyl-3aα,7aα-octahydro-1H-isoindole fumarate

4α-(4-Fluorophenyl)-4β-hydroxy-2-methyl-3aα,7aα-octahydro-1H-isoindole, XXX, (0.74 g, 0.0032 mole), was added to a Parr bottle containing 0.37 g 10% palladium on carbon, 50 mL HOAc and 7.5 mL perchloric acid. The mixture was shaken under 50 psi of hydrogen overnight. The catalyst was filtered off and the filtrate concentrated in vacuo. The residue was partitioned between $Et_2O$ and 3N NaOH. The organics were washed with $H_2O$, brine and dried ($K_2CO_3$). The solvent was evaporated in vacuo. After a flash chromatography on silica gel (90:10:1, $CH_2Cl_2$:MeOH:$NH_4OH$) the product was converted to the fumarate salt in 2-PrOH to give 430 mg of a white solid: mp. 157°–159° C.

Mass spectrum (Cl-$CH_4$) m/z 235 (M+ 1). $^1$H NMR ($Me_2SO$ d-6) δ7.25 (m, 2 H); 7.1 (m, 2 H); 6.5 (s, 2 H); 3.3-3.1 (m, 2 H); 3.15 (m, 1 H); 2.9 (bd, 1 H); 2.65 (m, 1 H); 2.6 (s, 3 H); 2.3 (m, 2 H); 1.8 (m, 2 H); 1.6 (m, 2 H); 1.3 (m, 2 H).

PROCEDURE S

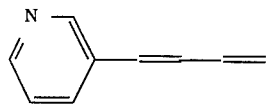 WWW 1-(Pyridin-3-yl)-1,3-butadiene

To a solution of 860 mL of 1M sodium hexamethyldisilazide in THF was added 700 mL of dry THF and 361 g (0.94 mole) of allyl triphenylphosphonium bromide at 0°–5° C. under argon. After stirring the mixture cold for 1 h, a solution of 91.8 g (0.86 mole) of 3-pyridinecarboxaldehyde in 300 mL of dry THF was added portionwise keeping the reaction mixture below 15° C. After 3 h at 10° C., 100 mL of $H_2O$ and 1000 mL of $Et_2O$ were added. The organic layer was dried ($MgSO_4$) and then evaporated in vacuo to an oil. Flash chromatography ($SiO_2$) eluting with 20% acetone: 80% $CH_2Cl_2$ gave an oil. Kugelrohr distillation gave an oil: bp 55°–79° C. (0.005 Torr).

Mass spectrum (Cl-$CH_4$) m/z 132 (m+1) $^1$H NMR ($CDCl_3$) δ5.12–5.28 (m, 1H); 5.29–5.42 (m, 1H); 6.22–6.51 (m, 2H); 6.64–6.8 (m, 1H); 7.11–7.22 (m, 1H); 7.51–7.68 (m, 2H); 8.31–8.42 (m, 1H); 8.48–8.58 (m, 1H).

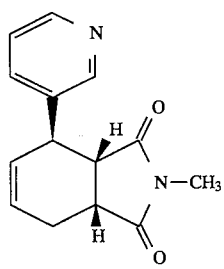

VVV

2-Methyl-4α-(pyridin-3-yl)-3aα,4,7,7aα-tetrahydro-1H-isoindole-1,3(2H)-dione A solution of 31.6 g (0.24 mole) of 1-(pyridin-3-yl)-1,3-butadiene, WWW, and 27.3 g (0.24 mole) of N-methylmaleimide in 82 mL of xylene was heated in a sealed bottle for 18 h in an oil bath at 125° C. The xylene was evaporated in vacuo to an oily residue. The 2 diastereoisomers were separated using flash chromatography on SiO$_2$ eluting with 20% acetone: 80% CH$_2$Cl$_2$. The first compound that eluted was 2-methyl-4α-(pyridin-3-yl)-3aα,4,7,7aα -tetrahydroiso-1H-isoindole-1,3(2H)-dione as a yellow oil.

$^1$H NMR (CDCl$_3$): δ2.4–2.6 (m, 2H); 3.1 (s, 3H); 3.12–3.22 (m, 1H); 3.22–3.3 (dd, 1H); 3.02–3.15 (m, 1H); 6.05–6.1 (m, 1H); 6.1–6.15 (m, 1H); 7.28–7.31 (m, 1H); 7.6–7.65 (d, 1H); 8.5–8.65 (m, 2H). Exact Mass MH+ calcd. 243.1134; found 243.1176.

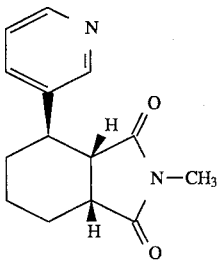

UUU

2-Methyl-4α-(pyridin-3-yl)-3aα,7aα-hexahydro-1H-isoindole-1,3(2H)-dione

A solution of 4.04 g (0.0166 mole) of 2-methyl-4α-(pyridin-3-yl)-3aα,4,7,7aα -tetrahydro-1H-isoindole-1,3(2H)-dione, VVV, in 100 mL of EtOAc was added to 4 g of 10% palladium on carbon and placed on the Paar hydrogenator at 60 psi of hydrogen for 2 h. The catalyst was filtered off, and the filtrate evaporated in vacuo to give a solid: mp 110°–112° C.

$^1$H NMR (CDCl$_3$) δ1.35–1.90 (m, 5H); 2.2–2.3 (m, 1H); 2.65–2.72 (m, 1H); 3.0 (s,3 H); 3.02–3.15 (m, 2H); 7.25–7.3 (m, 1H); 7.5–7.53 (dd, 1H); 8.50–8.55 (m, 2H). Anal. calcd for C$_{14}$H$_{16}$N$_2$O$_2$: C, 68.83; H,6.60; N, 11.47 Found: C, 68.73; H,6.64; N, 11.37

Example 23

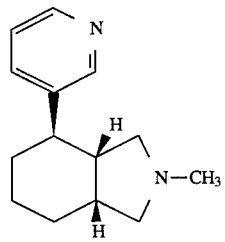

Cp-33

2-Methyl-4α-(pyridin-3-yl)-3aα,7aα-octahydro-1H-isoindole Fumarate

To a solution of 13 g (53 mM) of 2-methyl-4α-(pyridin-3-yl)-3aα7aα -hexahydro-1H-isoindole-1,3(2H)-dione, UUU, in 130 mL of dry THF was added 400 mL of a solution of 1M borane-THF under argon, and refluxed for 17 h. Then 28.8 mL of H$_2$O was added portionwise at room temperature. The solvent was evaporated in vacuo, and 300 mL of propionic acid added. After refluxing for 6 h, the propionic acid was evaporated in vacuo, and 300 mL of 3N NaOH solution was added. After heating on a steam bath for 2 h, the reaction mixture was extracted with ether and the ether solution dried (K$_2$CO$_3$). The Et$_2$O was evaporated in vacuo to an oil. Flash chromatography (SiO$_2$) eluting with 80 parts CH$_2$Cl$_2$:20 parts MeOH: 2 parts ammonium hydroxide, gave 6.67 g of a tan oil. The oil was dissolved in a MeOH solution containing 3.6 g of fumaric acid. A sample was recrystalized from 2-PrOH to give a solid: mp 138°–140° C.

Mass spectrum (Cl-CH$_4$) m/z 217 (m+ 1) H$^1$NMR (CDCl$_3$):δ1.42–1.78 (m, 6H); 2.32–2.5 (m, 1H); 2.61–2.83 (m, 6H); 2.91–3.02 (m,1H); 3.03–3.15 (t,1H); 3.30–3.45 (t,1H); 6.5 (s, 2H); 7.28–7.35 (m,1H); 7.63–7.72 (m,1H); 8.38–8.45 (m,1H); 8.46–8.51 (d, 1H). Anal. calcd for C$_{14}$H$_{20}$N$_2$.C$_4$H$_4$O$_4$: C,65.04 H,7.28; N, 8.43 Found C,65.01; H,7.40; N,8.52

Example 24

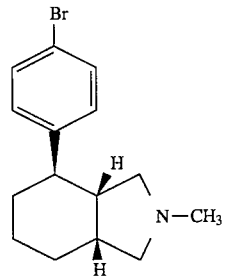

Cp-34

Employing the procedures of the foregoing example and starting with 4-bromobenzaldehyde in place of pyridinecarboxaldehyde, there was obtained: 4α-(4-bromophenyl)-2-methyl-3aα,7aα-octahydro-1H-isoindole fumarate: mp 222°–224° C.

Anal. Calcd for C$_{15}$H$_{20}$BrN.C$_4$H$_4$O$_4$: C, 55.62; H, 5.90; N, 3.41 Found C, 55.65; H, 5.92 N, 3.35

Example 25

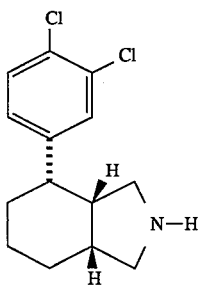

Cp-35

4β-(3,4-dichlorophenyl)-3aα,7aα-octahydro-1H-isoindole

Employing a minor variation of the procedure of Example 3 wherein the solvent for the Diels-Alder step was refluxing acetonitrile, substituting 3,4 -dichlorobenzaldehyde for 3-methoxybenzaldehyde in the Wittig step and substituting maleimide for N-methylmaleimide in the Diels-Alder step, there was obtained 4β-(3,4-dichlorophenyl)-3aα,7aα-octahydro-1H-isoindole fumarate: mp 166°–169° C.

Anal. calcd for: $C_{14}H_{17}Cl_2N \cdot C_4H_4O_4$: C, 55.97; H, 5.48; N, 3.63. Found: C, 55.94; H, 5.48; N, 3.62.

Procedure T

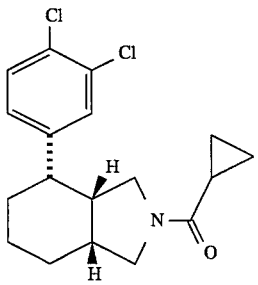

SSS

[4β-(3,4-Dichlorophenyl)-3aα,7aα-octahydro-1H-isoindol-2-yl]-cyclopropylmethanone To a mixture of 150 mg (0.5 mM) of 4β-(3,4-dichlorophenyl)-3aα,7aα -octahydro-1H-isoindole hydrochloride, Cp-35, in 5 mL of $CH_2Cl_2$ was added 1.5 mL of 1N NaOH solution and 3.5 mL of $H_2O$. Then, 52 mg (0.5 mM) of cyclopropanecarbonyl chloride was added and the mixture stirred for 30 min. The $CH_2Cl_2$ layer was separated, dried ($Na_2SO_4$), and evaporated in vacuo to give 170 mg of an oil. Flash chromatography ($SiO_2$) eluting with 20% acetone:80% hexane, gave a white solid.

Mass spectrum (Cl-$CH_4$) m/z 338(M+ 1) $H^1$NMR (CDCl$_3$/D$_2$O): δ0.65–082 (m,2H); 0.83–1.08 (m, 2H); 1.4–1.61 (m, 3H); 1.62–1.86 (m, 3H); 1.87–2.09 (m,1H); 2.18–2.4 (m, 1H); 2.5–2.8 (m, 1H); 2.92–3.18 (m, 2H); 3.19–3.32 (t, 1H); 3.33–3.52 (m, 2H); 3.65–3.80 (m, 1H); 7.0–7.1(m, 1H); 7.2–7.4 (m, 2H).

Example 26

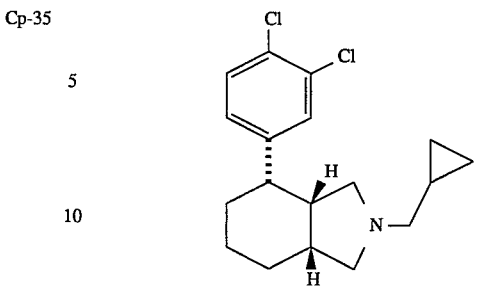

Cp-37

2-Cyclopropylmethyl-4β-(3,4-dichlorophenyl)-3aα,7aα-octahydro-1H-isoindole Oxalate To a solution of 890 mg (2.65 mM) of [4β-(3,4-dichlorophenyl)-3aα,7aα -octahydro-1H-isoindol-2-yl]-cyclopropyl-methanone, SSS, in 10 mL of dry THF was added 13.2 mL of 1M borane/THF solution and refluxed for 17 h. Then 1 mL of $H_2O$ was added to the reaction mixture at room temperature and stirred for 10 min. The THF was evaporated in vacuo and 3.2 mL of propionic acid added. The mixture was refluxed for 6 h, then basified with 3N NaOH solution, and extracted with $CH_2Cl_2$. The $CH_2Cl_2$ solution was dried ($K_2CO_3$), and evaporated in vacuo to a yellow oil. Flash chromatography ($SiO_2$) eluting with 10% MeOH:90% $CH_2Cl_2$ gave an oil which was partitioned between 3N NaOH solution and ether. The ether solution was dried ($K_2CO_3$) and evaporated in vacuo to an oil. The oil was dissolved in a MeOH solution containing 130 mg oxalic acid, and the salt was recrystallized from 2-PrOH to give a white solid: mp 159°–163° C.

Mass spectrum (Cl-$CH_4$) m/z 324(m+ 1) $H^1$NMR (Me$_2$SO-d6): δ0.2–0.35 (m, 2H); 0.4–0.6 (m, 2H); 0.88–1.02 (m,1H);1.18–1.45 (m, 2H); 1.5–1.68 (m, 2H); 1.69–1.88 (m, 2H); 2.2–2.4 (m, 1H); 2.58–2.78 (m, 2H); 2.8–3.05 (m, 2H); 3.06–3.2 (m, 2H); 3.25–3.5 (m, 2H); 7.22–7.3 (dd,1H); 7.4–7.6 (m, 2H). Anal. Calcd for $C_{18}H_{23}Cl_2N \cdot C_2H_2O_4$: C, 57.98; H, 6.08; N, 3.38 Found: C, 58.01; H, 6.11; N, 3.38

Example 27

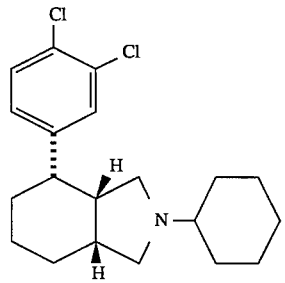

Cp-38

2-Cyclohexyl-4β-(3,4-dichlorophenyl)-3aα,7aα-octahydro-1H-isoindole Fumarate

To a solution of 780 mg (2.9 mM) of 4β-(3,4-dichlorophenyl)-3aα,7aα -octahydro-1H-isoindole, Cp-35, and 284 mg (2.89 mmol) of cyclohexanone in 10 mL of dry 1,2-dichloroethane was added 68 mg (2.9 mM) of sodium triacetoxyborohydride and 0.16 mL of glacial HOAc and stirred at room temperature overnight. The reaction was basified with 3N NaOH solution, and extracted with $CH_2Cl_2$. The $CH_2Cl_2$ solution was washed with brine, dried ($K_2CO_3$), and evaporated in vacuo to an oil. The oil was dissolved in a solution of 2-PrOH containing 277 mg of fumaric acid, and the salt recrystallized from MeOH-acetonitrile to give a solid: mp 221° C.

Mass spectrum (Cl-$CH_4$) m/z 352(m+1) $H^1$NMR ($CDCl_3$):δ1.0–1.5 (m, 8H); 1.5–1.95 (m,8H); 2.05–2.2 (m,3H); 2.4–2.45 (d,1H); 2.5–2.52 (m, 2H); 2.9–3.05 (m, 2H); 7.0–7.08 (dd, 1H); 7.25–7.35 (m, 2H). Anal. Calcd for $C_{20}H_{27}Cl_2N$-$C_4H_4O_4$: C, 61.54; H, 6.67; N, 2.99 Found: C, 61.37; H, 6.64; N, 3.00

Example 28

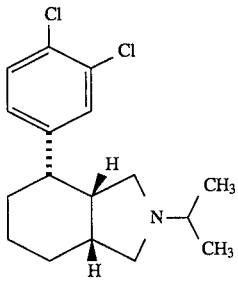

Cp-39

4β-(3,4-dichlorophenyl)-2-methylethyl-3aα,7aα-octahydro-1H-isoindole

Employing the procedure of the foregoing example and starting with acetone in place of cyclohexanone, there was obtained: 4β-(3,4-dichlorophenyl)-2 -methylethyl-3aα,7aα-octahydro-1H-isoindole fumarate: mp 207°–210° C.

anal. calcd for: $C_{17}H_{23}Cl_2N$-$C_4H_4O_4$: C, 58.88; H, 6.35; N, 3.27. Found: C, 58.60; H, 6.61; N, 3.24.

Example 29

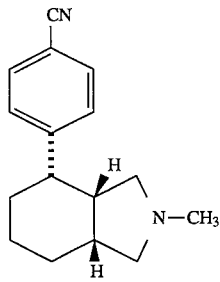

Cp-40

4β-Cyanophenyl-2-methyl-3aα,7aα-octahydro-1H-isoindole fumarate hydrate (6:6:1)

A solution of 2.0 g (6.85 mmol) of 4β-bromophenyl-2-methyl-3aα,7aα -octahydro-1H-isoindole, Cp-44 1.14 g (10.73 mmol) of CuCN and 39 mg (0.034 mmol) of tetrakis(triphenylphosphine)palladium(0) in 7.0 mL of pyridine under argon was heated under reflux for 3 days. The mixture was cooled and partitioned between $Et_2O$ and $NH_4OH$. The organic solution was dried ($K_2CO_3$) and the solvent evaporated. The residue was recrystallized twice from methyl t-butyl ether/methylcyclohexane. A fumarate salt was prepared and was recrystallized successively from 2-PrOH and MeOH to afford the title compound as a white solid: mp 198°–200° C.

$^1$H NMR ($Me_2SO$-$d_6$) δ7.8 (dd, 2H), 7.45 (dd, 2H), 6.47 (s, 2H), 3.3-3.1 (m, 3H), 2.95 (dd, 1H), 2.73 (m, 1H), 2.55 (s, 3H), 2.3 (m, 2H), 1.8 (m, 2H), 1.62 (m, 2H), 1.36 (m, 2H). Anal. calcd for $C_{16}H_{20}N_2$-$C_4H_4O_4$-0.167 $H_2O$: C, 66.83; H, 6.82, N, 7.79. Found: C, 66.68; H, 6.84; N, 7.69.

Example 30

Employing the procedures of Examples 1 and 2 and substituting 2' -chlorocinnamoyl chloride or 2',6'-dichlorocinnamoyl chloride for m-trifluoromethylcinnamoyl chloride, the following compounds were obtained:

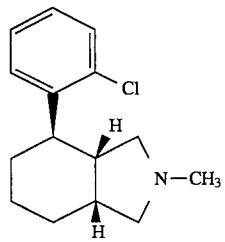

Cp-41

4α-(2-Chorophenyl)-2-methyl-3aα,7aα-octahydro-1H-isoindole fumarate mp 168°–17° C. Anal. calcd for: $C_{15}H_{20}ClN$-$C_4H_4O_4$: C, 62.19; H, 6.85; N, 3.77. Found: C, 62.38; H, 6.61; N, 3.83.

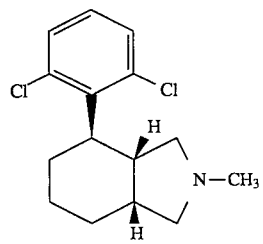

Cp-42

4α-(2,6-Dichorophenyl)-2-methyl-3aα,7aα-octahydro-1H-isoindole di(cyclohexylsulfamate)

mp 128°–129° C. Anal. calcd for: $C_{15}H_{19}ClN$-$C_4H_4O_4$: C, 50.45; H, 7.06; N, 6.54. Found: C, 50.26; H, 7.05; N, 6.53.

Example 31

Employing the procedure of Example 3 or a minor variation thereof wherein the solvent for the Diels-Alder step was refluxing acetonitrile (aryl= p-bromophenyl, 3,4-dichlorophenyl and 3-pyridyl) and substituting the appropriate 1-aryl-1,3-butadiene for 3-methoxyphenyl-1,3-butadiene, the following compounds were obtained:

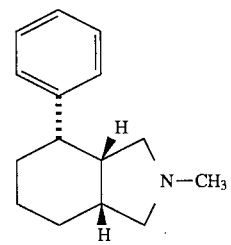

Cp-43

2-Methyl-4β-(phenyl)-3aα,7aα-octahydro-1H-isoindole fumarate mp 152°–153° C. Anal. calcd for: $C_{15}H_{21}N\cdot C_4H_4O_4$: C, 68.86; H, 7.60; N, 4.23. Found: C, 68.87; H, 7.46; N, 4.14.

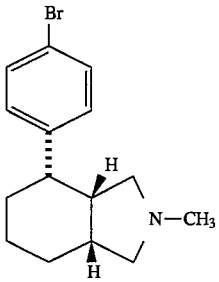

Cp-44

4β-(4-Bromophenyl)-2-methyl-3aα,7aα-octahydro-1H-isoindole fumarate mp 193°–194° C. Anal. calcd for: $C_{15}H_{20}BrN\cdot C_4H_4O_4$: C, 55.62; H, 5.90; N, 3.41. Found: C, 55.67; H, 5.94; N, 3.40.

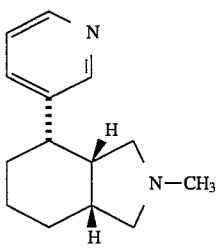

Cp-45

2-Methyl-4β-(pyridin-3-yl)-3aα,7aα-octahydro-1H-isoindole fumarate hydrate (5:5:3)

mp 152°–153° C. Anal. calcd for: $C_{14}H_{20}N_2\cdot C_4H_4O_4\cdot 0.6\ H_2O$: C, 62.99; H, 7.40; N, 8.16; $H_2O$, 3.14. Found: C, 62.81; H, 7.04; N, 7.95; $H_2O$, 2.64.

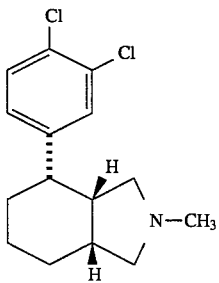

Cp-46

4β-(3,4-Dichlorophenyl)-2-methyl-3aα,7aα-octahydro-1H-isoindole fumarate mp 158°–165° C. Anal. calcd for: $C_{15}H_{19}Cl_2N\cdot C_4H_4O_4$: C, 57.01; H, 5.79; N, 3.50. Found: C, 56.82; H, 5.85; N, 3.49.

Example 32

Employing the procedure of Example 10 and substituting isopropylamine for methylamine, the following compound was obtained:

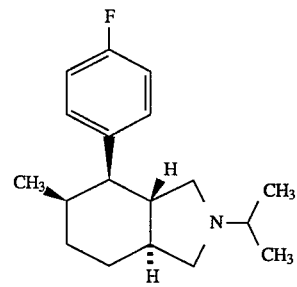

Cp-47

4α-(4-Fluorophenyl)-5α-methyl-2-methylethyl-3aα,7aβ-octahydro-1H-isoindole fumarate mp 215°–216° C. Anal. calcd for: $C_{18}H_{26}FN\cdot C_4H_4O_4$: C, 67.49; H, 7.72; N, 3.57. Found: C, 67.65; H, 8.02; N, 3.45.

Example 33

Employing the procedure of Example 10 and 12 and substituting isopropylamine for methylamine, the following compound was obtained:

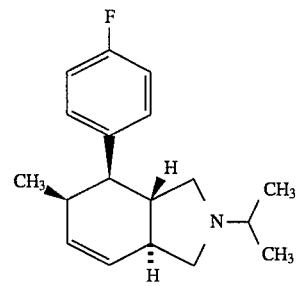

Cp-48

4α-(4-Fluorophenyl)-5α-methyl-2-methylethyl-2,3,3aα,4,5,7aα-hexahydro-1H-isoindole fumarate mp 208°–211° C. Anal. calcd for: $C_{18}H_{24}FN\cdot C_4H_4O_4$: C, 67.85; H, 7.24; N, 3.60. Found: C, 67.58; H, 7.46; N, 3.50.

Example 34

Employing the procedure of Example 10 (Procedure I) and substituting isopropylamine for methylamine, then treating the intermediate analogous to compound YY wherein the methyl group on nitrogen is replaced with isopropyl with LAH as in Example 12 the following compound was obtained:

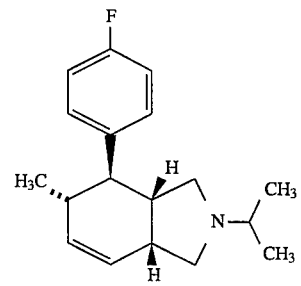

Cp-49

4α-(4-Fluorophenyl)-5β-methyl-2-methylethyl-2,3,3aα,4,5,7aα-hexahydro-1H-isoindole fumarate mp 184°–185° C. Anal. calcd for: $C_{18}H_{24}FN\cdot C_4H_4O_4$: C, 67.85; H, 7.24; N, 3.60. Found: C, 67.72; H, 7.11; N, 3.53.

Example 35

Employing the procedures of Example 14 and 15 (Procedure L) and starting with 1-phenyl-1,3-butadiene in place of 1-(3-methylphenyl)-1,3-butadiene, the following compounds were obtained:

Cp-50

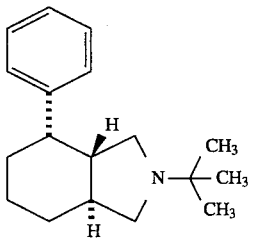

2-(1,1-dimethylethyl)-4β-(phenyl)-3aα,7aβ-octahydro-1H-isoindole fumarate mp 214°–216° C. Anal. calcd for: $C_{18}H_{27}N\text{-}C_4H_4O_4$: C, 70.75; H, 8.37; N, 3.75. Found: C, 70.89; H, 8.41; N, 3.73.

Cp-51

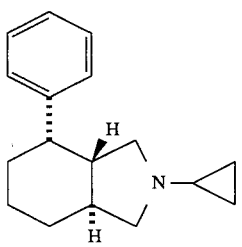

2-Cyclopropyl-4β-(phenyl)-3aα,7aβ-octahydro-1H-isoindole fumarate mp 148°–152° C. Anal. calcd for: $C_{17}H_{23}N\text{-}C_4H_4O_4$: C, 70.56; H, 7.61; N, 3.91. Found: C, 70.22; H, 7.75 N,3.79.

Example 36

Employing the procedure of Example 16 (Procedure M) and starting with 1-phenyl-1,3-butadiene in place of 1-(4-methylthiophenyl)-1,3-butadiene, the following compounds were obtained:

Cp-52

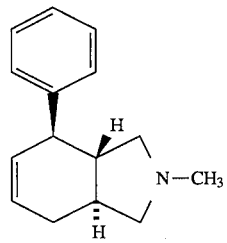

2-Methyl-4α-phenyl-2,3,3aα,4,7,7aβ-hexahydro-1H-isoindole fumarate mp 123°–127° C. Anal. calcd for: $C_{15}H_{19}N\text{-}C_4H_4O_4$: C,69.28; H, 7.04; N, 4.25. Found: C, 68.99; H, 6.99; N, 4.28.

Cp-53

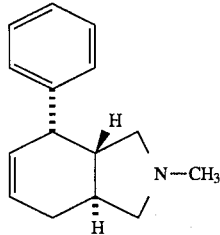

2-Methyl-4β-phenyl-2,3,3aα,4,7,7aβ-hexahydro-1H-isoindole fumarate mp 153°–155° C. Anal. calcd for $C_{15}H_{19}N\text{-}C_4H_4O_4$: C,69.28; H, 7.04; N, 4.25. Found: C, 69.00; H, 7.22; N, 4.14.

What is claimed is:

1. A compound having analgesic activity of the general formula:

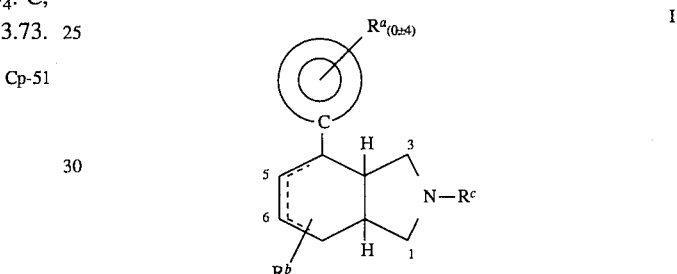

including the purified stereoisomers and pharmaceutically acceptable salts thereof, wherein:

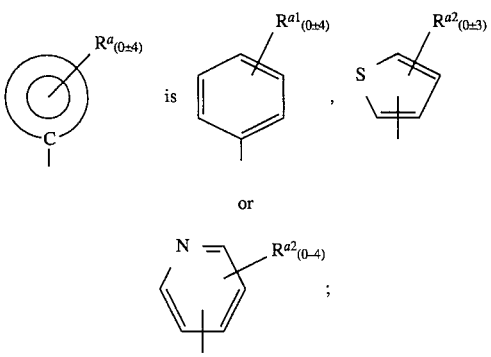

$R^{a1}$ is selected from the group consisting of hydroxy, halogen, $C_{1-4}$alkyl, substituted $C_{1-4}$alkyl (wherein the substituent is $C_{1-4}$alkoxy, hydroxy or perhalo), $C_{1-4}$alkoxy, substituted $C_{1-4}$alkoxy (wherein the substituent is perfluoro), $C_{1-4}$alkylthio, cyano, nitro, amino, $C_{1-4}$alkylamino, di$C_{1-4}$alkylamino, $C_{1-4}$alkylsulfonyl, $C_{1-4}$alkylsulfinyl, phenyl, phenylthio, $C_{1-4}$acylamino, carboxy, $C_{1-4}$acyl and benzoyl;

$R^{a2}$ is selected from the group consisting of halogen or $C_{1-4}$alkyl;

$R^b$ is 5-, 6-, or 7-position substituted and selected from the group consisting of hydrogen and $C_{1-4}$ alkyl; and $R^c$ is selected from the group consisting of hydrogen, $C_{1-4}$ alkyl, substituted $C_{1-4}$alkyl (wherein the substituent is one or two phenyl groups or $diC_{1-4}$alkylamino), $C_{1-4}$alkenyl, benzyl, $C_{1-6}$cycloalkylmethyl and $C_{1-6}$cycloalkyl;

with the proviso that there is 0 or 1 unsaturated bond in the isoindole ring and with the proviso that where the stereoisomer is:

a) the 3aβ, 4β, 7aα diastereomer, then a double bond joins the 5- and 6-position carbons or the 6- and 7-position carbons;

b) the 3aβ, 4α, 7aα or the 3aβ, 4α, 7aβ diastereomers, then the double bond joins the 5- and 6-position carbons; and c) the 3aβ, 4α, 7aβ diastereomer, then the double bond joins the 6- and 7-position carbons.

2. The compound of claim 1 of the general formula:

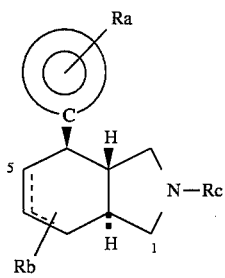

including the purified stereoisomers thereof.

3. The compound of claim 1 of the general formula:

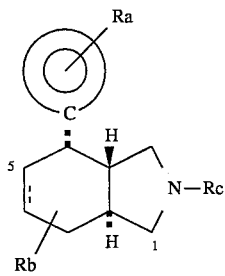

including the purified stereoisomers thereof.

4. The compound of claim 1 of the general formula:

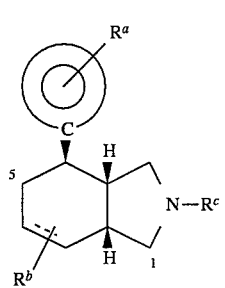

including the purified stereoisomers thereof.

5. The compound of claim 1 of the general formula:

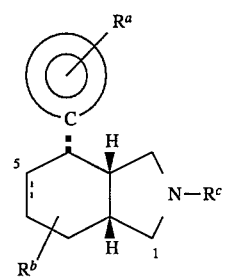

including the purified stereoisomers thereof.

6. The compound of claim 1 of the general formula:

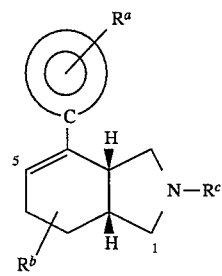

including the purified stereoisomers thereof.

7. The compound of claim 1 of the general formula:

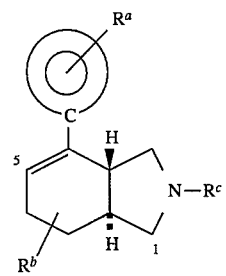

including the purified stereoisomers thereof.

8. The compound of claim 1 wherein:

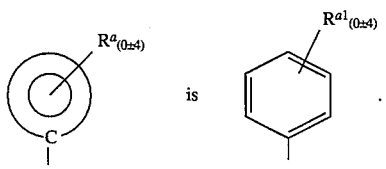

9. The compound of claim 1 wherein:

$R^{a1}$ is selected from the group consisting of hydroxy, bromine, chlorine, fluorine, methyl, ethyl, n-propyl, i-propyl, t-butyl, methoxymethyl, ethoxyethyl, hydroxymethyl, hydroxyethyl, hydroxypropyl, trifluoromethyl, trichloromethyl, methoxy, ethoxy, t-butoxy, trifluoromethoxy, methylthio, ethylthio, n-propylthio, cyano, nitro, amino, methylamino, ethylamino, n-propylamino, dimethylamino, diethylamino, methylethylamino, methylsulfonyl, ethylsulfonyl, n-propylsulfonyl, methylsulfinyl, ethylsulfinyl, n-propylsulfinyl, phenyl, phenylthio, formylamido, acetamido, propionylamido, carboxy, formyl, acetyl, propionyl and benzoyl.

10. The compound of claim 1 wherein:

$R^{a2}$ is selected from the group consisting of bromine, chlorine, fluorine, methyl, ethyl, n-propyl, i-propyl and t-butyl.

11. The compound of claim 1 wherein:
$R^b$ is selected from the group consisting of hydrogen, methyl, ethyl, n-propyl, i-propyl and t-butyl.

12. The compound of claim 1 wherein:
$R^c$ are selected from the group consisting of hydrogen, methyl, ethyl, n-propyl, i-propyl, t-butyl, benzyl, diphenylmethyl, dimethylaminomethyl, dimethylaminoethyl, dimethylaminopropyl, diethylaminomethyl, diethylaminoethyl, allyl, benzyl, cyclopropylmethyl, cyclopropyl and cyclohexylmethyl.

13. The compound of claim 1 wherein said pharmaceutically acceptable salt is a salt made with an acid selected from the group consisting of hydrochloric, hydrobromic, hydroiodic, perchloric, sulfuric, nitric, phosphoric, acetic, proprionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic and a salt made with sacchrine.

14. A compound selected from the group consisting of:

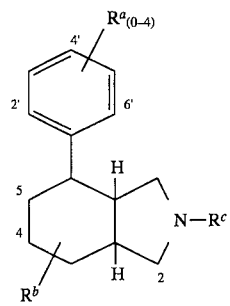

wherein $R^a$, $R^b$ and $R^c$ are simultaneously selected from the group consisting of:

| $R^a$ | $R^b$ | $R^c$ |
|---|---|---|
| 4'-F | 5-Me | Me, |
| 3'-methoxy | H | Me, |
| 3'-methoxy | H | H, |
| 3'-$CF_3$ | H | Me, |
| 3'-methoxy | H | benzyl, |
| 2',3'-dimethoxy | H | Me, |
| 3',4'-dichloro | H | Me, |
| 3'-OH | H | Me, |
| — | H | Me, |
| 4'-$CF_3$ | H | Me, |
| 3'-$CF_3$ | H | n-butyl, |
| 4'-$NO_2$ | H | Me, |
| 4'-$NH_2$ | H | Me, |
| 4'-$NHCOCH_3$ | H | Me, |
| 4'-Cl | H | Me, |
| 2'-Cl | H | Me, |
| 2',5'-Cl | H | Me, |
| 4'-F | H | Me, |
| 4'-methoxy | H | Me, |
| 3',4'-dimethoxy | H | Me, |
| 4'-i-propyl | H | Me, |
| 4'-CN | H | Me, |
| 4'-Br | H | Me, |
| 4'-SMe | H | Me, |
| 4'-$SO_2$Me | H | Me, and |
| 3'-methoxy | H | benzyl, | including the purified stereoisomers thereof.

15. A compound selected from the group consisting of:

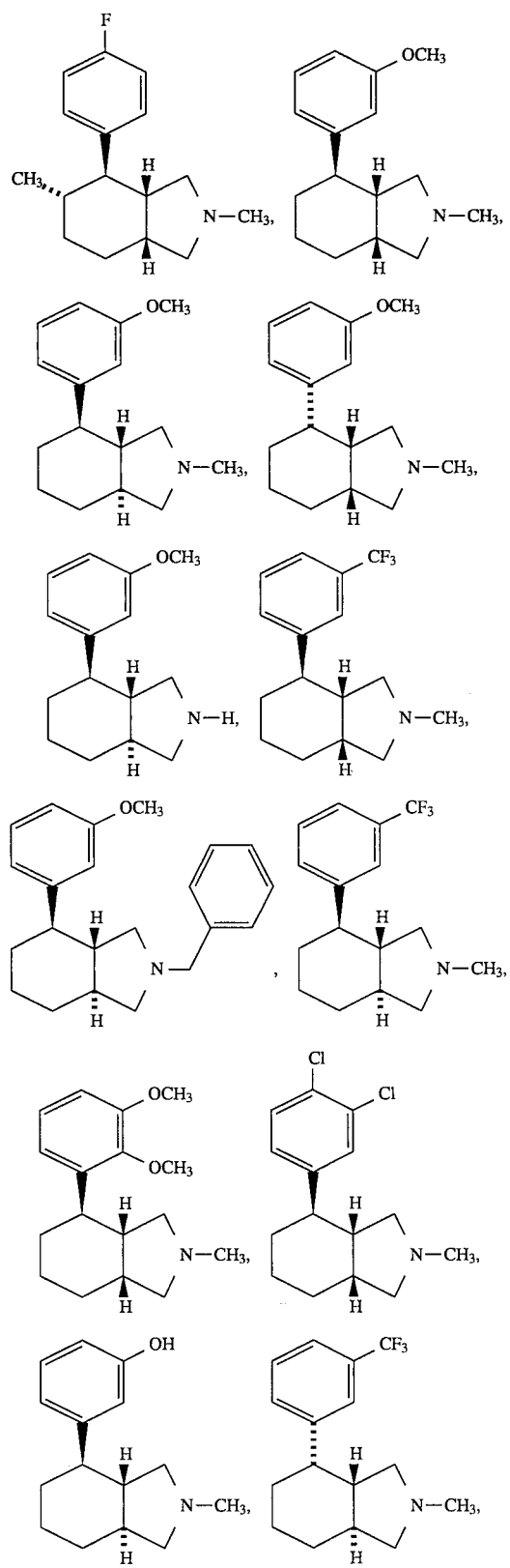

77
-continued
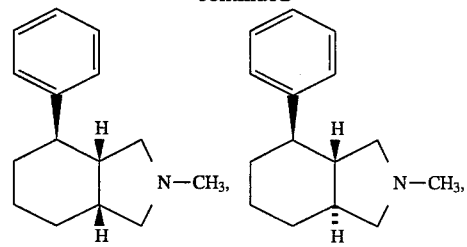
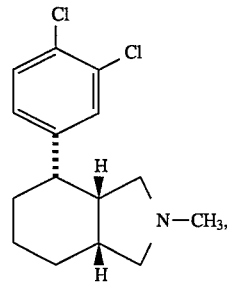
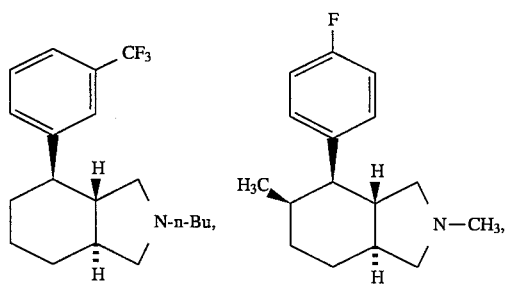
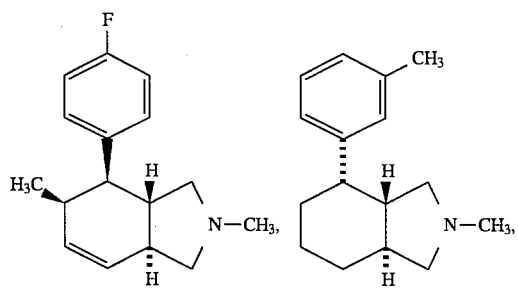
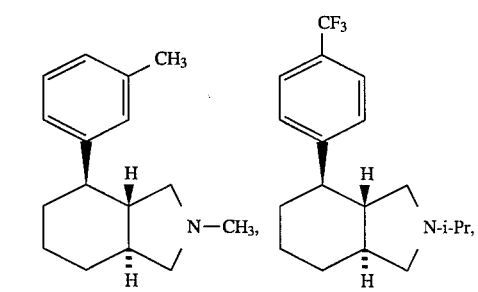
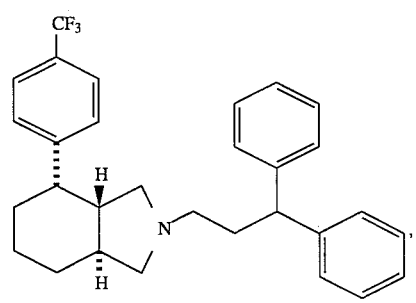
78
-continued
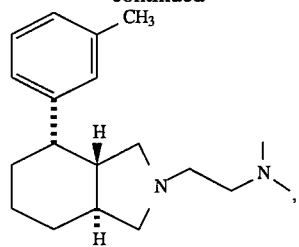
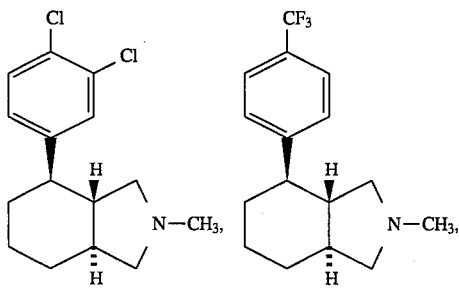
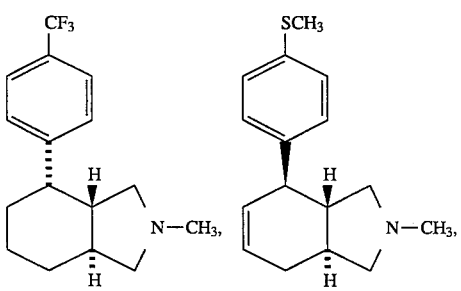
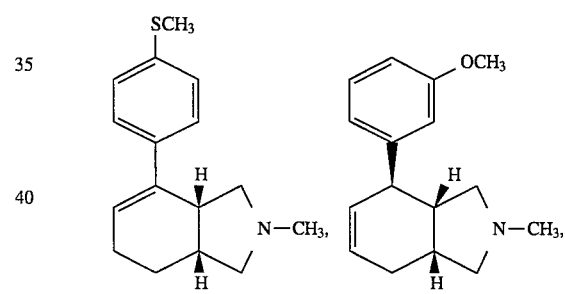
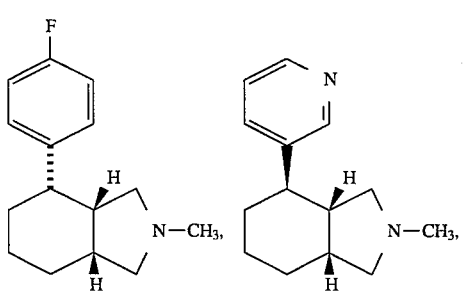
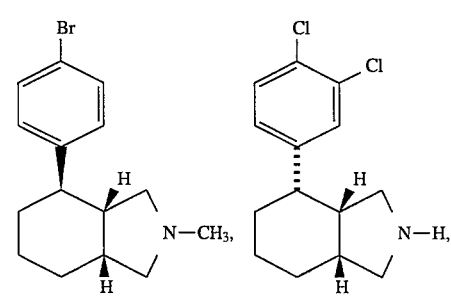

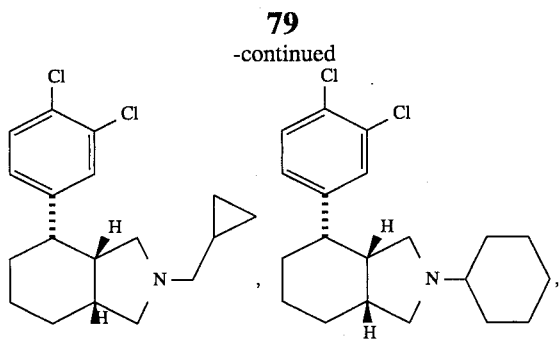
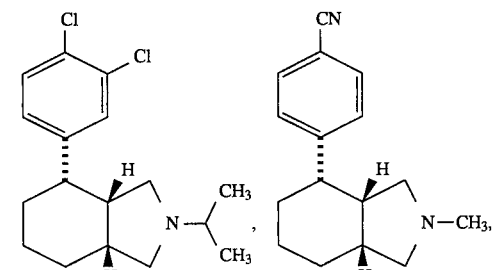
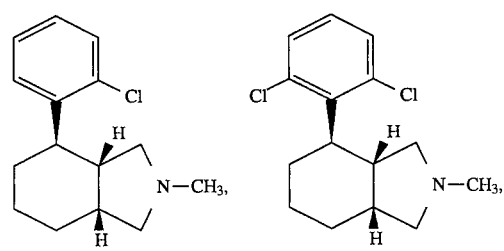
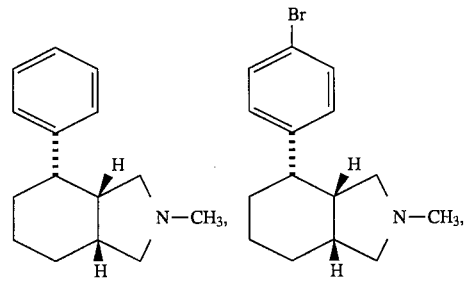
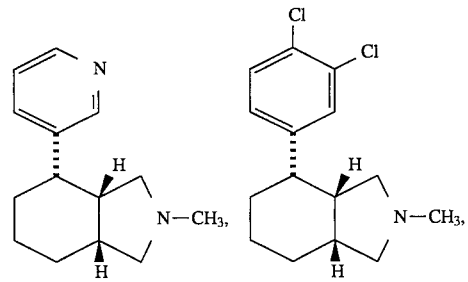
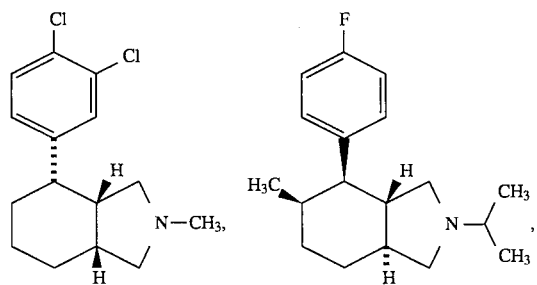

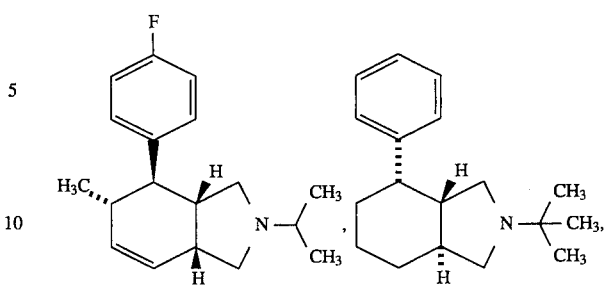

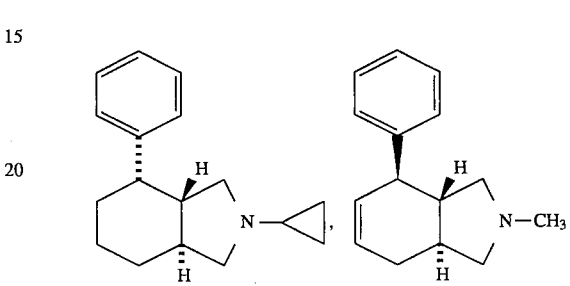

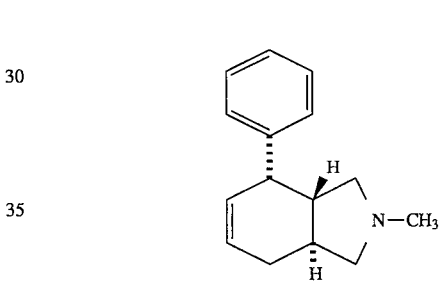

including the purified stereoisomers thereof.

16. The compound of claim 15 selected from the group consisting of:

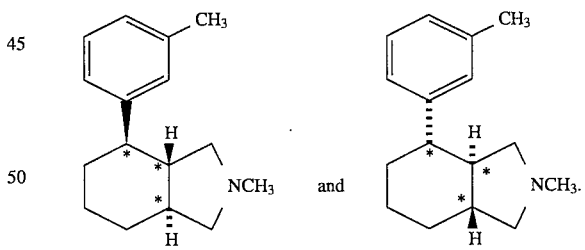

17. A pharmaceutical composition effective as an analgesic in mammals comprising a pharmaceutically acceptable carrier and an effective amount of the compound of claim 1.

18. A method for inducing an analgesic effect in mammals comprising the step of administering an effective amount of the compound of claim 1 in admixture with a pharmaceutically acceptable carrier.

* * * * *